US007109175B1

(12) United States Patent
Bkaily et al.

(10) Patent No.: US 7,109,175 B1
(45) Date of Patent: Sep. 19, 2006

(54) SPECIFIC STEADY-STATE R-TYPE $CA^{2+}$ CHANNEL BLOCKERS AND USE THEREOF

(75) Inventors: Ghassan Bkaily, Sherbrooke (CA); Pedro D'Orleans-Juste, Sherbrooke (CA); Joao B. Calixto, Florianopolis (BR); Rosendo A. Yunes, Florianopolis (BR)

(73) Assignee: Universite de Sherbrooke, Sherbrooke (CA)

( * ) Notice: Subject to any disclaimer, the term of this patent is extended or adjusted under 35 U.S.C. 154(b) by 0 days.

(21) Appl. No.: 10/291,852

(22) Filed: Nov. 7, 2002

Related U.S. Application Data

(63) Continuation of application No. 09/509,462, filed on Jul. 20, 2000, now abandoned.

(51) Int. Cl.
*A61K 31/70* (2006.01)
(52) U.S. Cl. .............................. 514/26; 514/23; 514/54
(58) Field of Classification Search ............... 536/1.11, 536/123.1; 514/23, 26, 54
See application file for complete search history.

(56) References Cited

FOREIGN PATENT DOCUMENTS

EP    0 359 311 A1    3/1990

OTHER PUBLICATIONS

Edson et al. "The structure of velutinol A is (15R,16R, 20S)-14,16:15,20:16:2triepoxy-15,16-seco-14β,17α-pregn-5-ene-3β,15diol. A combined quantiative Overhauser effect and molecular modeling study" J. Chem. Soc., Perkin Trans. 2, 1996: pp. 1359-1366.
Bkaily et al. "The use of confocal microscopy in the investigation of cell structure and function in the heart, vascular endothelium and smooth muscle cells" Molecular and Cellular Biochemistry 172 (1997): pp. 171-194.
Bkaily et al. "Nuclear Membrane Receptors and Channels: Potential Therapeutical Targets for Drug Action" Drug Development Research 42 (1997): pp. 211-218.
Bkaily et al. "Bradykinin activates R-, T-, and L-type $Ca^{2+}$ channels and induces a sustained increase of nuclear $Ca^{2+}$ in aortic vascular smooth muscle cells[1]" Can. J. Physiol. Pharmacol. 75 (1997): pp. 652-660.
Bkaily et al. "Increases of T-type $Ca^{2+}$ current in heart cells of the cardiomyopathic hamster" Molecular and Cellular Biochemistry 176 (1997): pp. 199-204.
Bkaily et al. "Modulation of cytosolic and nuclear $Ca^{2+}$ and $Na^+$ transport by taurine in heart cells" Molecular and Cellular Biochemistry 170 (1997): pp. 1-8.
Bkaily et al. "Endothelin-1 and insulin activate the steady-state voltage dependent R-type $Ca^{2+}$ channel in aortic smooth muscle cells via a pertussis toxin and cholera toxin sensitive G-protein" Molecular and Cellular Biochemistry 183 (1998): pp. 39-47.
Ghassan Bkaily "Ionic Channels in Vascular Smooth Muscle" R. G. Landes Company (1994).

Vaz et al. "Antinociceptive action of 2-(4-Bromobenzoyl)-3-Methyl-4,6-Dimethoxy Benzofuran, a Novel Xanthoxyline Derivative on Chemical and Thermal Models of Nociception in Mice" The Journal of Pharmacology and Experimental Therapeutics (1996): pp. 304-312.
Neves et al. "Differential effects of *Mandevilla velutina* compounds on paw oedema induced by phospholipase $A_2$ and phospholipase C" European Journal of Pharmacology 243 (1993): pp. 213-219.
Raman et al. "Effects of Estradiol and Progesterone on Platelet Calcium Responses" American Journal of Hypertension 8 (1995): pp. 197-200.
Frode Saleh et al. "Anti-inflammatory effects of theophylline, cromolyn and salbutamol in a murine model of pleurisy" British Journal of Pharmacology 118 (1996): pp. 811-819.
Zhang et al. "Distinctive Pharmacology and Kinetics of cloned neuronal $Ca^2$ channels and their possible counterparts in mammalian CNS neurons" Neuropharmacology vol. 32, No. 11 (1993): pp. 1075-1088.
Randall et al. "Contrasting Biophysical and Pharmacological Properties of T-type and R-type Calcium Channels" Neuropharmacology, vol. 36, No. 7, (1997): pp. 879-893.
Burch et al. "A bradykinin antagonist inhibits carrageenan edema in rats" Archives of Pharmacology 342 (1990): pp. 18993.
Calixto et al. "The selective antagonism of bradykinin action on rat isolated uterus by crude *Mandevilla velutina* extract" Br. J. Pharmac 85 (1985): pp. 729-731.
Calixto et al. "Effect of a crude extract of *Mandevilla velutina* on contractions induced by bradykinin and [des-$Arg^9$]-bradikinin in isolated vessels of the rabbit" Br. J. Pharmac 88 (1986): pp. 937-941.
Calixto et al. "The competitive antagonistic effect of compounds from *Mandevilla velutina* on kinin-induced contractions of rat uterus and guinea-pig ileum in vitro" Br. J. Pharmacol. 94 (1988): pp. 1133-1142.
Compos et al. "Upregulation of $B_1$ receptor mediating des-$Arg^9$-BK-induced rat paw oedema by systemic treatment with bacterial endotoxin" British Journal of Pharmacology 117 (1996): pp. 793-798.
Compos et al. "Involvement of $B_1$ and $B_2$ receptors in bradykinin-induced rat paw oedema" British Journal of Pharmacology 114 (1995): pp. 1005-1013.
Calixto et al. "Antagonism of Kinin-induced contraction of isolated rat uterus by the crude hydroalcoholic extract from *Mandevilla illustris*" Gen. Pharmac. vol. 22, No. 1 (1991), pp. 99-101.

(Continued)

*Primary Examiner*—Elli Peselev
(74) *Attorney, Agent, or Firm*—Merchant & Gould P.C.

(57) ABSTRACT

The present invention relates to $Ca^{2+}$ channel blockers and more particularly to the R-type $Ca^{2+}$ channel blockers. More specifically, the invention relates to $Ca^{2+}$ channel blockers activity of *Mandevilla velutina* and *Mandevilla illustris*. The present invention further concerns saponin-like compounds isolated from *Mandevilla* species. The present invention also relates to the treatment of several pathologies that involve the nifedipine-insensitive but isradipine sensitive steady-state R-type $Ca^{2+}$ channel and the use of steady-state R-type $Ca^{2+}$ channel blockers in the treatment of these pathologies.

23 Claims, 59 Drawing Sheets

OTHER PUBLICATIONS

Calixto et al. "Kinin antagonist activity of compounds from *Mandevilla velutina* in the rat isolated uterus" Br. J. Pharmac. 91 (1987), pp. 199-204.

Gratton et al. "Pharmacological Properties of Endothelins and Big Endothelins in Ketamine/Xylazine or Urethane Anesthetized Rats" American Journal of Hypertension 8 (1995): pp. 1121-1127.

Damas et al. "Influence of a long-acting bradykinin antagonist, Hoe 140, on some acute inflammatory reactions in the rat" European Journal of Pharmacology 211 (1992): pp. 81-86.

Compos et al. "Antioedematogenic and antinociceptive actions of NPC 18521, a novel bradykinin $B_2$ receptor antagonist" European Journal of Pharmacology 316 (1996): pp. 227-286.

Moraes et al. "Jatrophone and 12-o-tetradecanoyl phorbol-13-acetate antagonism of stimulation of natural killer activity and lymphocyte proliferation" European Journal of Pharmacology 312 (1996): pp. 333-339.

Claing et al. "Role of R-type calcium channels in the response of the perfused arterial and venous mesenteric vasculature of the rat to platelet-activating factor" Br. J. Pharmacol. 112 (1994): pp. 1202-1208.

A.J. de Brum-Fernandes et al. "Characterization of the $PGE_2$ receptor subtype in bovine chondrocytes in culture" $PGE_2$ receptor in bovine chondrocytes: pp. 1597-1604.

Gratton et al. "Different pressor and broncoconstrictor properties of human big-endothelin-1, 2(1-38) and 3 in ketamine/xylazine-anaesthetized guinea-pigs" British Journal of Pharmacology 114 (1995): pp. 720-726.

Levy et al. "Diabetes Mellitus: A Disease of Abnormal Cellular Calcium Metabolism?" The American Journal of Medicine vol. 96 (1994): pp. 260-273.

Hargreaves et al. "Bradykinin is increased during acute and chronic inflammation: Therapeutic implications" Clin Pharmacol Ther (1988): pp. 613-621.

Jacobs et al. "Effect of Weight Reduction on Cellular Cation Metabolism and Vascular Resistance" Hypertension vol. 21, No. 3 (1993): pp. 308-314.

Johnson et al. "A Multicenter Comparison of adverse Reaction Profiles of Isradipine and Enalapril at Equipotent Doses in Patients with Essential Hypertension" J. Clim Pharmacol 35 (1995): pp. 484-492.

Lopez et al. "Spontaneous Calcium Waves Without Contraction in Cardiac Myocytes" Biochemical and Biophysical Research communications vol. 214, No. 3 (1995): pp. 781-787.

Grossman et al. "Cardiovascular Effects of Isradipine in Essential Hypertension" The American Journal of Cardiology vol. 68 (1991): pp. 65-70.

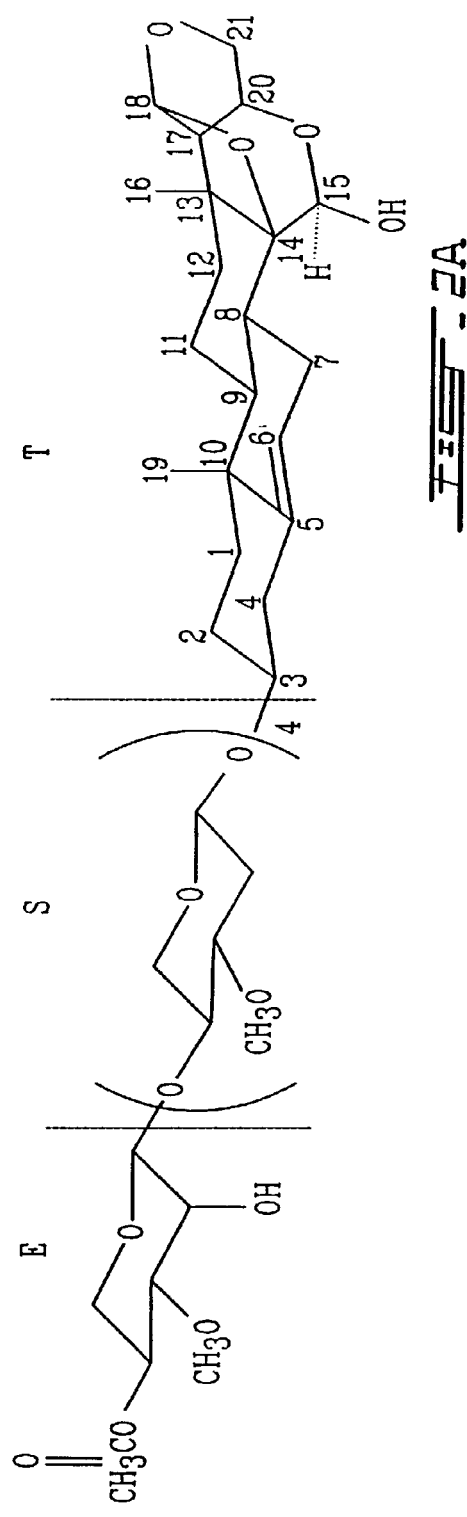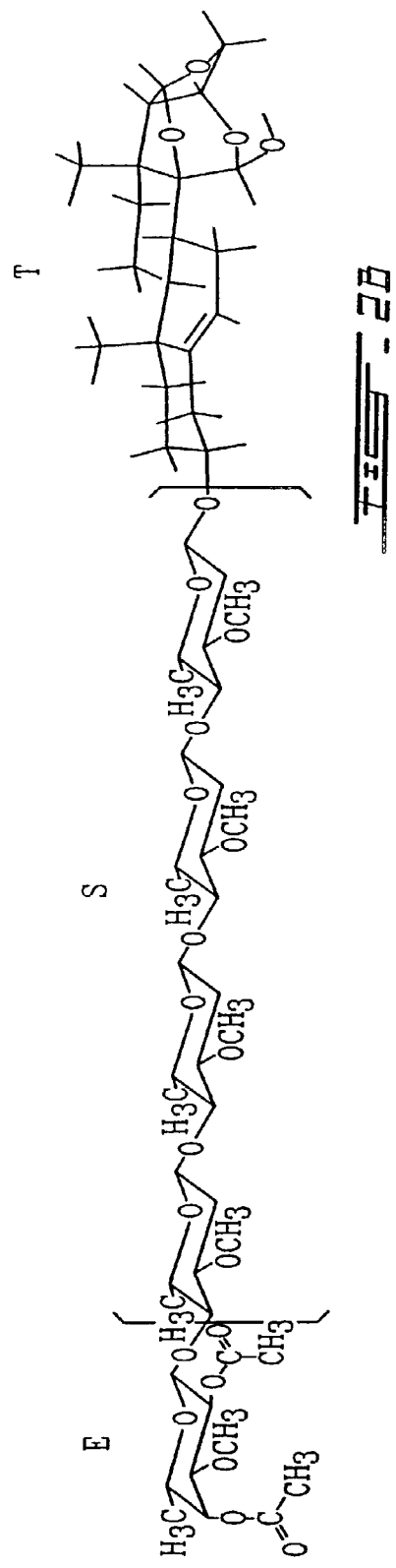

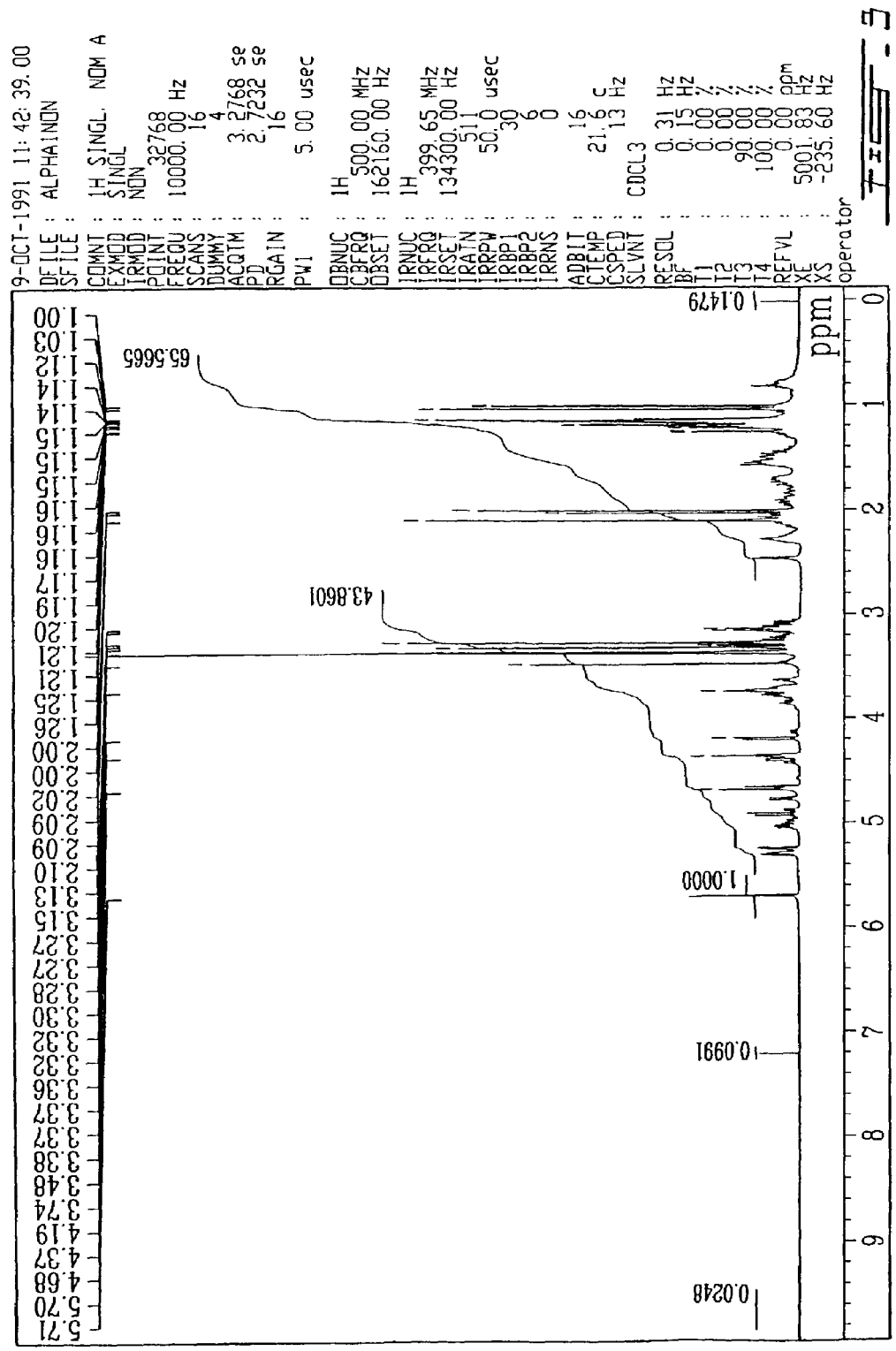

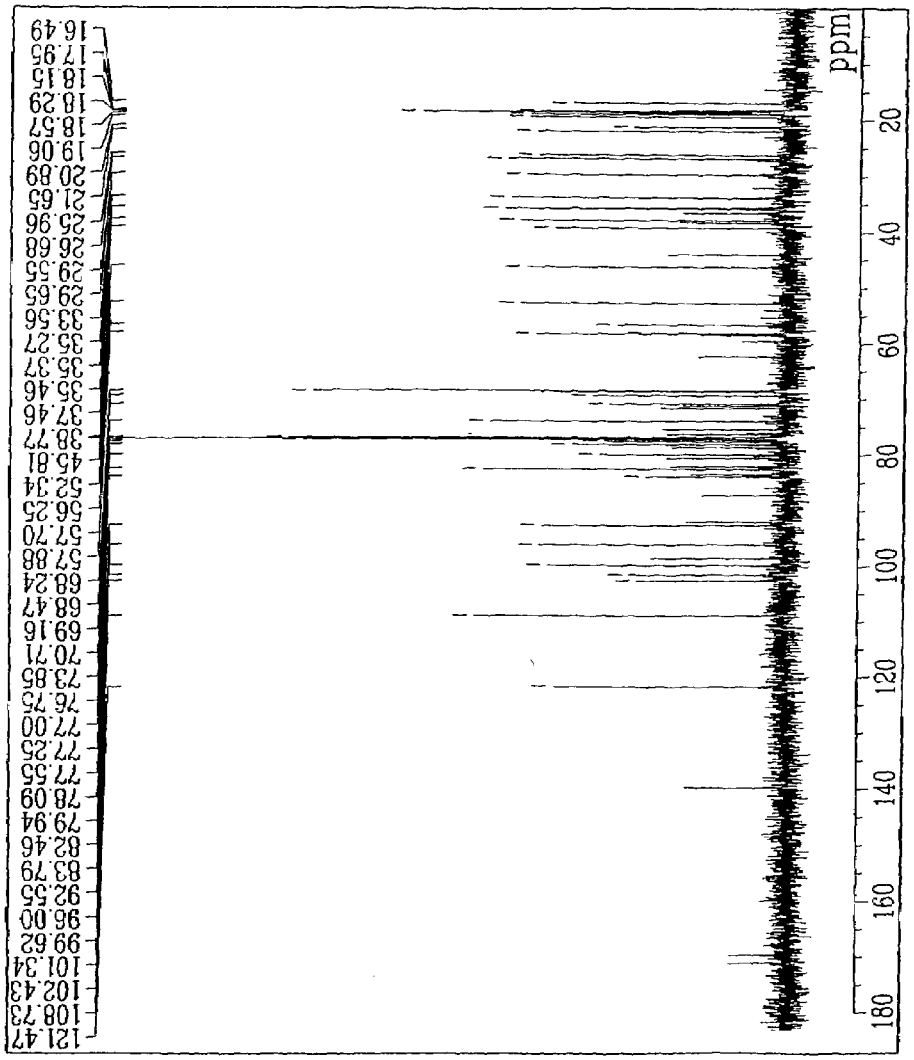

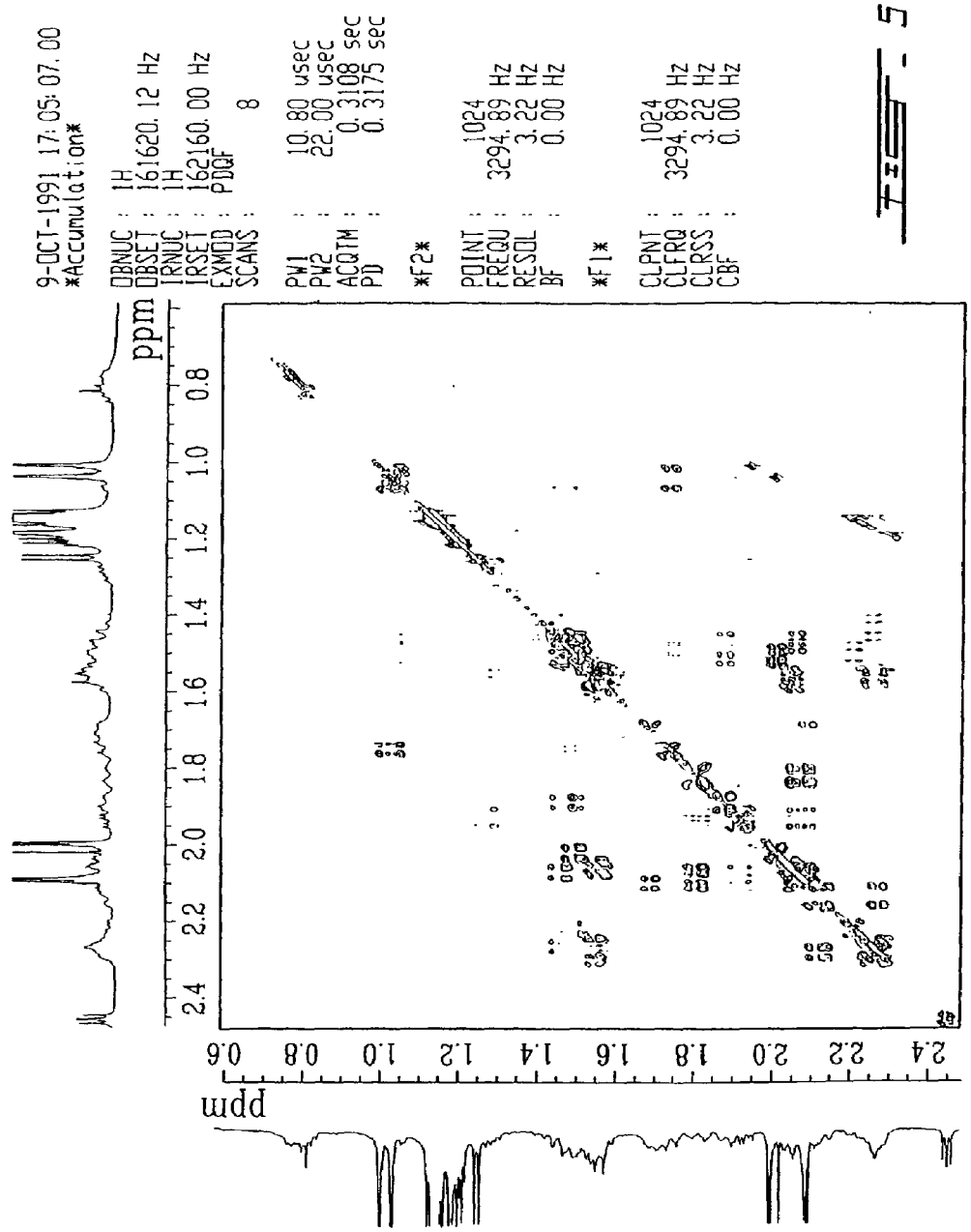

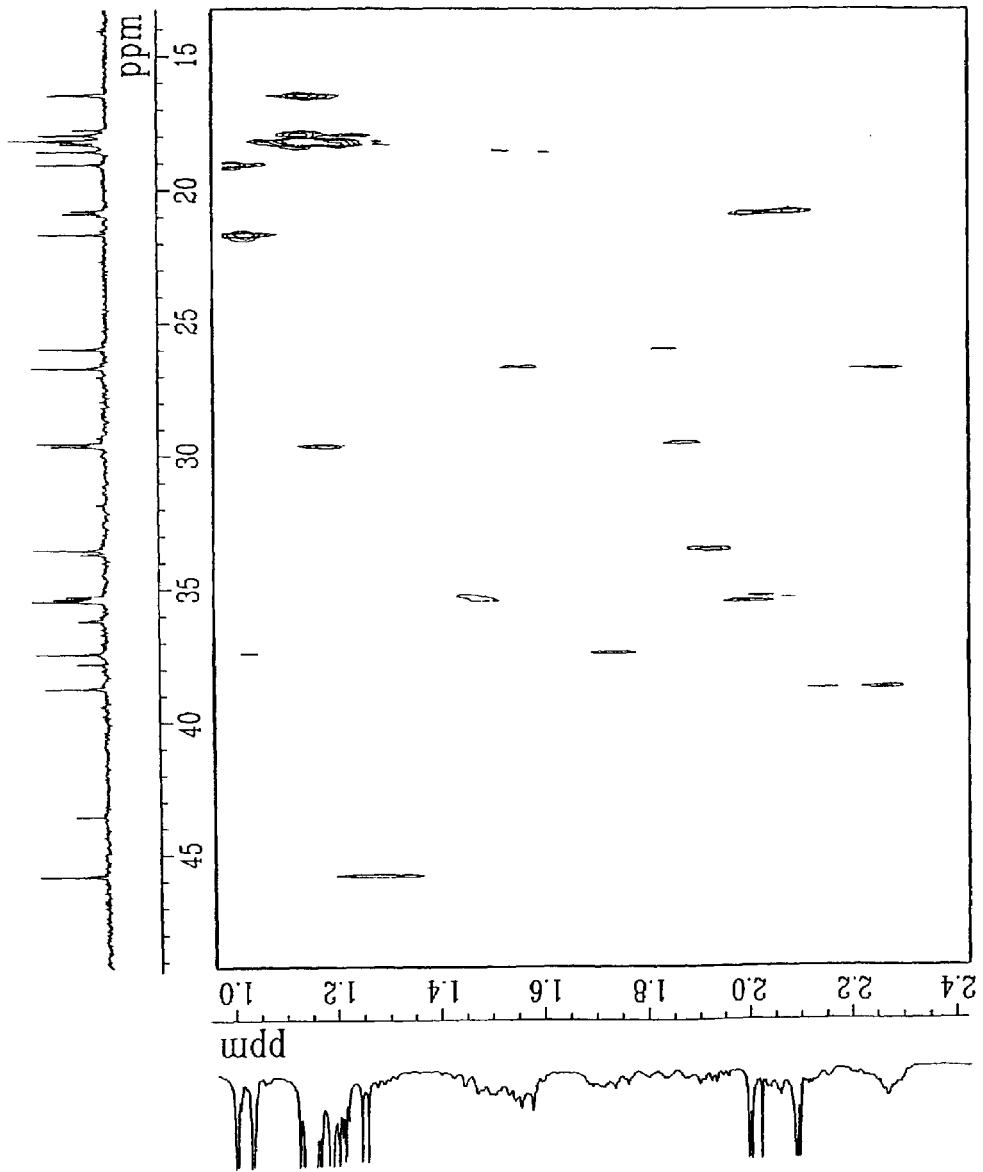

Peak 1. Solvent
Peak 2. MV-8608
Column Temperature 25°C
Chromatogram in HPLC (Beckmann)
Refractive Index Detector
Stationary phase → água/metanol Peak 1. Solvent
Peak 2. MV-8612
Column Temperature   25°C
Chromatogram in HPLC (Beckmann)
Refractive Index Detector
Stationary phase → água/metanol Chromatography →Shimadzu CG – 14A
Sample →MV 8608
Column temperature →80°C →250°C
Detector temperature →290°C
Injector temperature →250°C
Gradient temperature →10°C/min
Column LM-1
Solvent →acetone
Peak 1 →solvent
Peak 2 →MV 8608

Chromatography → Shimadzu CG – 14A
Sample → illustrol
Column temperature → 80°C → 250°C
Detector temperature → 290°C
Injector temperature → 250°C
Gradient temperature → 10°C/min
Column LM-1
Solvent → acetone/CHCl$_3$
Peak 1 → solvent
Peak 2 → solvent
Peak 3 → illustrol

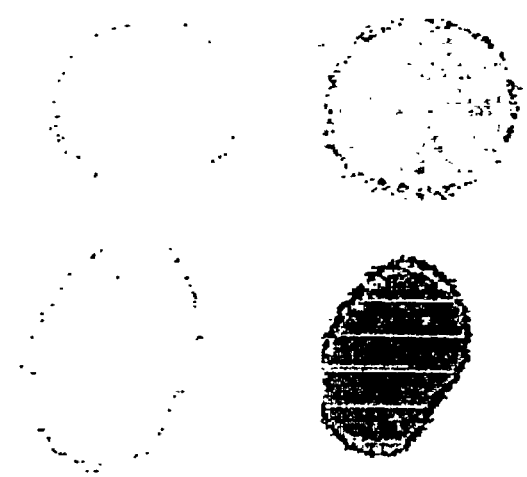  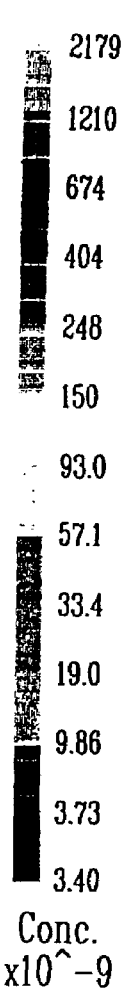
CONTROL     KCl 4 min     MV8608 5 min
HUMAN HEART
  
CONTROL     KCl 3 min     MV8608 1 min
Conc. $\times 10^{-9}$
FIG. 15

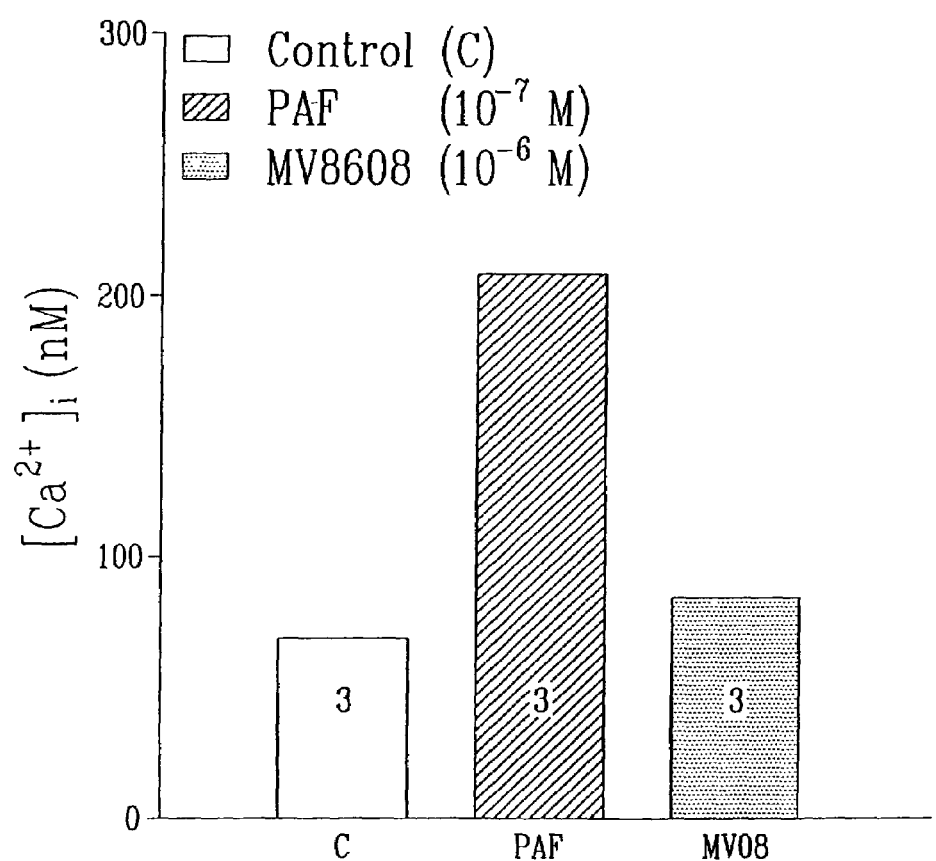
FIG_23

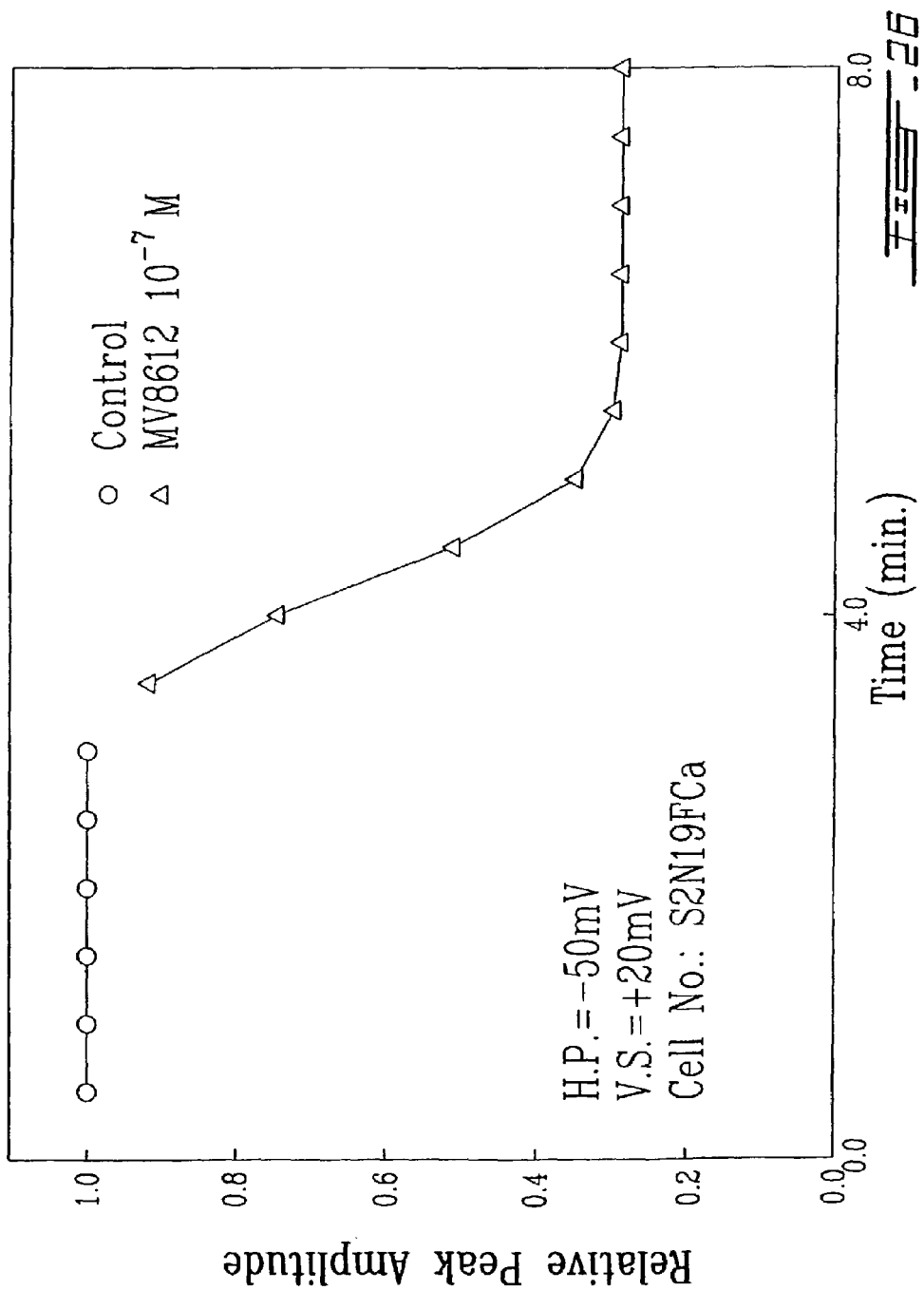

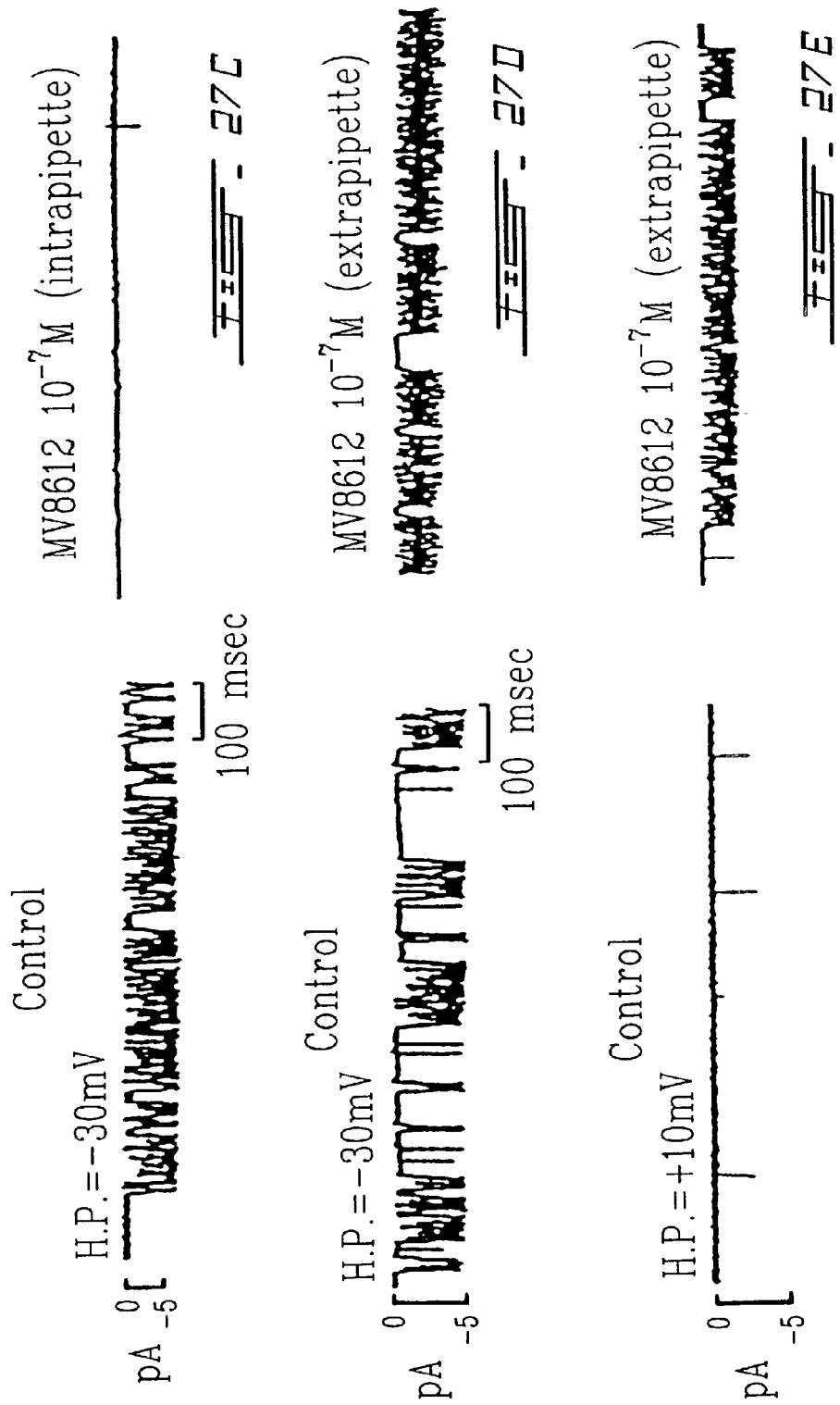

$* \ p < 0.05 \quad *** \ p < 0.001$

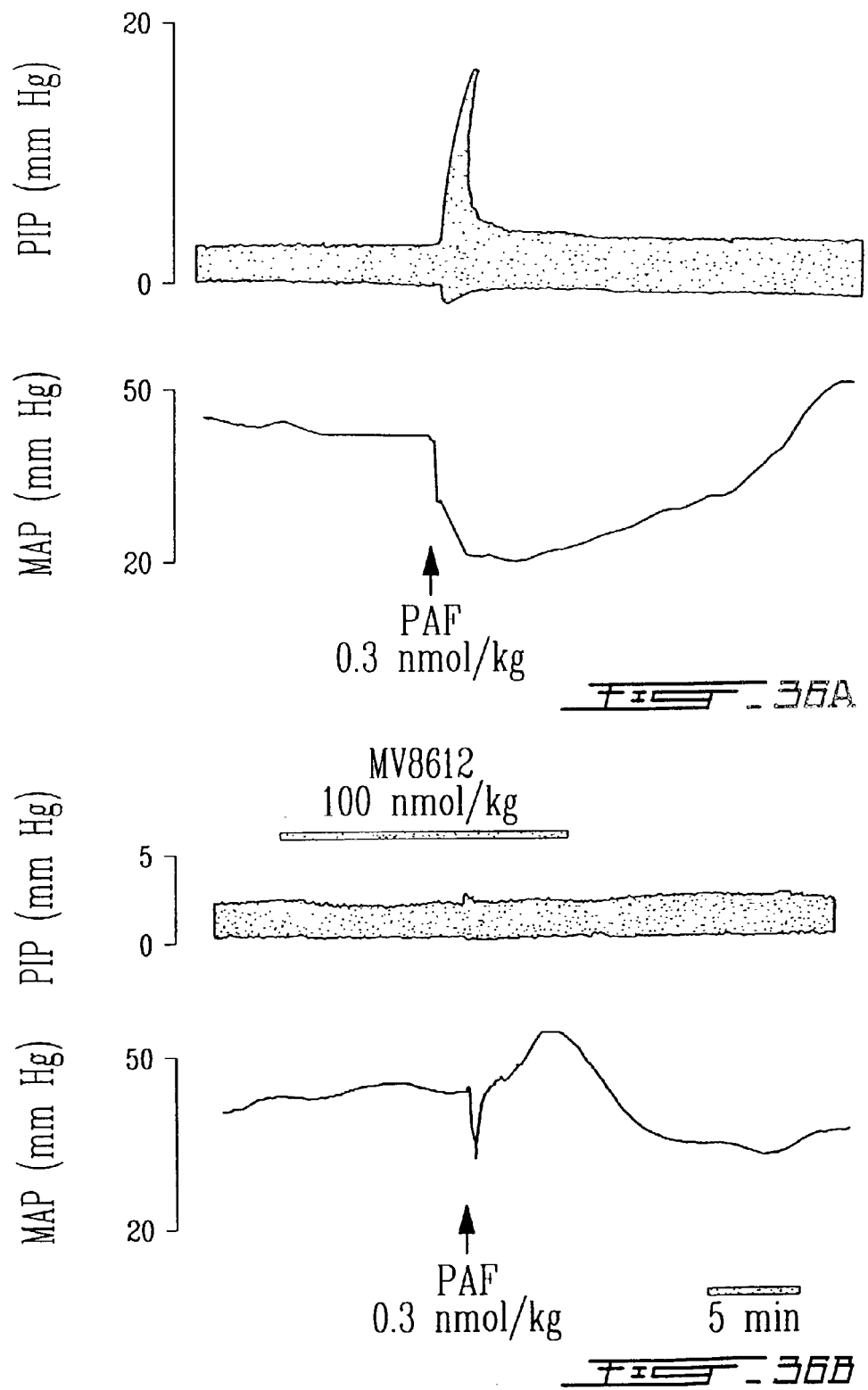

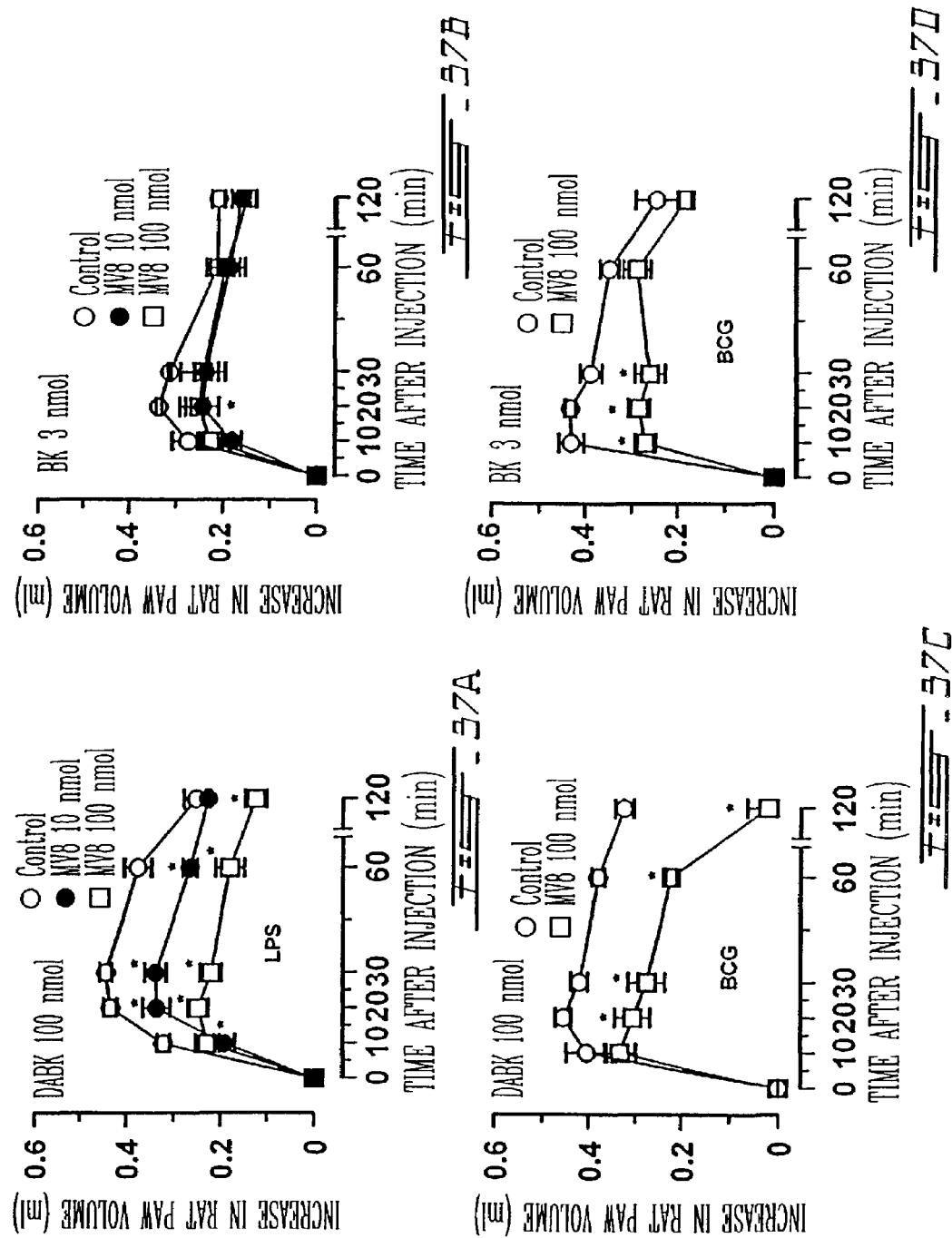

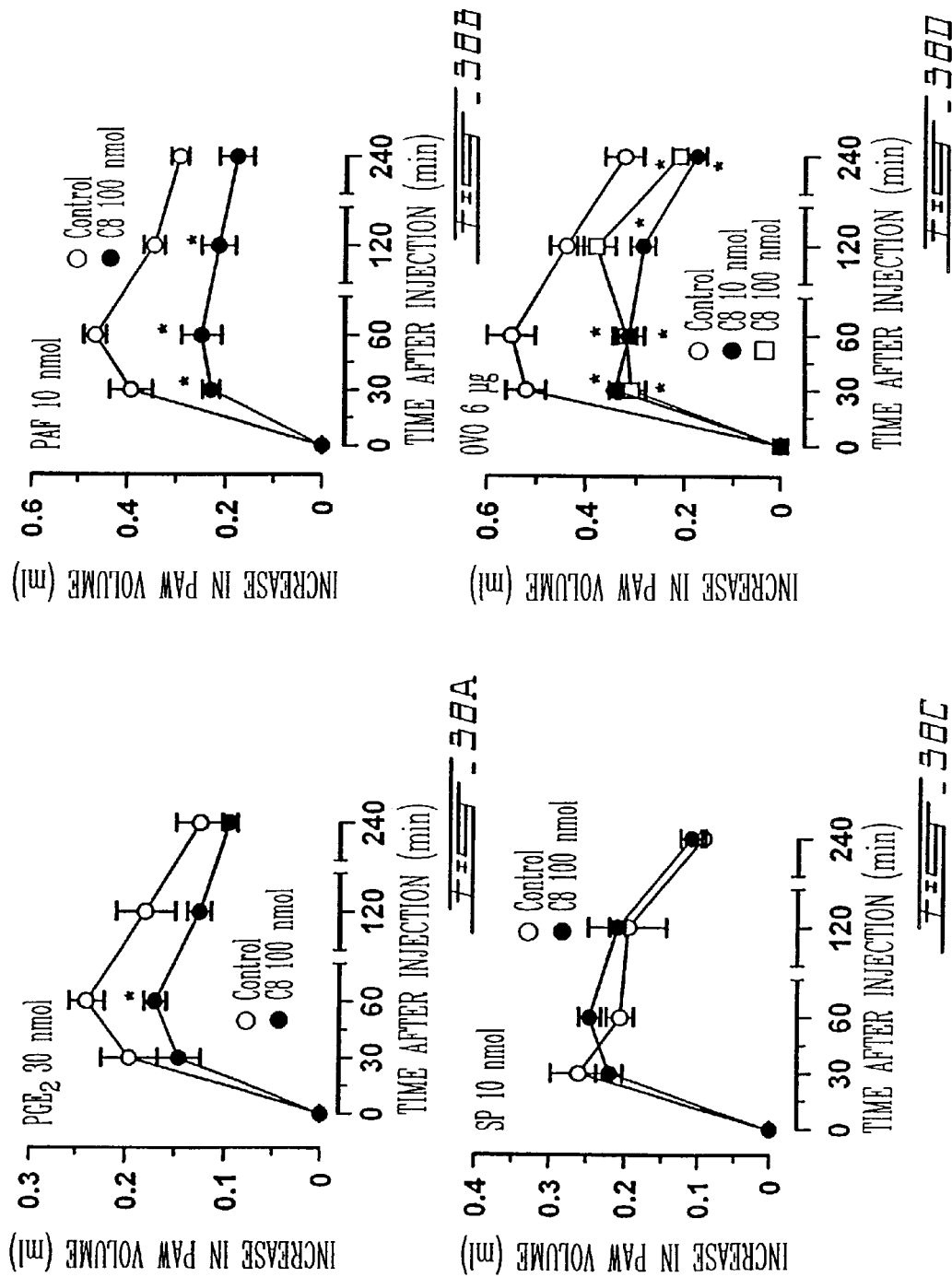

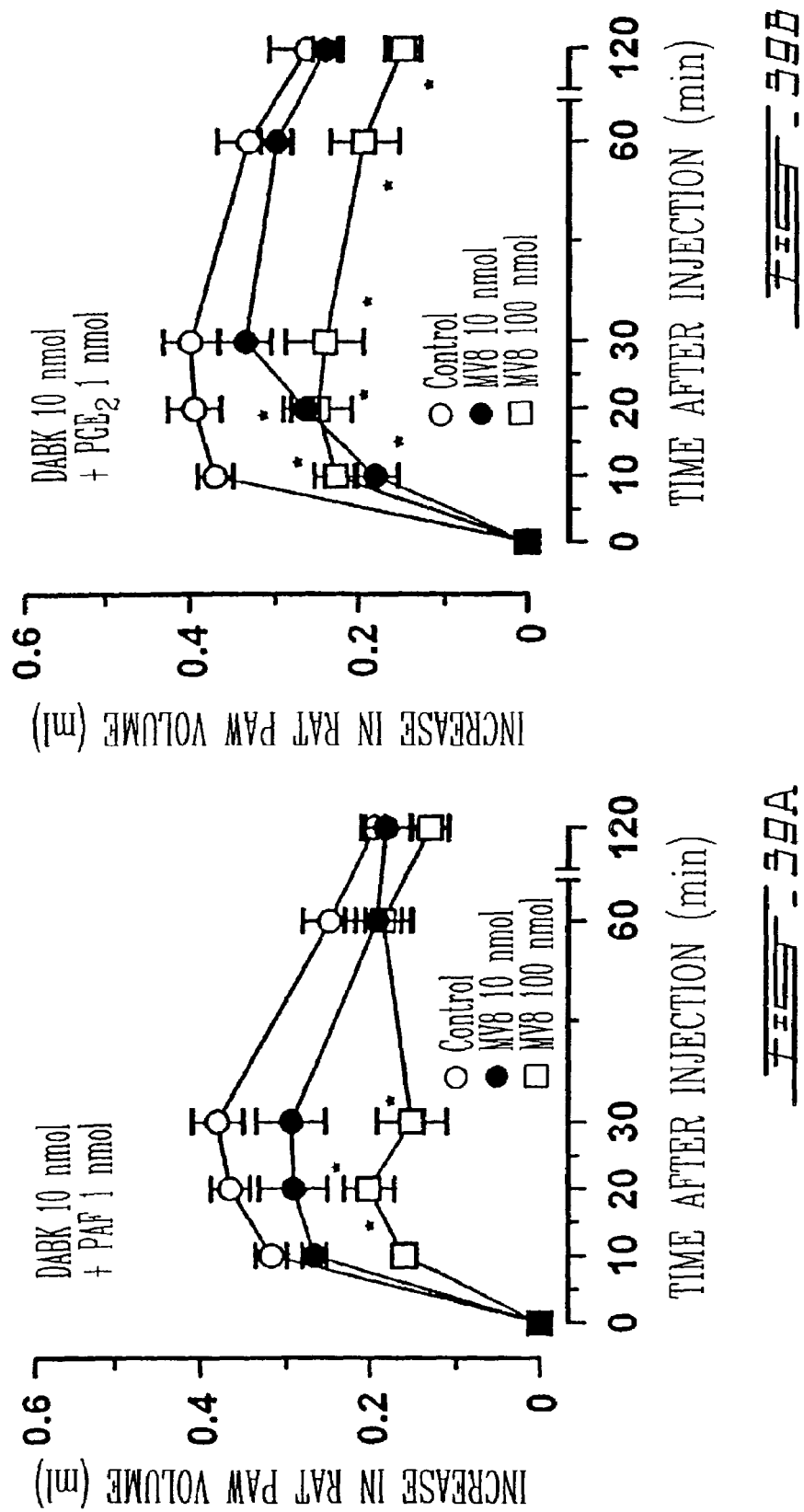

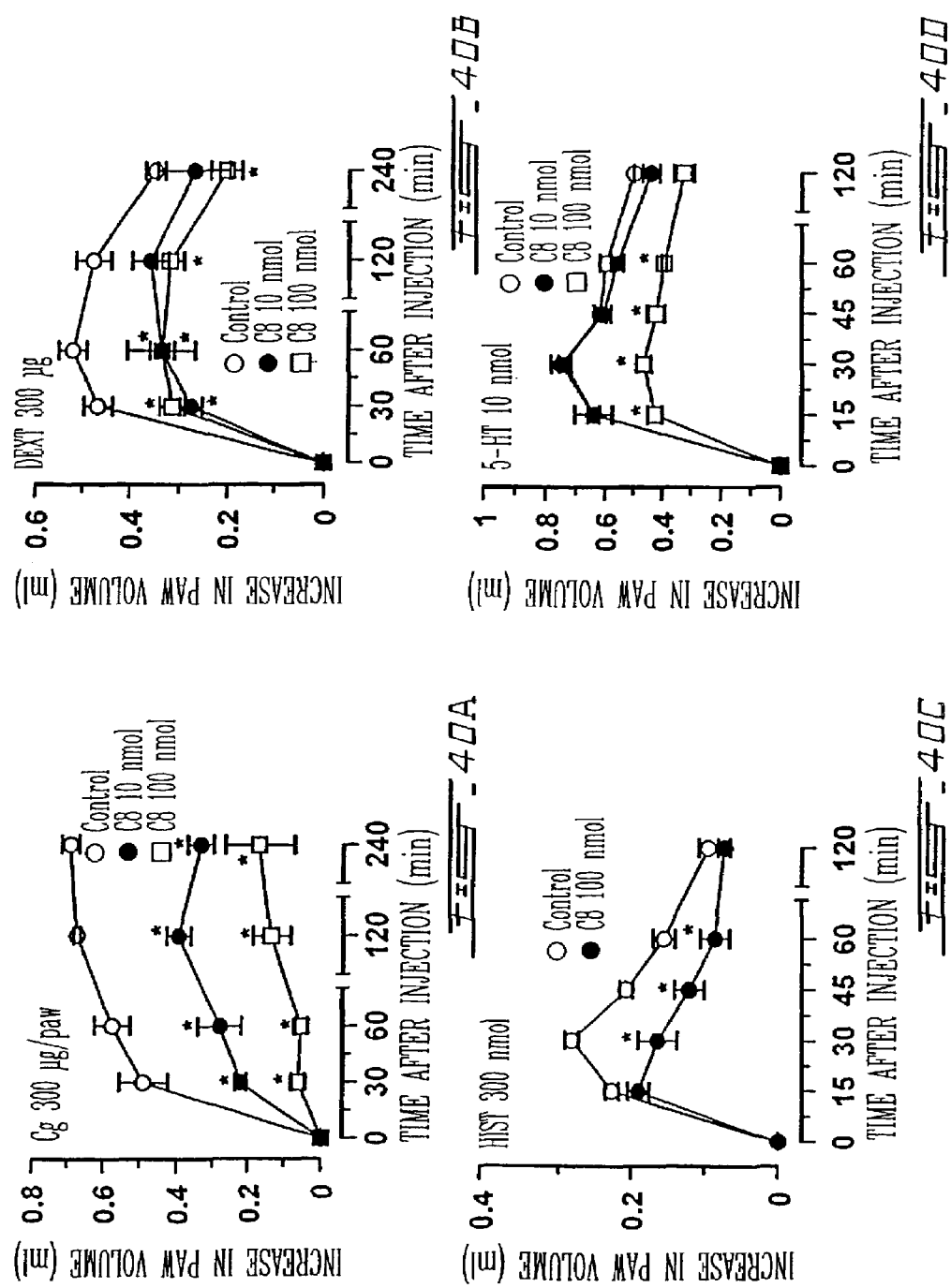

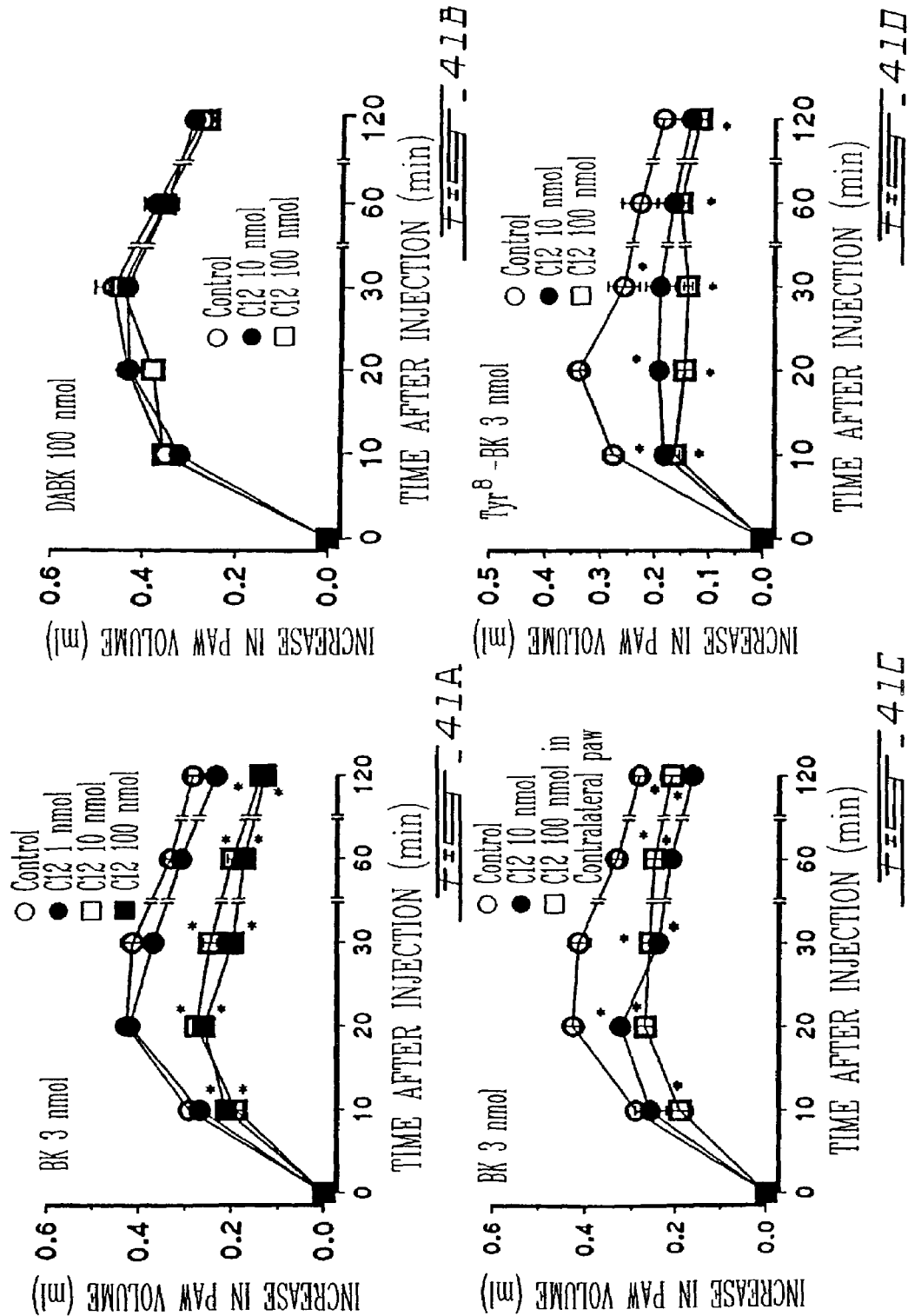

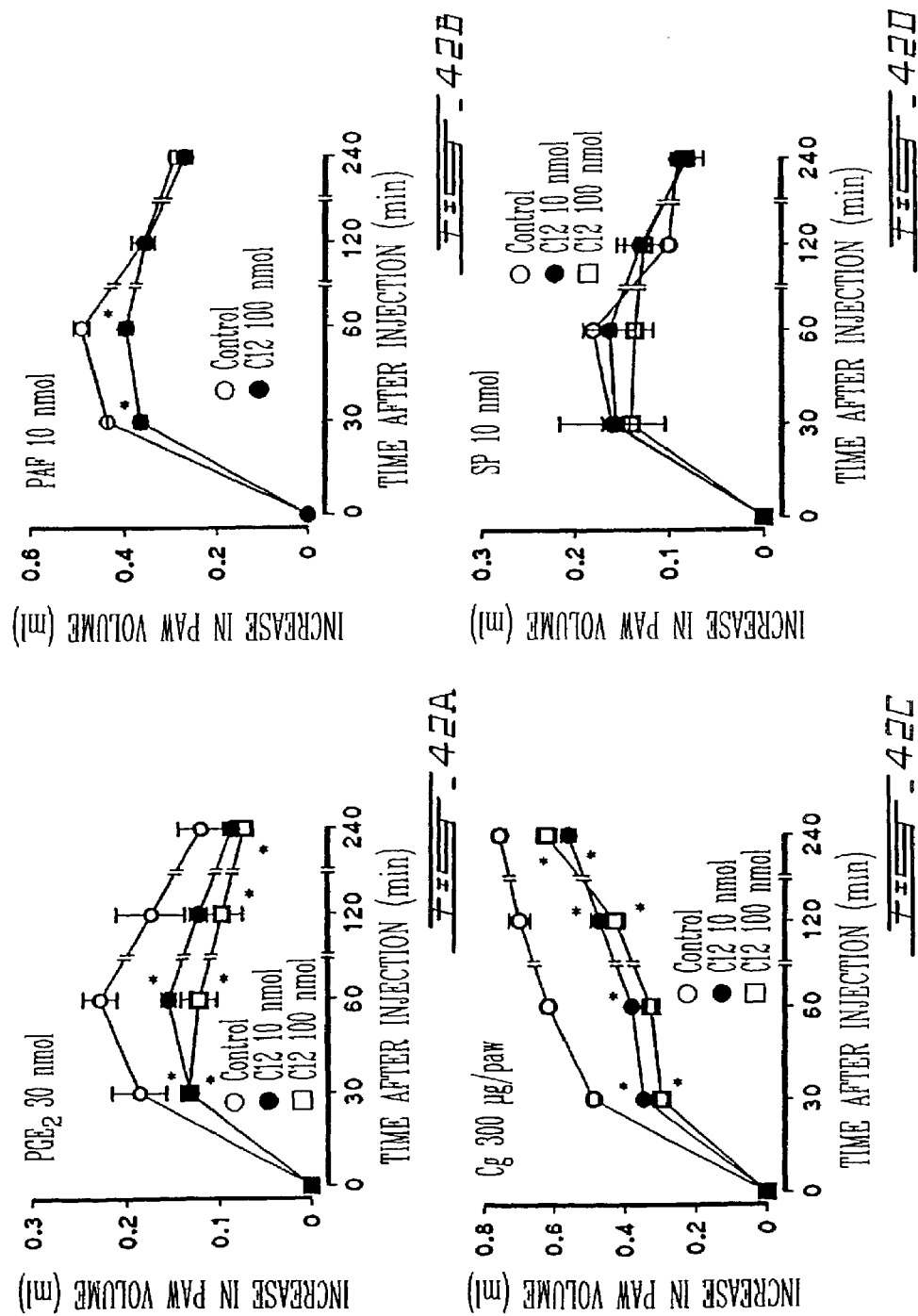

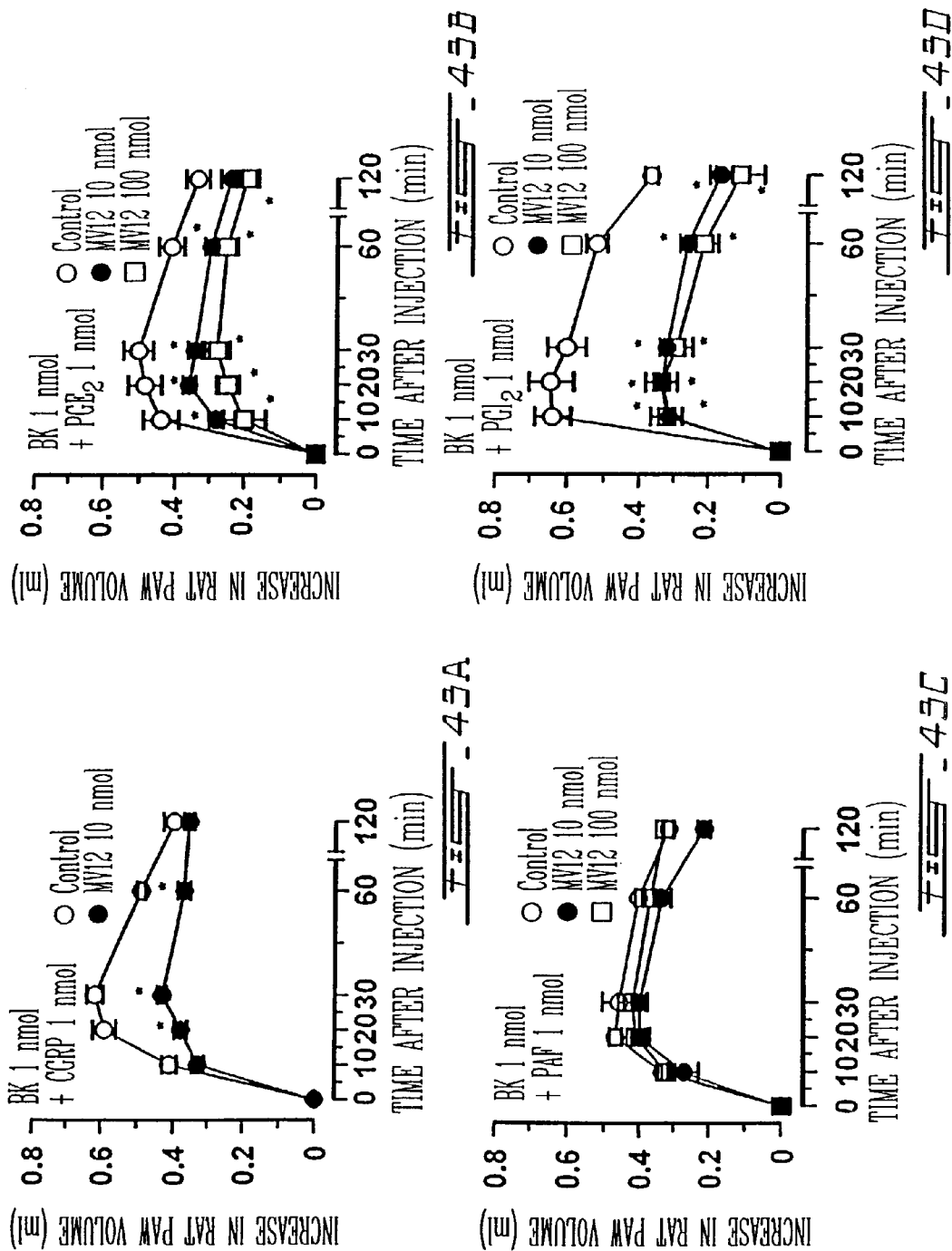

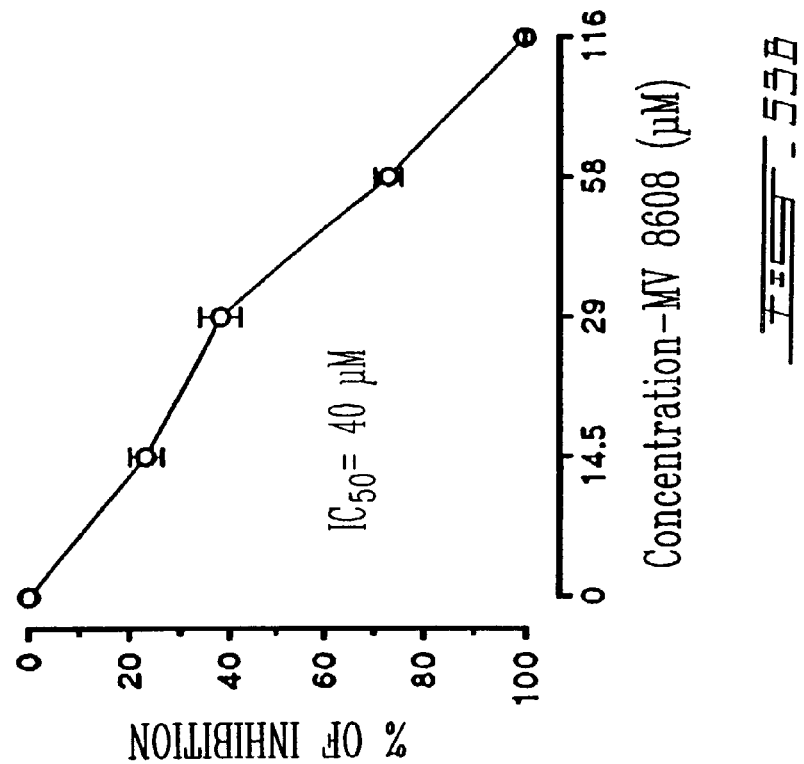
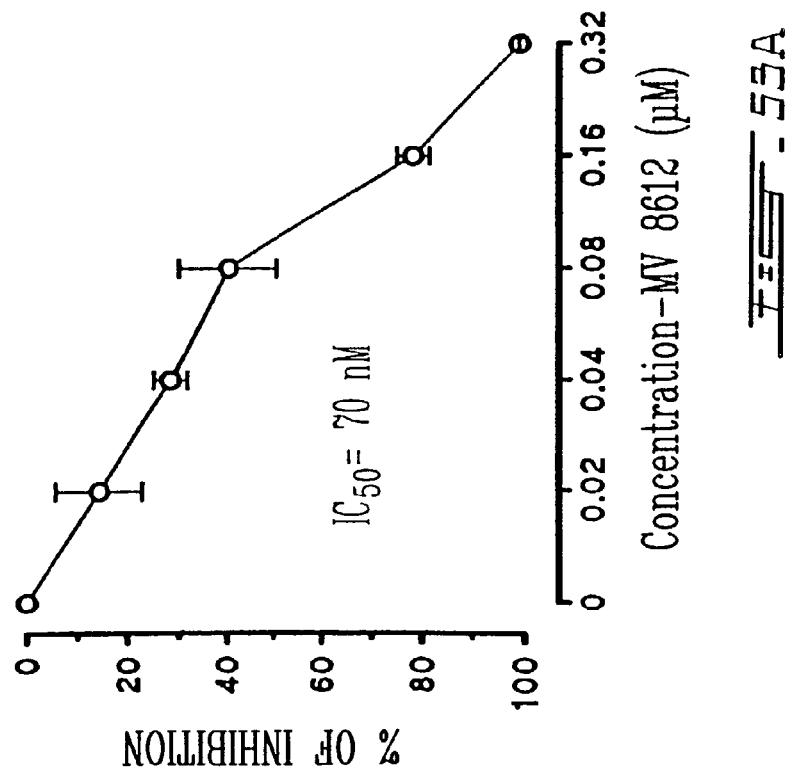
FIG. 53B
FIG. 53A

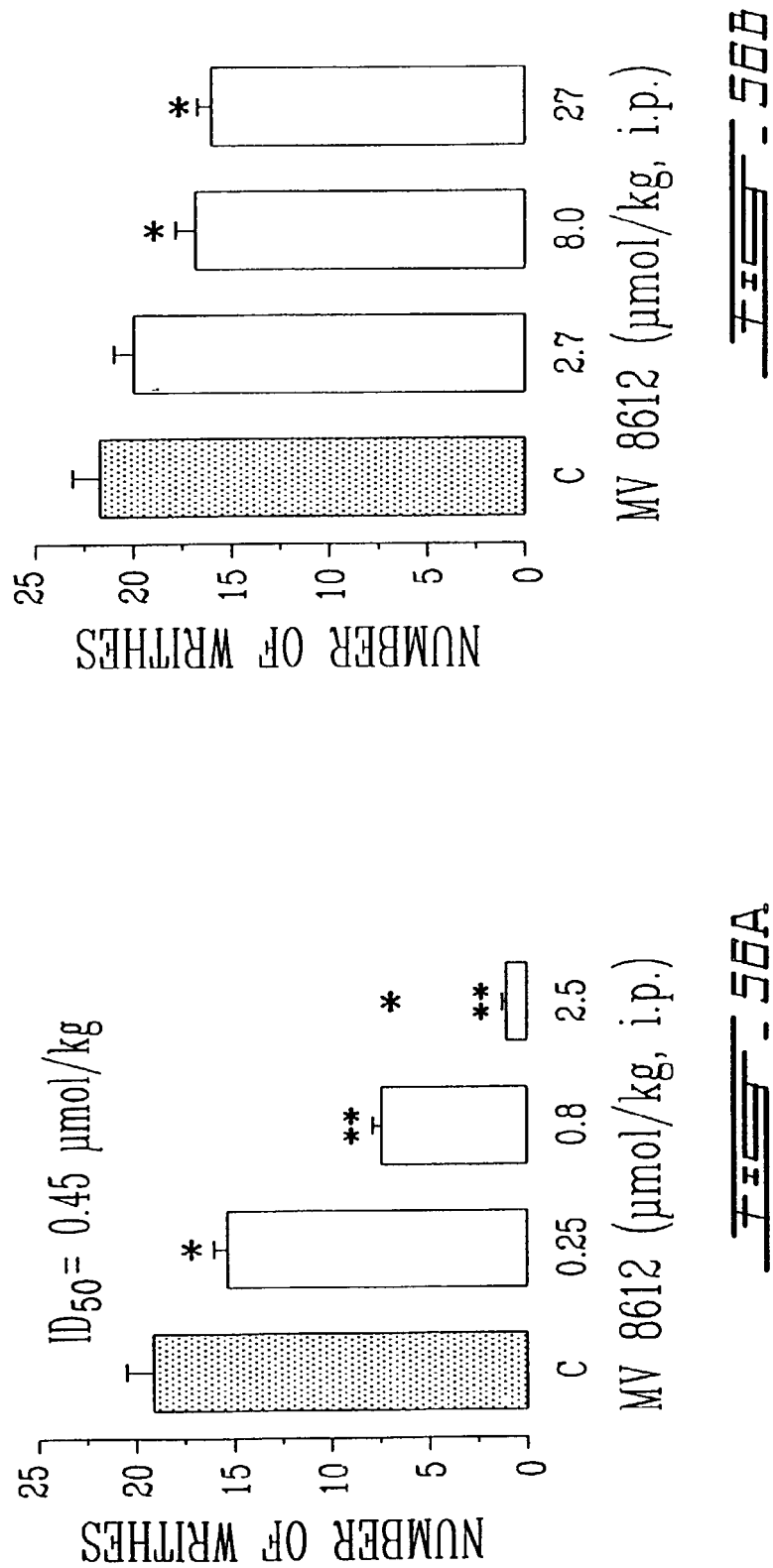

SPECIFIC STEADY-STATE R-TYPE $Ca^{2+}$ CHANNEL BLOCKERS AND USE THEREOF

This application is a continuation of application Ser. No. 09/509,462, filed Jul. 20, 2000, now abandoned which application(s) are incorporated herein by reference.

FIELD OF THE INVENTION

The present invention relates to $Ca^{2+}$ channel blockers and more particularly to the R-type $Ca^{2+}$ channel blockers. More specifically, the invention relates to $Ca^{2+}$ channel blockers activity of *Mandevilla velutina* and *Mandevilla illustris*. The present invention further concerns saponin-like compounds isolated from *Mandevilla* species. The present invention also relates to the treatment of several pathologies that involve the nifedipine-insensitive but isradipine sensitive steady-state R-type $Ca^{2+}$ channel and the use of steady-state R-type $Ca^{2+}$ channel blockers in the treatment of these pathologies.

BACKGROUND OF THE INVENTION

Sustained increase of intracellular $Ca^{2+}$ or sustained $Ca^{2+}$ overload (cytosolic, nuclear and mitochondrial) is known to be associated with many abnormal cell function including hypertension, artherosclerosis, hyperinsulinemia, diabetes Melitus type II, abnormal cell proliferation, cell—cell interactions, necrosis, ischemia/reperfusion, arrythmias, platelet activation and aggregation as well as inflammation and asthma (Bkaily, 1994, Medical Intelligence Unit, CRC Press, Austin; Bkaily and Jacques, 1994, Kluwer Academic Publ., Boston; Bkaily et al., 1994, Kluwer Academic Publ., Boston; Bkaily et al., 1997, Can. J. Physiol. Pharmacol. 75:652–666; Bkaily et al., 1997, Mol. Cell. Biochem. 172: 171–194; Bkaily et al., 1997b, Drug Devel. Res. 42:211–222; Sowers et al., 1993, Am. J. Hypert. 6:302–307; 1994; Hurwitz et al., 1991, CRC Press, Boca Raton, Ann Arbor; Nagano et al., 1992, Kluwer Academic Publ., Boston; Anand et al., 1989, Kluwer Academic Publ. Boston; Dhalla et al., 1996, Kluwer Academic Publ. Boston; Karmazyn, 1996, Birkhauser Verlag. Basel, Boston; Curtis, 1993, Academic Press. London, San Diego; De Brum et al., 1996, Br. J. Pharmacol. 118:1597–1604; Foreman, 1993, Academic Press, London, San Diego; Furberg et al., 1993, Am. J. Hypert. 6:24S–29S; Holgate et al., 1993, Academic Press, London, Boston; Jacobs et al., 1993, Hypertension 21:308–314; Johnson et al., 1993, J. Clinic. Pharmacol. 35:484–492; Levy et al., 1994, Am. J. Med. 96:260–273; Raman et al., 1995, Am. J. Hypert. 8:197–200; Sperelakis et al., 1984, Martinus Nijhoff Publ. Boston; Standley et al., 1993; Wray et al., 1989, The New York Academy of Sciences, New York. Vol. 560). A wide variety of drugs has been tested against different types of $Ca^{2+}$ channels (P, N, T and L) and the development of $Ca^{2+}$ blockers has been concentrated on the L-type $Ca^{2+}$ channel, which has never been shown to undergo any abnormal function in many diseases implicating sustained increase of intracellular $Ca^{2+}$ ($[Ca]_i$) or $Ca^{2+}$ overload. Also, these drugs with the exception of isradipine (PN200-110, Lomir/Dynacirc), failed to block or prevent the sustained increase of $[Ca]_i$, $Ca^{2+}$ overload and necrosis. Recently, the presence of a steady-state nifedipine (L-type blocker)-insensitive but isradipine sensitive (dual L and R-type blocker) R-type (resting-type) $Ca^{2+}$ channel that is voltage and Ligand-G protein-dependent has been reported (Bkaily et al., 1991, Elsevier, New York; Bkaily et al., 1992a, Am. J. Physiol. 262:H463–471; 1993, Br. J. Pharmacol. 110:519–520; 1993a, J. Mol. Cell. Cardiol. 25:1305–1316; 1995, J. Cardiovascul. Pharmacol. 26:303–306; 1996, Mol. Cell. Biochem. 154:113–121; 1997, Drug Develop. Res. 42:211–222; 1997a, Mol. Cell. Biochem. 172:171–194; 1997b, Can. J. Physiol. Pharmacol. 75:652–666; 1997d, Mol. Cell. Biochem. 170:1–8; 1997d, Mol. Cell. Biochem. 176:199–204; 1998, Mol. Cell. Biochem., 183:39–47; Bkaily, 1994a, In: Ionic channels in vascular smooth muscle. G. Bkaily edt. Molecular Biology Intelligence Unit, R.G. Lands Co. Austin.). This channel was responsible for maintaining the resting cytosolic and nuclear $Ca^{2+}$ levels and its overstimulation by sustained depolarization or by permanent presence of some hormones such as insulin, ET-1, PAF, TNFα, PDGF, Bradykinin, or IL-1 induced sustained increase of $[Ca]_c$ and $[Ca]_n$. (Bkaily et al., 1991, Elsevier, New York; 1993, supra; 1995, supra; 1996, supra, 1997a, supra; 1997b, supra; 1997c, supra; 1997d, supra; 1998, supra; Bkaily, 1994a, supra; Bkaily, 1994b, In: Membrane physiopathology. G. Bkaily edt. Kluwer Acad. Publ. Boston; Taoudi et al., 1995, J. Cardiovasc Pharmacol. 26:300–302). The important features that distinguish this channel from other $Ca^{2+}$ channels are the sustained activity (as long as a depolarization or the pharmacological and physiological agonist is present) and the large number of disparate agonists that indirectly (via receptor-G proteins coupling) stimulate the channel.

Several reviews described the presence of various types of voltage-dependent $Ca^{2+}$ channels in many cell types including heart, vascular smooth muscle (VSM) and vascular endothelial (VE) cells (Godfraind and Govoni, 1995; Bkaily, 1994b, supra; Orallo, 1996, Bkaily et al., 1997a, supra). Among these different types of $Ca^{2+}$ channels, the resting membrane potential steady-state voltage-dependent R-type (for resting) $Ca^{2+}$ channel was first reported by the group of Bkaily et al. (Bkaily et al., 1991, supra; 1992, supra; Bkaily, 1994, supra). Later, the group of Tsien (Zhang et al., 1993, Neuropharmacol 32:1075–1088; Randall et al., 1997, Neuropharmacol 36:879–893) described a dihydropyridine resistant type $Ca^{2+}$ channel also named R-type (for resistant).

The steady-state R-type $Ca^{2+}$ channel in human VSM and VE cells was reported to possess a nearly 24 pS single channel conductance (in 110 mM $Ca^{2+}$) (Bkaily et al., 1997a, supra). This type of channel was shown to be responsible for determining, under normal conditions, the resting tension of VSM cells and secretions by VE cells (Bkaily et al., 1991, supra; Bkaily et al., 1992, supra; Bkaily et al., 1993, supra; Bkaily et al., 1995, supra; Bkaily et al., 1996; Bkaily et al., 1997a; Bkaily et al., 1997b; Claing et al., 1994, Br. J. Pharmacol. 1:1202–1208; Taoudi-Benchekroun et al., 1995, J. Cardiovasc. Pharmacol. 26:300–302). This type of $Ca^{2+}$ channel is known to be insensitive to nifedipine and inorganic L-type $Ca^{2+}$ channel blockers such as cobalt, cadmium and $Mn^{2+}$ and the T-type $Ca^{2+}$ blocker, nickel (Bkaily, 1994, supra). However, it is blocked by PN200-110 (isradipine) which is also known to block the L-type $Ca^{2+}$ channel (Bkaily et al., 1992, supra; Bkaily et al., 1997a, supra). Unlike T and L-type $Ca^{2+}$ channels, the R-type $Ca^{2+}$ channel was not regulated by second messengers such as cAMP, cGMP and protein kinase C and neither by ATP (Bkaily, 1994, supra). This type of channel was reported to be indirectly stimulated by insulin, PAF, ET-1 and bradykinin via stimulation of a PTX and CTX sensitive G-protein(s) (Bkaily, 1994a, supra; 1991, supra; 1992, supra; 1995; 1996, supra; 1997a, supra; 1997b, supra; 1997c, supra; 1998, supra) and to contribute to a sustained elevation of cytosolic ($[Ca]_c$) and nuclear ($[Ca]_n$) $Ca^{2+}$. These indirect R-type $Ca^{2+}$ channel stimulators such as PAF induced elevation of $[Ca]_c$ and $[Ca]_n$ by increasing the probability of opening of the channel, and thus allowing longer influx of $Ca^{2+}$ through the sarcolemmal membrane (Bkaily et al., 1997a, supra).

Since PN200-110 was found to be the only available compound to depress the R-type $Ca^{2+}$ channel and since this $Ca^{2+}$ blocker is known to affect other types of $Ca^{2+}$ channels, there remains a need to develop specific and potent steady-state R-type $Ca^{2+}$ channel blockers.

The steady-state R-type $Ca^{2+}$ channels are distributed in a non-homogenous fashion, similarly to some other receptors. This type of channel seems to have no inactivation gate and it is highly selective for $Ca^{2+}$ ions. The R-type $Ca^{2+}$ channel is highly voltage-dependent but could be stimulated by receptors whose activation is coupled to a specific PTX and CTX-sensitive G-protein(s) (Bkaily et al., 1998, supra). Thus, if the R-type $Ca^{2+}$ channel is fully activated via a receptor dependent pathway, it may appear as a receptor operated $Ca^{2+}$ channel. Moreover, if the R-type channel is fully activated by voltage, receptor stimulation does not further modulate its function and appears as a pure voltage-dependent channel (Bkaily, 1994, supra; 1997a, supra; 1997c, supra). Since T- and L-type $Ca^{2+}$ channels are rapidly inactivated during sustained voltage or pharmacological stimulation, these types of channels can only contribute to the inset stimulation. However, the R-type $Ca^{2+}$ channel will contribute to both inset and sustained elevation of cytosolic and nuclear free $Ca^{2+}$, seen in normal and pathological conditions, depending on the function of the studied cell type. Hence, this type of channel, under normal physiological situations contributes to the resting $Ca^{2+}$ influx responsible for determining the resting cytosolic and nuclear $Ca^{2+}$ that modulate resting tension, secretion, protein synthesis and mitosis. In working muscle cells, such as heart cells, the normal physiological function of this channel at the sarcolemmal membrane level, is to maintain normal resting cytosolic $Ca^{2+}$ level. However, at the nuclear membrane levels, this channel seems to be implicated in maintaining normal resting nucleoplasmic $Ca^{2+}$ levels (near 300 nM) (Bkaily et al., 1997a, supra; 1997b, supra).

During excitation-contraction coupling, the R-type $Ca^{2+}$ channel is implicated in regulating $Ca^{2+}$ wave propagation initiated, by $Ca^{2+}$ influx through the opening of the T- and L-type $Ca^{2+}$ channels and the subsequent large $Ca^{2+}$ release from the SR by attenuating the cytosolic $Ca^{2+}$ wave amplitude, by allowing $Ca^{2+}$ influx through the nuclear membrane and thus permitting a smooth contraction and relaxation. The subsequent release of the uptaken $Ca^{2+}$ permits the maintainance of $Ca^{2+}$ waves and slow relaxation and propagation of the waves to neighboring cells, most likely through gap-junctions and in this manner, allowing synchronization of contraction of ventricular cells (Lopez et al., 1995, Biochem Biophys Res Commun 214:781–787; Bkaily et al., 1996, supra; 1997a, supra). The fact that cytosolic $Ca^{2+}$ waves cannot be completely absorbed by the nucleus is due to the maximum $Ca^{2+}$ buffering capacity of the nucleus which is shielded from variations in cytoplasmic $Ca^{2+}$, perhaps by gating mechanisms in the perinuclear envelope once its maximum capacity is reached (Burnier et al., 1994, Am J Physiol 266:C1118–C1127; Bkaily, 1994, supra; 1996, supra; 1997a, supra, 1997b, supra).

Recent published results also showed that in secretory cells such as VE and VSM cells, tonic secretion or contraction is mainly, if not only due to the activation of sarcolemmal R-type $Ca^{2+}$ channels. It was further shown that in VSM and excitable cells (VE cells do not possess T- or L-type $Ca^{2+}$ channels) the T and/or the L-type $Ca^{2+}$ channel activation, serves as a turbo $Ca^{2+}$ influx mechanism in order to rapidly bring the $Ca^{2+}$ level up to the threshold level for contractile elements and to pre-overload the nucleoplasm with $Ca^{2+}$, enabling cytosolic accumulation of $Ca^{2+}$ and maintain tension. Thus, overstimulation of the R-type $Ca^{2+}$ channels may highly contribute to cytosolic and nuclear $Ca^{2+}$ accumulation that could be considered in many cases as the first and in all cases the final pathological consequence of several diseases such as hypertension, atherosclerosis, abnormal conduction, arythmias, fibrillation, and of remodelling, proliferation and apoptosis. For these reasons, targeting the sarcolemmal nuclear membrane R-type $Ca^{2+}$ channels with a selective depressor blocker, or targeting receptors that indirectly modulate this type of channel at the sarcolemmal, or mainly at the nuclear membrane level, would constitute without any doubt, a major therapeutical pathway for a new generation of $Ca^{2+}$ channel and $Ca^{2+}$ entry blockers.

For example, the sustained activation of the R-type channel by insulin may explain in part "syndrome X", the hypertension, hyperglycemia, dyslipidemia, vascular smooth muscle proliferation and end organ damage associated with non-insulin-dependent diabetes mellitus (NIDDM) and obesity-induced hypertension. Also, the sustained increase in $[Ca]_c$ and mainly $[Ca]_n$ mediated by the stimulation of the R-type $Ca^{2+}$ channel could contribute to the expression of oncogenes and to the proliferation of malignant cells as well as to stimulation of TNFα; PAF which would lead to septic shock. The finding that Lomir/Dynacirc (but none of the other L-type $Ca^{2+}$ antagonists) is unique in depressing the overstimulation of the R-type $Ca^{2+}$ channel permits the identification and characterization of this type of $Ca^{2+}$ channel. Non published results in two human osteoblast cancer lines (MG63 and FAOS-2) clearly showed that Lomir/Dynacirc ($10^{-8}$M) reduced spontaneous cell proliferation and blocked hypertension and ET-1 plasma elevation associated with cyclosporin A treatment in allograft transplant. In contrast, an L-type $Ca^{2+}$ blocker, nifedipine ($10^{-6}$M) had no effect. A role for the R-type $Ca^{2+}$ channel and Lomir/Dynacirc in human cancer is suggested by the above findings and supported by the finding of reduced cancer rates in the Lomir/Dynacirc treated group of the MIDAS study. The identification of a potent and specific antagonists may hold the possibility of a new therapeutic target for novel medications. The novel R-type $Ca^{2+}$ channel may also prove important in dissecting differential signalling pathways in immune cells. The evaluation of these mechanisms leads to R-type blockade as a therapeutic tool for specific intervention in graft rejection, autoimmune diseases, asthma and septic shock.

A recent report in patients with type I and type II Raynaud's phenomenon (pain and numbness in the fingers, which in some subjects can be complicated by skin ulcers) showed that Lomir/Dynacirc significantly reduced the elevated plasma concentration of ET-1 level, frequency, severity, and disabling nature of acute attacks of Raynaud's phenomenon (La Civita et al., 1996, Clinic. Drugs Invest 11:S126–31). The decrease of the elevated ET-1 circulating level by Lomir/Dynacirc is due to the blockade of the R-type $Ca^{2+}$ channel which reverses the sustained increase of $[Ca]_c$ and $[Ca]_n$, thus, reducing the autocrine and self perpetuating secretion of mitogenic factors such as ET-1, PAF and TNFα. A blockade of the elevated autocrine and self perpetuating secretion of mitogenic factors by cancer cells may in turn contribute to reduction and even blockade of expression of oncogenes and proliferation of these cells.

The use of Sandimmune is known to produce potentially serious side effects such as renal impairment and hypertension. These side effects will restrict Sandiummune's use in autoimmune indications such as psoriasis and rheumatoid arthritis. The renal impairment and hypertension are attributable to altered renal hemodynamics induced by Sandimmune. The L-type $Ca^{2+}$-channel blockers have been used successfully to treat hypertension and renal impairment. The benefits of the $Ca^{2+}$-channel blockers have been attributed to their effects on renal hemodynamics specifically dilation of the afferent renal arteriole.

Data indicate that the dual R- and L-type $Ca^{2+}$ channel blocker isradipine (but not a pure L-type blocker) may correct the vasoconstriction at both the afferent and efferent renal arterioles. The advantage of dilation of the afferent and efferent arterioles is a correction of renal blood flow and glomerular filtration without an increase in filtration fraction. Filtration fraction is an indicator of filtration pressure. An increase in filtration pressure could increase the likelihood of developing glomerulonephritis and eventual renal failure.

The potential benefit of blockade of the R-type $Ca^{2+}$ channel by Lomir/Dynacirc on filtration pressure is supported by the existing literature. For example Grossman et al. (1991, Am. J. Cardiol. 68:65–70) in a 3-month study with Lomir/Dynacirc showed that filtration fraction remained constant. The filtration fraction remained constant despite the increase in glomerular filtration rate and renal blood flow. Vascular resistance was also reduced by the 3 month treatment with Lomir/Dynacirc.

A favourable effect on filtration fraction has been corroborated in transplant patients (Berg et al., 1991, Nephrology, Dialysis, Transplantation. 6:725–30). These investigators showed that filtration fraction was reduced by Lomir/Dynacirc while renal blood flow increased.

The R-type $Ca^{2+}$ channel has also been identified and characterised in vascular smooth muscle cells isolated from human renal arteries (Bkaily et al., 1991, supra).

*Mandevilla velutina* is a native Brazilian plant used in folk medicine to treat snake bites and as an anti-inflammatory agent. Some non-peptidic compounds extracted from this plant block bradykinin and related kinins action. It shows potent analgesic and anti-inflammatory activities (Calixto et al., 1987, supra).

Since 1985, Calixto's group has worked on extracts of *Mandevilla velutina* (MV) and claimed that some of the extracts (such as MV8608) had antagonistic properties against the effect of bradykinin (BK). The compound MV8608 has been characterized in 1987 (Calixto et al., Br. J. Pharmacol. 91:199–204). It has been found to be selective in its ability to inhibit the contraction of rat uterus induced by BK. The previous work made by Calixto's group as well as others on extracts of *Mandevilla* species have always focused on compounds which have a presumed action at the BK receptor site.

In a review article published after 1990, Calixto's group (Calixto and Yunes, 1991, Mem. Inst. Oswaldo 86:195–202, supl. 2) mentioned that the compounds MV8608 had a pregnane structure. It is further mentioned that MV8608 is an aglycone compound (without any sugar). No specific structure is shown in this review article concerning MV8612. This review is a compendium of data, characteristics, and properties of MV8608 and MV8612 in numerous systems responding to BK (therefore not limited to the effect of BK on rat uterus). Again, it may be deducted from this publication that the Calixto group of researchers have focused their study on the search of a ligand which is a BK receptor antagonist. MV8612 has been retained as a good candidate because it best corresponds to established receptor classification criteria (a fairly good pA2, competition curve whose slope does not differ from one and selectivity). Of note, Calixto publication (Calixto and Yunes, 1991, supra) does not teach or suggest that MV8612 may have an action which is aimed at the receptor directly. Although on certain systems the effect of MV8612 has been shown to be non-selective, no explanation on this lack of selectivity toward BK has been provided. Therefore, this publication does not teach or suggest any role of MV8608 and MV8612 as calcium channel blockers.

Other compounds isolated from *Mandevilla Pentlandia*, have also claimed an anti-BK activity, (patent application of Proctor and Gamble Co., EP 0/359310). Furthermore, other *Mandevilla* extracts, particularly from *Mandevilla Illustris* have been shown to have physiological antagonist activity against BK. Indeed, all the compounds obtained from *Mandevilla* species are described as compounds having anti-BK activity. Strikingly, all such descriptions fail to teach or mention the specific site of action of these compounds, and while they lack selectivity, they are deemed to be useful for treating pathologies and conditions involving bradykinin (inflammation, smooth muscle contraction, pain, hypotension, etc.).

The art teaches that a non-specific inhibitor of a calcium channel such as isradipine, which has an effect on calcium channel types L and R, reduces or abolishes the effect of hormones like insulin and PAF (platelet-activating factor), ET-1 and BK which effect is absent when using nifedipine (a L-channel blocker). Nevertheless, the art is indicative of the contribution of the R-type calcium channel in the effect of insulin, PAF, ET-1 and BK.

There thus remains a need to assess the specificity of MV8608 and MV8612 by identifying their direct or indirect effects on $Ca^{2+}$ homeostasis. More broadly, there remains a need to verify whether MV8608 and MV8612 are as non-specific as isradipine. More particularly, there remains a need to assess the activity of these compounds on the R-type $Ca^{2+}$ channel, as well as T, L $Ca^{2+}$ channels and the fast $Na^+$ and delayed outward $K^+$ channels.

In spite of the recent discovery of the R-type $Ca^{2+}$ channel, there is a definite need for a new generation of class of drugs to treat overstimulation of R-type $Ca^{2+}$ channel-associated diseases for the following reasons:

1. There is no drug approved for the treatment of diseases or conditions in which a sustained elevation of $[Ca]_c$, $[Ca]_n$ or R-type $Ca^{2+}$ blocking is encountered; and 2. There remains a definite need for the identification of drugs which are more specific, show less side effects and have a wider therapeutic value, for the treatment of hypertension, artherosclerosis, inflammation, septic shock, arthritis, asthma, cancer, pain, diabetes type II and ischemia-reperfusion, hyperventilation and high circulating ET-1 level.

The present invention seeks to meet these and other needs.

SUMMARY OF THE INVENTION

The invention concerns saponin-like compounds isolated from *Mandevilla* species. More specifically, the invention concern saponin-like compounds isolated from *Mandevilla* species which act as specific R-type $Ca^{2+}$ channel blockers.

In a particular embodiment, the present invention relates to R-type $Ca^{2+}$ channel blocker obtained from *Mandevilla* species and more particularly from *Mandevilla Velutina* and

*Mandevilla Illustris*. In a preferred embodiment, the invention relates to specific R-type $Ca^{2+}$ channel blockers MV8608 and MV8612.

The invention in addition relates to pharmaceutical compositions comprising specific R-type $Ca^{2+}$ channel blockers obtained from *Mandevilla* species to treat and/or prevent diseases or conditions associated with a sustained elevation of $[Ca]_c$, $[Ca]_n$, or R-type $Ca^{2+}$ blocking and/or cytosolic and nuclear $Ca^{2+}$ accumulation, together with a suitable pharmaceutical carrier. More specifically, the present invention relates to such pharmaceutical compositions to treat or prevent hypertension, artherosclerosis, hyperinsulinemia, diabetes Melitus type II, abnormal cell proliferation, cell—cell interactions, necrosis, ischemia/reperfusion, arrhythmias, platelet activation and aggregation, inflammation, asthma, abnormal conduction, fibrillation, remodelling, proliferation, antibacterial proliferation, septic shock, apoptosis, hyperglycemia, dyslipidemia, vascular smooth muscle proliferation and end organ damage associated with non-insulin-dependent diabetes mellitus (NIDDM), and obesity-induced hypertension, cancer, renal impairment, renal failure, arthritis pain, hyperventilation, and high circulating ET-1 level.

The invention further relates to a family of R-type $Ca^{2+}$ channel blockers which virtually only affect the overstimulation thereof, without significantly affecting the basal activity thereof.

In addition, the invention relates to a family of specific R-type $Ca^{2+}$ channel blockers which reduce the over-basal frequency of the R-type $Ca^{2+}$ channel.

The invention also relates to methods of preventing or treating a warm blooded animal having a disease or condition demonstrating a sustained elevation of calcium through an effect on a R-type $Ca^{2+}$ channel, comprising an administration of an effective amount of specific R-type $Ca^{2+}$ channel blocker, in accordance with the present invention, together with a pharmaceutically acceptable carrier. The invention also relates to pharmaceutical compositions for such methods of prevention or treatment.

The invention further relates to methods of treatment of a warm blooded animal in need of this treatment comprising an administration of a therapeutically effective amount of a R-type $Ca^{2+}$ channel blocker obtained from *Mandevilla* species, together with a pharmaceutically acceptable carrier. More specifically, the present invention relates to a treatment of a warm blooded animal demonstrating a sustained elevation of $[Ca]_c$, $[Ca]_n$, R-type $Ca^{2+}$ blocking, and/or cytosolic and nuclear $Ca^{2+}$ accumulation, comprising an administration of a therapeutically effective amount of a R-type $Ca^{2+}$ channel blocker obtained from *Mandevilla* species, together with an acceptable pharmaceutical carrier.

Before the present invention, the properties of the MV compounds towards the calcium channel type R disclosed had not been taught or suggested.

Furthermore, before the present invention, it was unknown that in organ transplants, in an animal model such as rabbit, that there is an increase of circulating ET-1 and a decrease of blood flow that were not prevented by cyclosporin-A and by the pure L-type blocker nifedipine. In contrast, the dual R- and L-type $Ca^{2+}$ blocker Lomir/Dynacirc (isradipine or PN200-110), restored ET-1 and blood flow levels in cyclosporin-A treated and transplanted animals. Thus, the present invention shows that some undesired side effects associated with cyclosporin-A treatment for example, are attributable to an overstimulation of R-type $Ca^{2+}$ channels.

While a blockade of the elevated autocrine and self perpetuating secretion of mitogenic factors by cancer cells could have been suggested from the results by La Civita et al. (1996, supra), prior to the present invention, it was unknown whether this proliferative effect was related to the R-type $Ca^{2+}$ channel and whether it was a common mechanism in cancer and tumor cells. In accordance with the present invention, preliminary results using several types of human cancer cell lines seem to highly suggest that the proliferative effect of overstimulation acts through the R-type $Ca^{2+}$ channel and is indeed a common mechanism in cancer and tumor cells. Thus supporting the results for the R-type $Ca^{2+}$ channel and its blockade by Lomir/Dynacirc in human cancer as mentioned above in the Lomir/Dynacirc group of the MIDAS cohort (a non-specific R-type and C-type channel blocker). Thus, the present invention relates to a method of decreasing proliferation of cancer and tumor cells comprising an incubation thereof with an effective amount of a R-type $Ca^{2+}$ channel blocker. More particularly, the present invention relates to a method of decreasing proliferation of cancer and tumor cells comprising an incubation thereof with an effective amount of a R-type $Ca^{2+}$ channel blocker obtained from *Mandevilla* species and even more particularly of MV8608 and MV8612. In addition, the present invention provides a method for preventing non-properly regulated autocrine secretion using the specific R-type $Ca^{2+}$ channel blockers of the present invention (and pharmaceutical compositions therefor).

Further, prior to the present invention, it was unknown that a combination therapy of certain drugs which display potentially serious side effects such as renal impairment and hypertension (i.e. Sandimmune) with R-type $Ca^{2+}$ channel blockers could block or relieve these side effects. Furthermore, data using the rabbit (see example 9) indicate the presence of the R-type $Ca^{2+}$ channel in both the afferent and efferent renal arterioles. It remains to be seen whether the R-type $Ca^{2+}$ channel is present in renal arterioles. The instant invention along with that of all the published papers since 1991 by Bkaily et al. provides the rationale for an advantage of R-type $Ca^{2+}$ blocking agent such as Lomir/Dynacirc over other pure L-type $Ca^{2+}$ channel blockers in the long-term protection of renal function. The contribution of endothelin to the Sandimmune induced side effects of renal impairment and hypertension has now been assessed. The results highly suggest that blockade of the R-type $Ca^{2+}$ channel by Lomir/Dynacirc blocks the elevated circulating endothelin level induced with the Sandimmune drugs (Bkaily et al., data not shown).

The compounds of the present invention, in contradistinction to nifedipine and isradipine, do not induce hypertension in a normal patient.

From the wide variety of L-type $Ca^{2+}$ channel blockers such as nifedipine, nicardipine, Diltiazem, Clentiazem, Verapamil, D600 and D888 none were found to block the R-type $Ca^{2+}$ with the exception of isradipine (Lomir/Dynacirc) (data not shown). This later compound was found to block the R-type $Ca^{2+}$ channel with an $ED_{50}$ near ($10^{-8}$ M), the T-type $Ca^{2+}$ channel with an $ED_{50}$ near ($10^{-7}$M), the L-type $Ca^{2+}$ channel with an $ED_{50}$ near ($10^{-6}$M) and the fast $Na^+$ channel with an $ED_{50}$ near ($10^{-5}$M) (data not shown). Thus, although the R-type $Ca^{2+}$ channel blocker isradipine seems to be a potent R-type $Ca^{2+}$ blocker, it is not highly specific. On a clinical point of view, this drug seems to be more potent and to possess less side effects than other dihydropyridines (DHP) derivative L-type $Ca^{2+}$ channel blockers. The difference between isradipine and other DHPs compounds could be due to the potential of the former, to act as a R-type $Ca^{2+}$ blocker.

It has now been demonstrated that similarly to PAF, insulin and ET-1, bradykinin (BK) also induced a sustained increase of $[Ca]_i$ which was mainly nuclear and was due to the stimulation of the R-type $Ca^{2+}$ channel in human aortic endothelial and vascular smooth muscle, as well as chick and heart ventricular cells. The stimulation of R-type $Ca^{2+}$ channel by BK was due to the kinin activation of the $B_1$-receptor.

In accordance with the present invention, there is therefore provided a compound having the general formula of MV8612 analogs VIIA and VIIB, saponin-like derivatives thereof and pharmaceutically acceptable salts thereof.

In accordance with the present invention, there is also provided a saponin-like compound having the general formula EST or a derivative of the saponin-like compound, wherein E and S define a saponin oligosugar portion and T defines a steroid-like portion; wherein T is a pregnane-3β-ol derivative.

In addition, in accordance with the present invention, there is also provided a R-type $Ca^{2+}$ channel blocker having the general formula defined herein as EST.

Further, in accordance with the present invention, there is provided a specific R-type calcium channel inhibitor having the general formula EST.

In accordance with the present invention there is also provided a pharmaceutical composition for treating or preventing overstimulation of R-type $Ca^{2+}$ channels associated disease or condition in a warm blooded animal comprising at least one compound of general formula EST, together with a pharmaceutically acceptable carrier.

As well, in accordance with the present invention, there is also provided a pharmaceutical composition for blocking or relieving side effects of a drug which overstimulate R-type $Ca^{2+}$ channels comprising at least one compound of general formula EST, together with a pharmaceutically acceptable carrier.

In accordance with the present invention, there is also provided a method for specifically inhibiting overstimulation of a R-type $Ca^{2+}$ channel in a warm blooded animal comprising an administration of an effective amount of a compound of general formula EST, together with a pharmaceutically acceptable carrier.

BRIEF DESCRIPTION OF THE DRAWINGS

Having thus generally described the invention, reference will now be made to the accompanying drawings, showing by way of illustration a preferred embodiment thereof, and in which:

FIG. 2 shows the structure of MV8612 (analogs VIIA and VIIB);

FIG. 3 shows $^1$HNMR of compound MV8612 isolated from *Mandevilla Velutina*;

FIG. 4 shows $^{13}$CNMR of compound MV8612 isolated from *Mandevilla Velutina*;

FIG. 5 shows COSY (correlated spectroscopy) of compound MV8612 isolated from *M. Velutina*;

FIG. 6 shows HETCOR of compound MV8612 isolated from *M. Velutina*;

FIG. 15 shows the blockade by MV8608 ($10^{-9}$M) of the sustained depolarization induced by sustained increase of total $[Ca]_i$ via activation of the R-type $Ca^{2+}$ channels in chick and human heart cells;

FIG. 23 represents histograms showing that increasing the concentration of PAF ($10^{-7}$M) required high concentration of MV8608 ($10^{-6}$M) for blockade of PAF induced sustained increase of $[Ca]_i$ via activation of the R-type $Ca^{2+}$ channels in human aortic vascular smooth muscle cell lines;

FIG. 26 shows the time course blockade of the L-type $Ca^{2+}$ current by high concentration ($10^{-7}$M) of MV8612 in human heart cells;

FIG. 36 shows that pretreatment with MV8612 abolishes the bronchoconstrictive responses and the hypotensive effect of PAF in the anaesthetized guinea pig model;

FIG. 37 shows the effect of subplantar injection of compound MV 8608 isolated from *Mandevilla velutina* on paw oedema caused by subplantar injection of des-Arg$^9$-bradykinin (DABK) (A) in rats treated 24 h prior with LPS; bradykinin (BK, B) and for des-Arg$^9$-bradykinin (C) and for bradykinin (D) in animals treated 30 days prior with BCG. Each group represents the mean of 4–5 animals and the vertical bars the S.E.M. The asterisks indicate the significance levels: * $P<0.05$;

FIG. 38 shows the effect of subplantar injection of MV 8608 isolated from *Mandevilla velutina* on paw oedema caused by subplantar injection of prostaglandin $E_2$ ($PGE_2$) (A), PAF-acether (PAF) (B), substance P(SP) (C) and ovalbumin (OVO) (D). Each group represents the mean of 4–5 animals and the vertical bars the S.E.M. The asterisks indicate the significance levels: * $P<0.05$. Each group represents the mean of 4–5 animals and the vertical bars the S.E.M. The asterisks indicate the significance levels: * $P<0.05$;

FIG. 39 shows the effect of subplantar injection of MV 8608 isolated from *Mandevilla velutina* on paw oedema caused by subplantar injection of low dose of des-Arg$^9$-bradykinin plus PAF (A) or prostaglandin $E_2$ ($PGE_2$) (B). Each group represents the mean of 4–5 animals and the vertical bars the S.E.M. The asterisks indicate the significance levels: * $P<0.05$;

FIG. 40 shows the effect of subplantar injection of MV 8608 isolated from *Mandevilla velutina* on paw oedema caused by subplantar injection of carrageenan (Cg) (A), dextran (DEX) (B), histamine (HIST) (C) and for serotonin (5-HT) (D). Each group represents the mean of 4–5 animals and the vertical bars the S.E.M. The asterisks indicate the significance levels: * $P<0.05$;

FIG. 41 shows the effect of subplantar injection of MV 8612 isolated from *Mandevilla velutina* on paw oedema caused by subplantar injection of bradykinin (BK) (A and C), des-Arg$^9$-bradykinin (DABK) (B) and for tyr$^8$-bradykinin (D). Experiments for DABK were carried out in animals treated with LPS 24 h prior. Each group represents the mean of 4–5 animals and the vertical bars the S.E.M. The asterisks indicate the significance levels: * $P<0.05$;

FIG. 42 shows the effect of subplantar injection of MV 8612 isolated from *Mandevilla velutina* on paw oedema caused by subplantar injection of prostaglandin $E_2$ ($PGE_2$ (A), PAF acether (PAF) (B), carrageenan (Cg) (C) and substance P (SP) (D). Each group represents the mean of 4–5 animals and the vertical bars the S.E.M. The asterisks indicate the significance levels: * $P<0.05$. Each group represents the mean of 4–5 animals;

FIG. 43 shows the effect of subplantar injection of MV 8612 isolated from *Mandevilla velutina* on paw oedema caused by subplantar injection of low dose of bradykinin plus CGRP (A), BK plus prostaglandin $E_2$ ($PGE_2$)(B); BK plus PAF C) or BK plus $PGI_2$ (D). Each group represents the mean of 4–5 animals and the vertical bars the S.E.M. The asterisks indicate the significance levels: * $P<0.05$;

Figure 45:
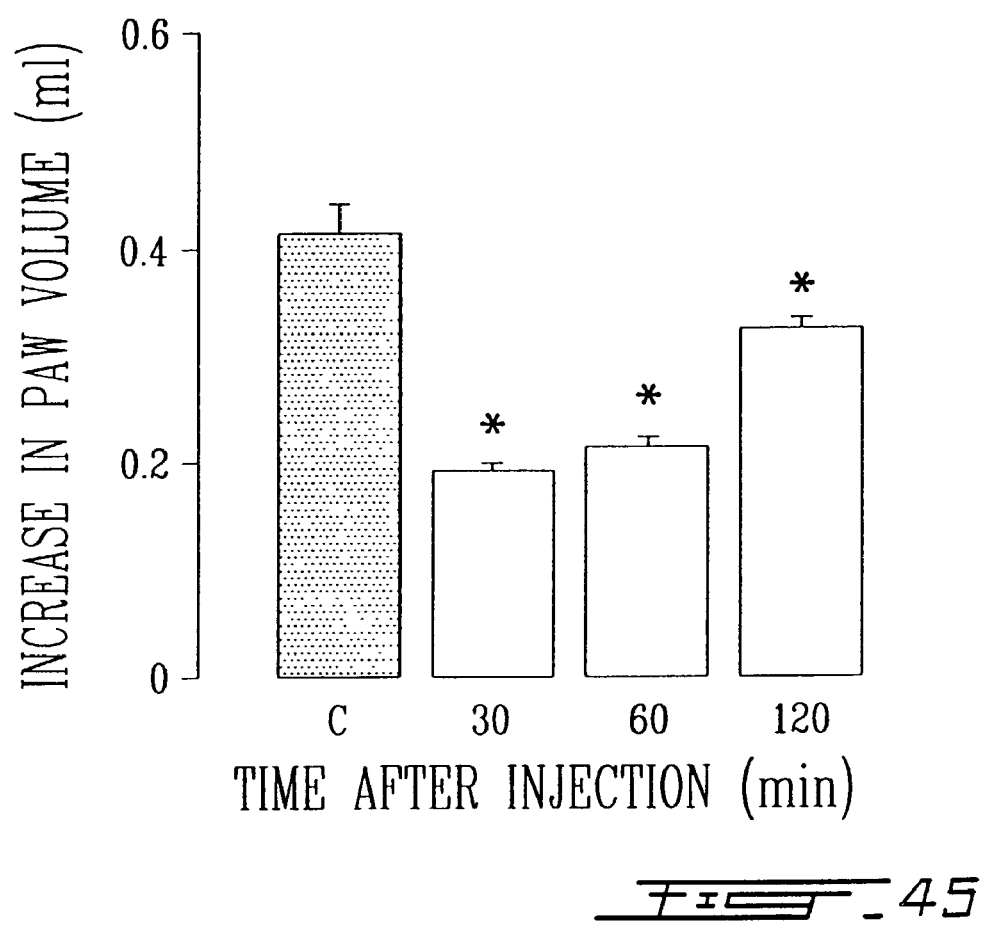
Figure 46:
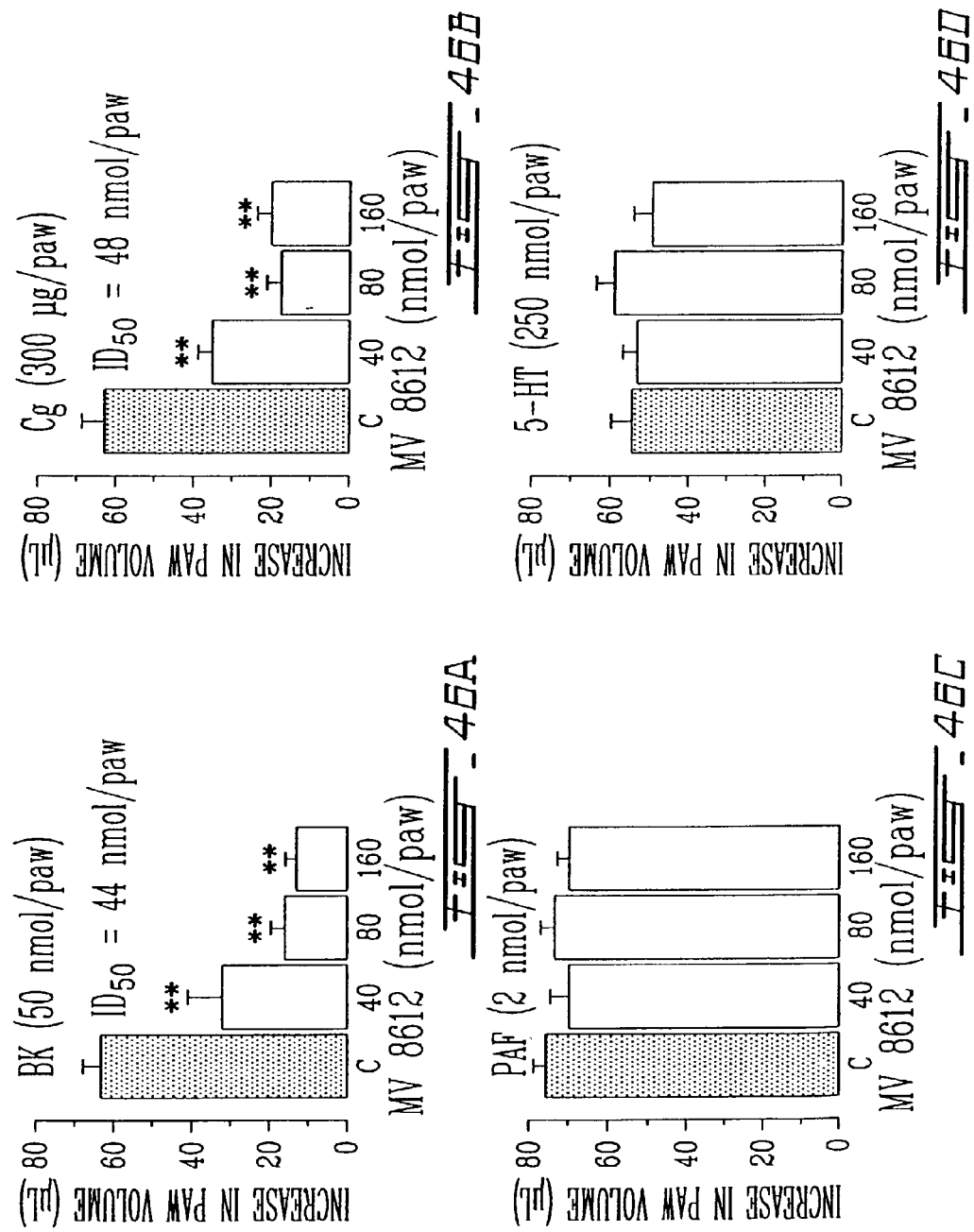
Figure 47:
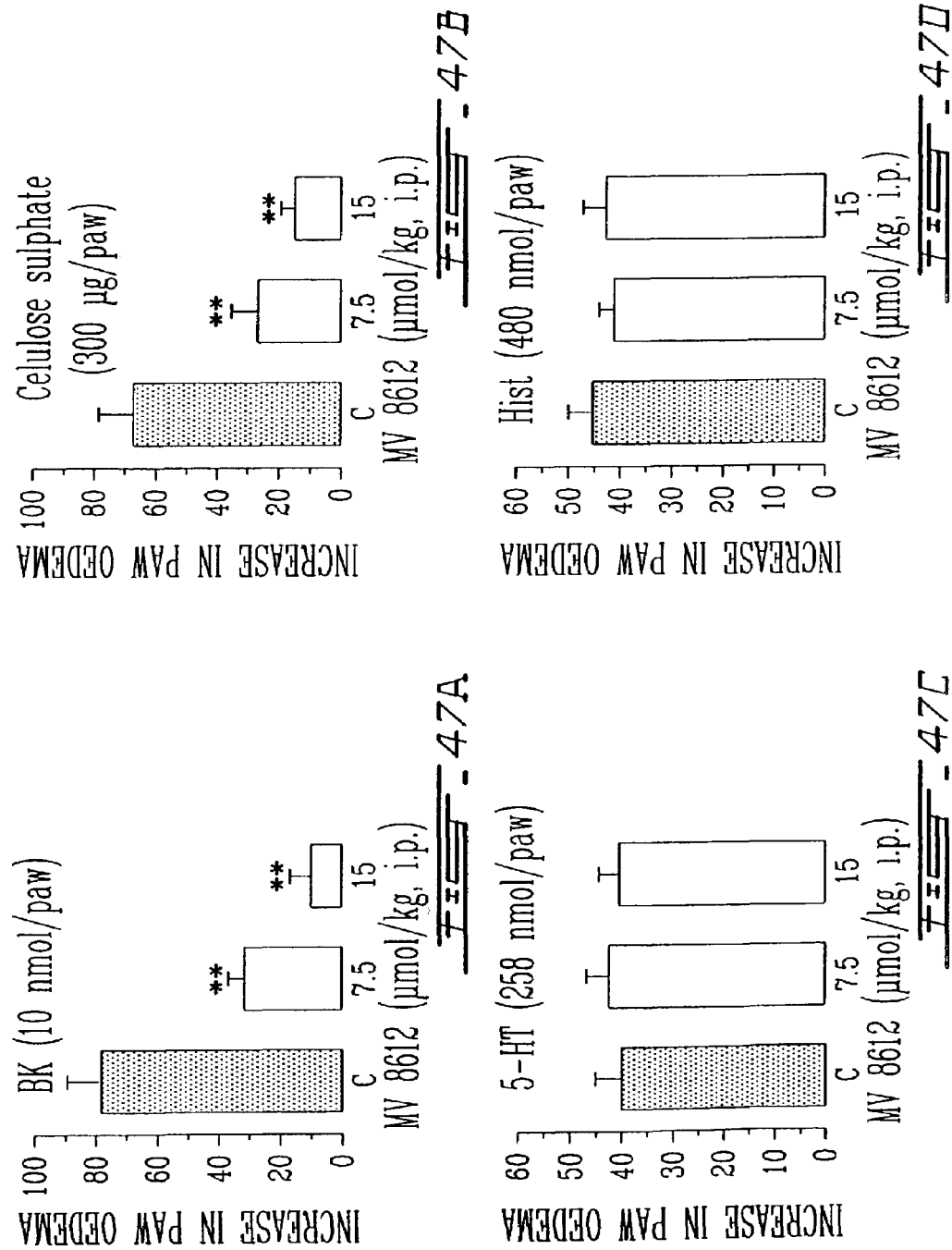
Figure 48:
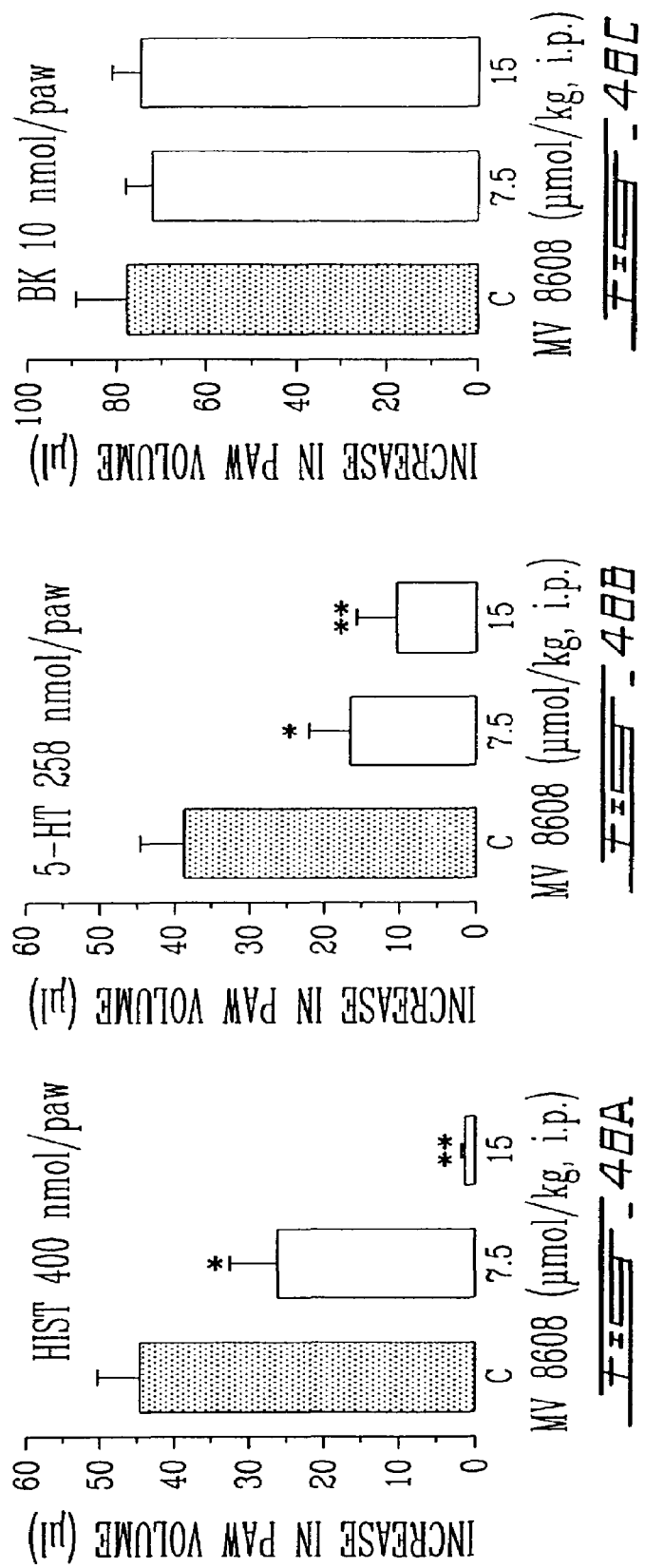
Figure 49:
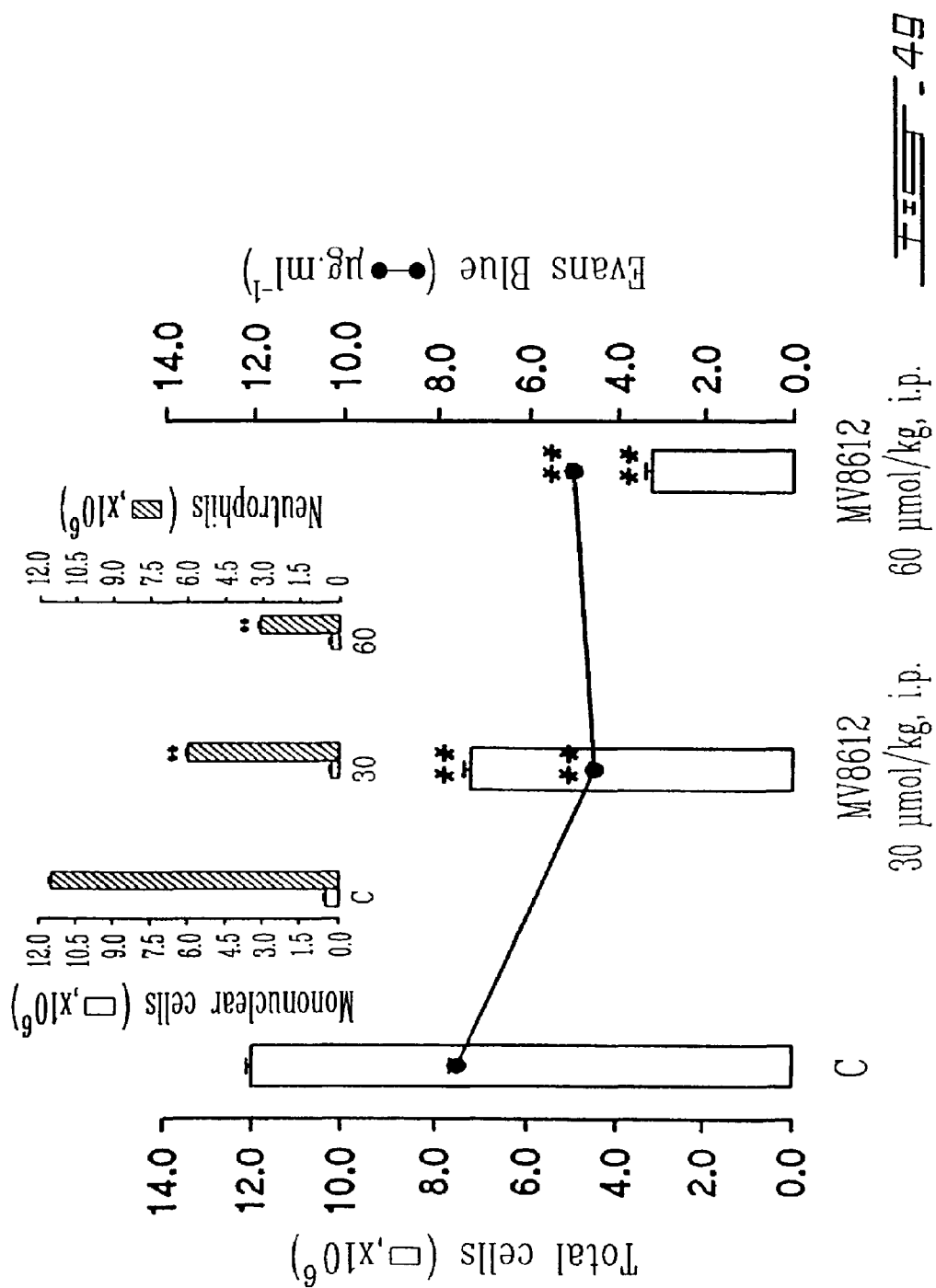
Figure 50:
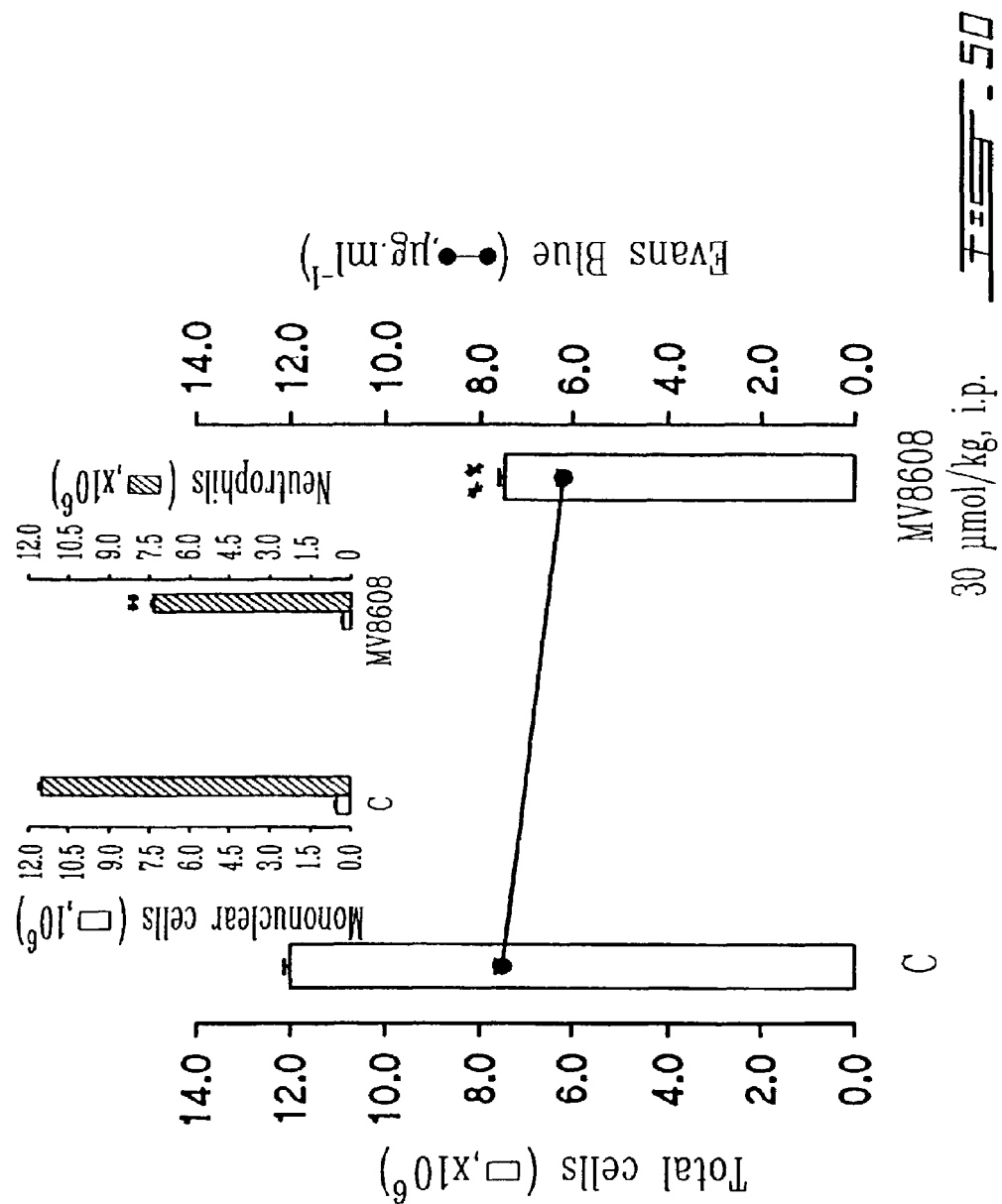
Figure 51:
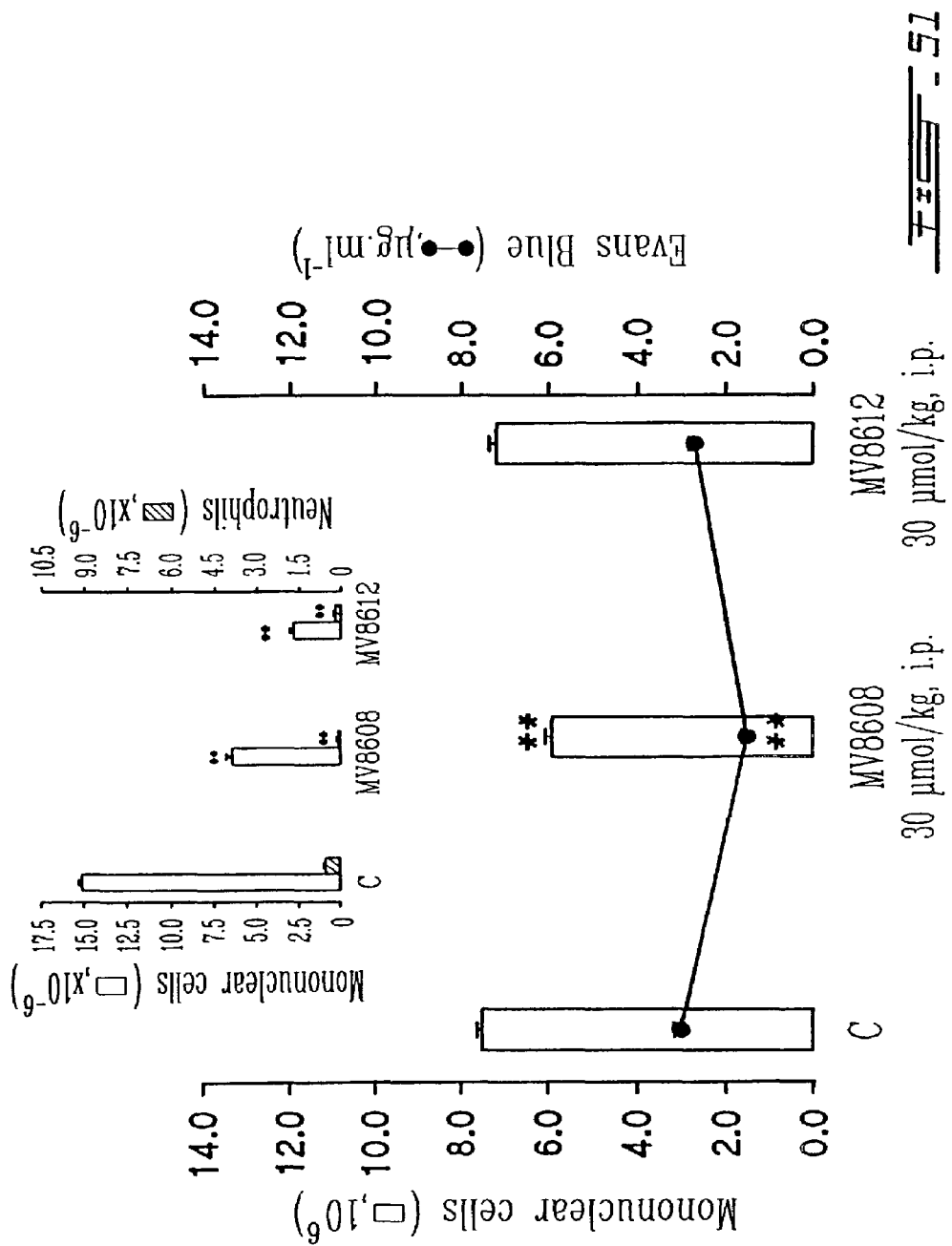
Figure 52B:
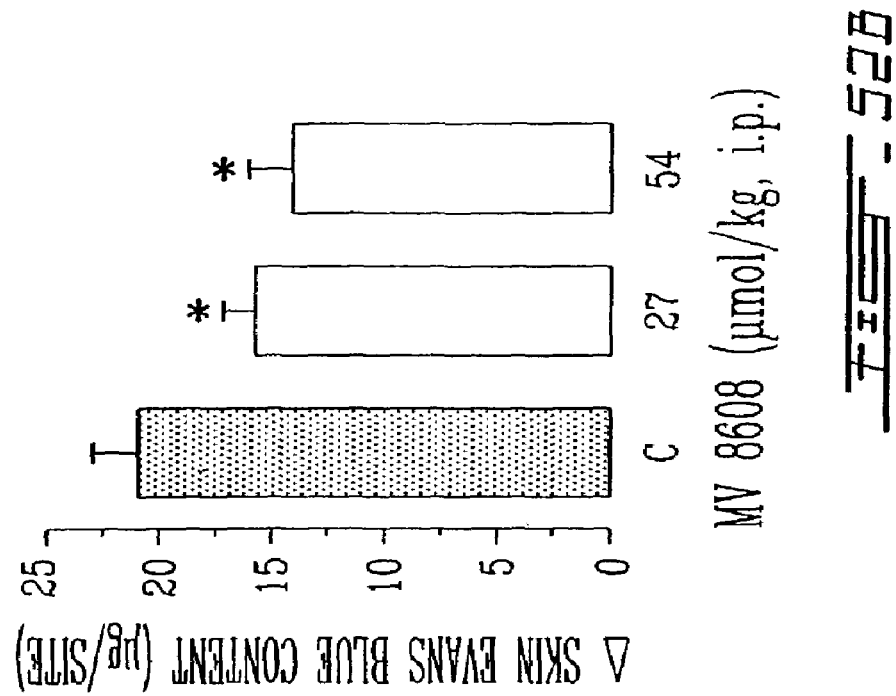
Figures 54A, 54B:
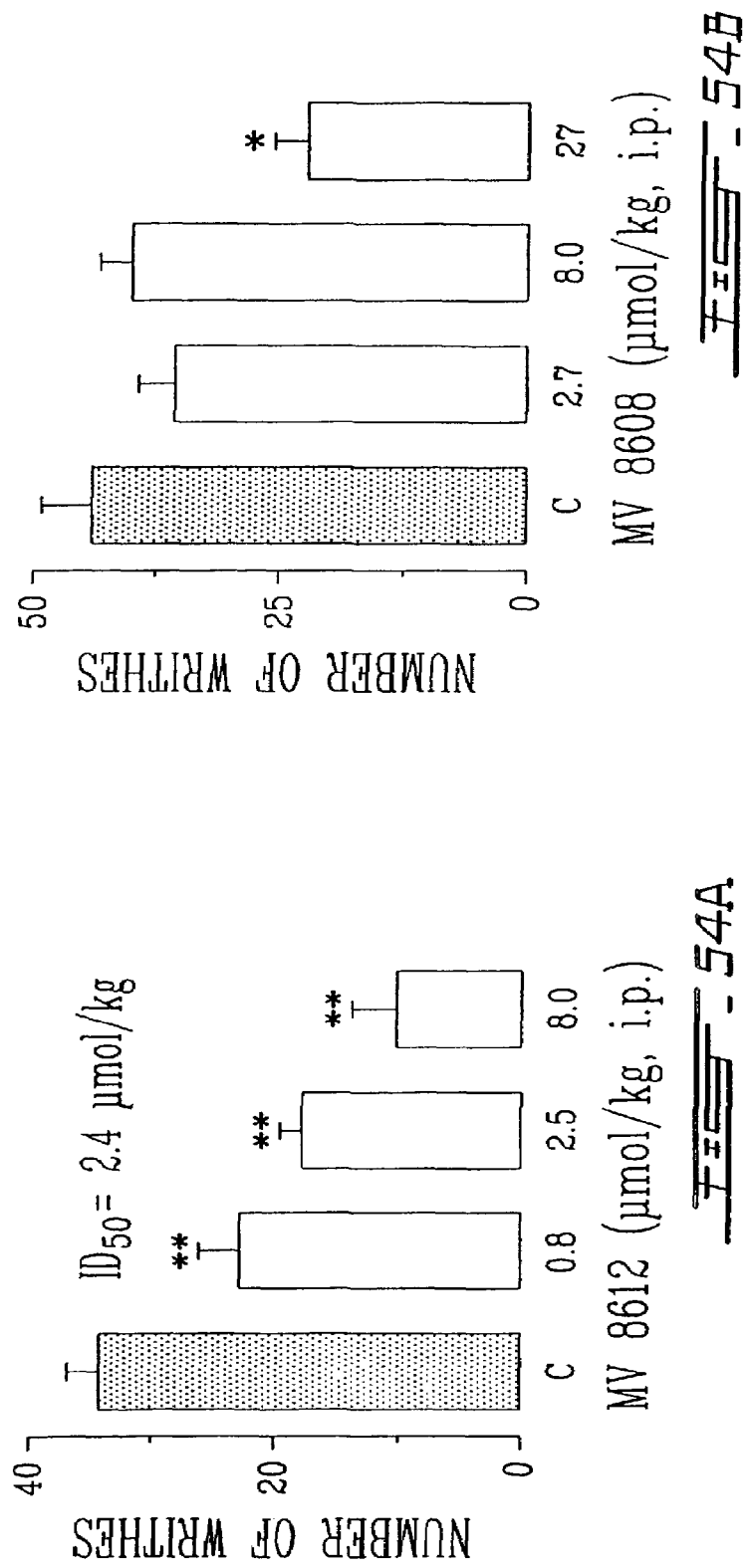
Figure 55B:
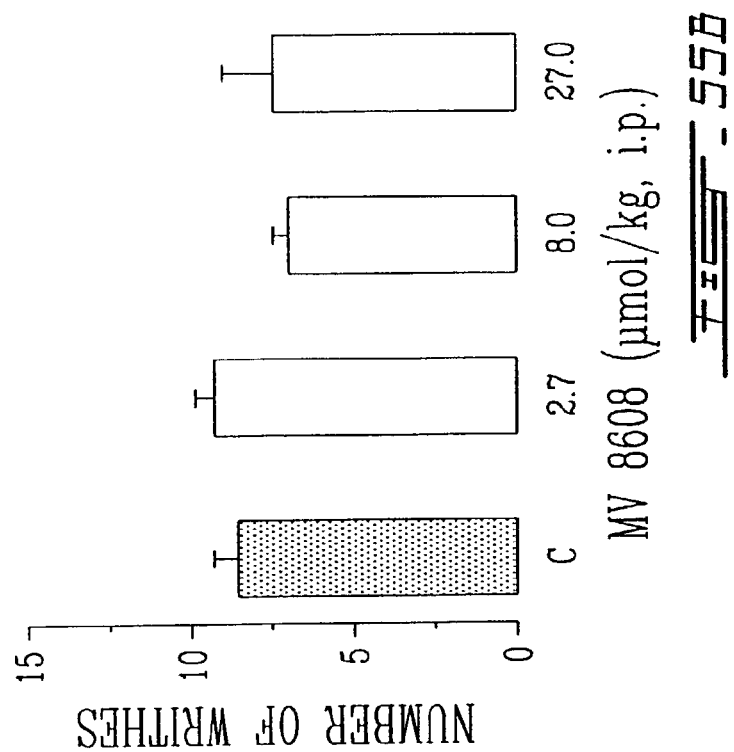
Figure 55A:
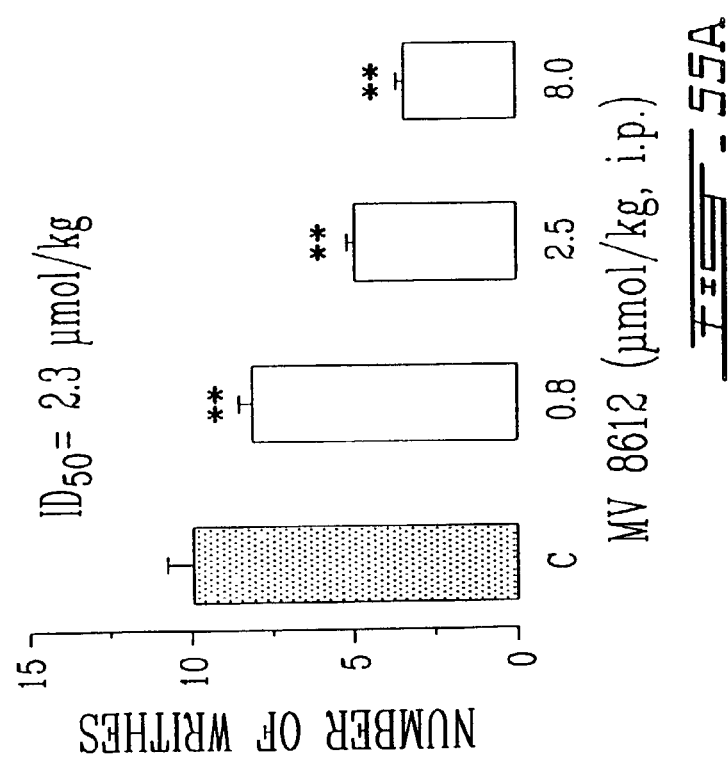

(B). Each group represents the mean of 4 animals and the vertical bars the S.E.M. The asterisks indicate the significance levels: * P<0.05;

FIG. 45 shows a time-dependent antioedematogenic effect caused by subplantar injection of compound MV 8612 on bradykinin-induced rat paw oedema. Each group represents the mean of 4–5 animals and the vertical bars the S.E.M. The asterisks indicate the significance levels: * P<0.05;

FIG. 46 shows a dose-dependent antioedematogenic effect caused by co-injection of compound MV 8612 on bradykinin (BK, A), carrageenan (B), PAF (C and serotonin (D)-induced mouse paw oedema. Each group represents the mean of 7 animals and the vertical bars the S.E.M. The asterisks indicate the significance levels:* P<0.05; ** P<0.01;

FIG. 47 shows a dose-dependent antioedematogenic effect caused by intraperitoneal injection of compound MV 8612 on bradykinin (BK, A), cellulose sulphate (B)-serotonin (5-HT, C) and histamine (Hist, D)-induced mouse paw oedema. Each group represents the mean of 5–6 animals and the vertical bars the S.E.M. The asterisks indicate the significance levels: ** P<0.01;

FIG. 48 shows a dose-dependent antioedematogenic effect caused by intraperitoneal injection of compound MV 8608 on histamine (Hist, A)-serotonin (5-HT, B) and bradykinin (BK, C)-induced mouse paw oedema. Each group represents the mean of 5–6 animals and the vertical bars the S.E.M. The asterisks indicate the significance levels: *P<0.05; ** P<0.01;

FIG. 49 shows the effect of compound MV 8612 given intraperitoneally on carrageenan (1 mg/site)-induced pleurisy in mice. Each group represents the mean of 8 to 10 animals and the vertical bars the S.E.M. The asterisks indicate the significance levels: *P<0.05; ** P<0.01;

FIG. 50 shows the effect of compound MV 8608 given intraperitoneally on carrageenan (1 mg/site)-induced pleurisy in mice. Each group represents the mean of 8 to 10 animals and the vertical bars the S.E.M. The asterisks indicate the significance levels: ** P<0.01;

FIG. 51 shows the effect of compounds MV 8608 and MV 8612 given intraperitoneally on PAF-acether (1 g/site)-induced pleurisy in mice. Each group represents the mean of 10 animals and the vertical bars the S.E.M. The asterisks indicate the significance levels: ** P<0.01;

FIG. 52 shows a dose-dependent inhibition of bradykinin-induced skin vascular permeability in rats caused by intraperitoneal injection of MV 8612 and MV 8608. Each group represents the mean of 8 animals and the vertical bars the S.E.M. The asterisks indicate the significance levels: *P<0.05; ** P<0.01;

FIG. 53 shows a concentration-dependent inhibition of human lymphocyte proliferation caused by compounds MV 8612 and MV 8608. Each group represents the mean of 6–7 experiments and the vertical bars the S.E.M;

FIG. 54 shows a dose-related antinociceptive effect caused by intraperitoneal injection of compounds MV 8612 and MV 8608 against acetic-acid-induced writhe responses in mice. Each group represents the mean of 8 animals and the vertical bars indicate the S.E.M;

FIG. 55 shows a dose-related antinociceptive effect caused by intraperitoneal injection of compounds MV 8612 and MV 8608 against acetylcholine-induced writhe responses in mice. Each group represents the mean of 8 animals and the vertical bars indicate the S.E.M;

FIG. 56 shows a dose-related antinociceptive effect caused by intraperitoneal injection of compounds MV 8612 and MV 8608 against kaolin-induced writhe responses in mice. Each group represents the mean of 8 animals and the vertical bars indicate the S.E.M; and FIG. 57 shows a dose-related antinociceptive effect caused by i.c.v. injections of compounds MV 8612 and morphine against acetic acid-induced writhe responses in mice. Each group represents the mean of 8 animals and the vertical bars indicate the S.E.M.

Other objects, advantages and features of the present invention will become more apparent upon reading of the following non-restrictive description of preferred embodiments with reference to the accompanying drawing which is exemplary and should not be interpreted as limiting the scope of the present invention.

DESCRIPTION OF THE PREFERRED EMBODIMENT

The present invention thus concerns the saponin-like compounds isolated from *Mandevilla* species with specific R-type calcium channel blocking properties and more particularly to saponin-like compounds from *Mandevilla velutina* and *Mandevilla Illustris* which display the remarkable property of virtually only affecting the overstimulation of R-type $Ca^{2+}$ channels, without significantly affecting the basal activity thereof. In addition, these compounds, and especially MV8608 and MV8612, display the remarkable property of blocking or relieving the side effects associated with other drugs or compounds. Furthermore, the present invention concerns R-type $Ca^{2+}$ channel blockers showing significant activity in a number of applications ranging from a control of cellular proliferation to pain control.

The freshly collected rhizomes of *Mandevilla velutina* were extracted with ethyl acetate and then fractionated by column chromatrography on silica gel with methylene chloride and ethyl acetate as solvents giving 20 components. Two of these fractions showed indirect bradykinin blocking action. As mentioned previously, one of them named Velutinol (MV8608) shows that the structure comprises a pregnane skeleton. The structure of Velutinol A was determined (Yunes et al., 1993, Phythochemistry. 34:787–790; 1993, Phytochemical Analysis 4:76–81; 1993, Phytochem. Anal. 4:76–81; Bento, 1996, J. Chem. Soc. Perkin Trans 2:1359–1366; Yunes et al., 1996) as: 3-β-hydroxipregna-5-one derivatives (see FIG. 1, compounds I, IA and IB) and it was suggested to be a (15R, 16R, 20S)-14, 16:15,20:16,21-triepoxi-15,16-seco 14β, 17α-pregn-5-ene-3β, 15-diol. FIG. 1, (compounds I, IA and IB).

Pregnane derivatives have been reported to be present in several species (Abe et al., 1976, Phytochemistry 15:1745–1748; 1978, Chem. Pharm. Bull. 26 (10):3023; 1979, Chem. Pharm. Bull. 27 (7):1604–1610; 1981, Chem. Pharm. Bull. 29 (2):416; 1987, Chem. Pharm. Bull. 35 (10):4087; 1988, Chem. Pharm. Bull. 36 (2):612; 1988, Chem. Pharm. Bull. 36 (10):3811). In any event, others isomers could also exist as are shown by structures II, III, IV, V and VI (FIG. 1). According to the Calixto group, these isomers have also been shown to have activity through the bradykinin receptor.

For comparison structure of 5-pregnane-3β-ol-20-one is shown in FIG. 1 (compound V).

Surprisingly, it was discovered that compound MV8608 had an inhibitory activity on the R-type calcium channel. Furthermore, this inhibitory activity was shown to be specific to the R-type calcium channel.

Isolated from the same *Mandevilla velutina* rhizomes an other compound MV8612 has a very specific inhibitory activity on the steady-state calcium channel type R. The structure of MV8612 was determined. The invention also relates to the structure of MV8612 (analogs A and B compound, FIG. 2) and its saponin-like derivatives displaying an inhibitory activity of the steady-state R-type calcium channel. The primary structure of such compounds is shown in FIG. 2.

It is important to note that the molecule of the present invention consists of a classical saponin oligosugar part (designated as "ES" in FIG. 2) and a steroid ("T") portion. The structure of the steroid (T) component of the molecule is based on a 5 pregnane-3β-ol derivative with a tricyclic oxygenated ring system or illustrol isomer as shown in FIG. 1 (compounds V and VI). However, as will be recognized by a person of ordinary skill to which the instant invention pertains, derivatives of these compounds can possess inhibitory activity on the $Ca^{2+}$ influx into the cytosol, the nucleus, the mitochondria as well as the (SR) sarcoplasmic reticulum and (ER) endoplasmic reticulum, in the EST combination as shown in FIG. 2. The structure of "T" is preferably a 5-pregnane-3β-ol oxytricyclo 15-ol as shown in FIG. 2, although a 5-pregnane-3β-ol-20-one, cholesterol, cholic acid, ergosterol, stigmasterol, androstenon, digitoxygenin, β-sitostenol, uvaol, ursolic acid, sarsasapogenin, 18, β-glycyrrhetinic acid, betulin, betulinic acid, oleanoic acid, podocarpic acid are also encompassed as being within the scope of the present invention.

In the EST formula (FIG. 2, analog A), S is preferably α(1–4) (2-deoxy, 3-methoxy)-L-lyxotetrose, α(1–4) (2-deoxy, 3-methoxy) L-xylotetrose, α(1–4) (2-deoxy, 3-methoxy)-L-arabinotetrose, α(1–4)(2-deoxy, 3-methoxy)-L-xylotetrose, α(1–4)(2-deoxy, 3-methoxy-L-ribopyranotetrose, α(1–4)(2-deoxy, 3 methoxy-L-sorbotetrose, α(1–4)-L-lyxotetrose, α(1–4)-L-xylotetrose, α(1–4)-L-arabinotetrose, α(1–4)-L-xylotetrose, α(1–4)-3,4 methoxy-L-lyxotetrose, α(1–4)-3,4 methoxy-L-xylotetrose, α(1–4)-3,4 methoxy-L-arabinotetrose, α(1–4)-3,4 methoxy-L-xylotetrose, α(1–4)-3,4 methoxy-L-ribopyranotetrose, α(1–4)-3,4 methoxy-L-sorbopyranotetrose, α(1–4)-L-lyxotetrose, α(1–4)-L-xylotetrose, α(1–4)-L-arabinotetrose, (1–4)-L-riboyranoetrose, α(1–4)-L-sorbotetrose.

The MV8612 analog A has a monomeric to oligomeric of mentioned sugar derivatives, and has preferably a tetra sugar derivative. The terminal E of the analog A part is preferably 4-acetoxy-3-methoxy-L-α-lyxose, 4-acetoxy-3-methoxy-L-α-xylose, 4-acetoxy-3-methoxy-L-α-arabinose, 4-acetoxy-3-methoxy-L-α-xylose, 4-acetoxy-3-methoxy-L-α-ribopyranose, 4-acetoxy-3-methoxy-L-α-sor-bose-acetoxy.

The compound of formula I (I, IA and IB) and MV8612 analogs VIIA and VIIB could be modified into peptidic analogs (deprotection reaction of amines functions in peptidic syntheses, acid treatment or catalytic hydrogenation depending on the nature of the ES) in order to obtain peptidic analogs of compounds of formula I as commonly known to a person of ordinary skill. The compounds of formula I (IA and IB) could be, if necessary purified using classical technique such as crystallisation and/or silice column chromatography.

As used herein, "chemical derivatives" is meant to cover additional chemical moieties not normally part of the subject matter of the invention. Such moieties could affect the physico-chemical characteristic of the derivative (i.e. solubility, absorption, half life and the like, decrease of toxicity). Such moieties are exemplified in Remington's Pharmaceutical Sciences (1980). Methods of coupling these chemical-physical moieties to a polypeptide are well known in the art.

As used herein, the terms "molecule", "compound" or "ligand" are used interchangeably and broadly to refer to natural, synthetic or semi-synthetic molecules or compounds. The term "molecule" therefore denotes for example chemicals, macromolecules, cell or tissue extracts (from plants or animals) and the like. Non limiting examples of molecules include nucleic acid molecules, peptides, antibodies, carbohydrates and pharmaceutical agents. The agents can be selected and screened by a variety of means including random screening, rational selection and by rational design using for example protein or ligand modelling methods such as computer modelling. The terms "rationally selected" or "rationally designed" are meant to define compounds which have been chosen based on the configuration of the interaction domains of the present invention. As will be understood by the person of ordinary skill, macromolecules having non-naturally occurring modifications are also within the scope of the term "molecule". For example, peptidomimetics, well known in the pharmaceutical industry and generally referred to as peptide analogs can be generated by modelling as mentioned above. Similarly, in a preferred embodiment, the polypeptides of the present invention are modified to enhance their stability. It should be understood that in most cases this modification should not alter the biological activity of the interaction domain. The molecules identified in accordance with the teachings of the present invention have a therapeutic value in diseases or conditions in which the physiology or homeastasis of the cell and/or tissue is compromised by a defect in $Ca^{2+}$ homeostasis. Alternatively, the molecules identified in accordance with the teachings of the present invention find utility in the development of more efficient compounds to reduce or prevent overstimulation of R-type $Ca^{2+}$ channel associated diseases. As exemplified herein, the present invention provides numerous assay systems to test the effect of these molecules.

They can be also ionized with an acceptable pharmaceutical acid, or if it is possible and if it desired with an acceptable pharmaceutical base.

The necessary crude materials used in the processes described herein are either commercially available or easily accessible to a person of ordinary skill to which the present invention pertains knowledgeable of the instant invention and of the procedures available in the literature.

In comparison with the dual L and R-type $Ca^{2+}$ channel blocker, israpidine (PN200-110), the compounds of the present invention, presents a highly superior in vivo as well as in vitro specificity and potency as well as protective and therapeutics cellular activities against $Ca^{2+}$ overload in all cell types. Non-limiting examples of such cell types include heart, vascular smooth muscle, vascular and non vascular endothelial cells, bone cells, T lymphocytes, monocytes, smooth muscle cells, nerve cells, cerebral cells, and non-differentiated cells of anaplasic or neoplasic origins.

The tests realized in vitro on VSMC, VEC, bone cells, blood immune cells and heart cells in culture, placed in several pathological, electrical and hormonal conditions showed that the compounds of the present invention protected and blocked in a remarkable way and more potently than isradipine, cell integrity and $Ca^{2+}$ overload as well as $Ca^{2+}$-dependent over stimulation of hormone secretion and abnormal excitation-contraction coupling and conduction. Other tests carried out in vitro, using abnormal proliferation of T-lymphocytes as well as VSM, VEC and osteoblast cells, demonstrated that the compounds of the present invention significantly and remarkably protected the cells from proliferation, significantly largely decreased their capacity to undergo spontaneous proliferative processes and retained their normal integrity and function. The effects of the compounds of the present invention were largely superior to that of isradipine.

The tests in vivo, using rats and rabbits as well as guinea pigs as model systems for warm blooded animals demonstrated that the compounds of the present invention significantly prevented and blocked vasoconstriction, hypotension and airways hypereactivity induced by PAF, ET-1 and organ transplantation without any side effect. On note, the activity of the compounds of the present invention was shown to be superior to be largely superior to that of isradipine which was, in addition and in contradistinction to the compounds of the instant invention, the dual L- and R-type channel blockers isradipine, exhibited significant side effects.

The remarkable properties of the compounds of the present invention make them valuable compounds in treatment of numerous diseases and conditions in which R-type $Ca^{2+}$ channel blocking is beneficial. Non-limiting examples of such diseases or conditions include diseases of the cerebral, cardiac and vascular systems, and the immune system, for the treatment and prevention of cerebral and cardiac ischemia, vascular contraction, oedema, post-surgery and post-transplantation hyper-immune activities and related pathologies and septic shock.

In general, the protective effects of the compounds of the present invention and in particular of MV8612 find utility in the treatment of, for example, cardiac, vascular and cerebrovascular accidents of different origin, post-surgical traumas, encephalopathy, neuro-degenerative pathology, hypertrophy, cancer, diabetes type II, hyperthyroidism, osteoporosis, arrythmia, fibrillation as well as osteoporosis.

The property of the compounds of the present invention to protect cells during hypoxia and ischemia as well as remodelling also permits their use in the treatment and prevention of ischemia of peripheral tissues, mainly in cardiology for myocardial ischemia and coronary ischemia and their different clinical expressions such as for example angina, myocardial infarct, arrhythmias, vasospasms, heart failure, fibrillation; as well as in ophthalmology and in oto-rhino-laryngology during chorio-retinial vascular damage, vertigo of vascular origin, vertigo de Meuniere or d'acouphenes as well as digitalis intoxication.

The invention concerns also the addition of salts to the compounds of the present invention and in particular to the compounds of formula I (I, IA and IB) and MV8612 analogs VIIA and VIIB obtained with a mineral or organic pharmaceutically acceptable salt.

The pharmaceutically acceptable acids that can be used to obtain a salt, by addition to the compounds of the present invention, are well known to the person of ordinary skill and taught for example in Remington Pharmaceutical Sciences (1980). Non-limiting examples of pharmaceutically acceptable acids include chlorhydric acid, phosphoric acid, tartaric acid, malic acid, fumaric acid, oxalic acid, methanesulfonic acid, ethanesulfonic acid, camphoric acid, citric acid, etc.

Non-limiting examples of pharmaceutical bases which can saltify the compounds of the present invention and in particular the compounds of formula I (I, IA and Ib) and analogs VIIA and VIIB, include sodium, potassium, calcium, aluminium hydroxyl, carbonates of acaly metals or alkalinoterrus or organic bases such as triethylamine, benzylamine, diethanolamin, tertbutylamin, dicyclohexylamin, arginine, etc.

The present invention also relates to the pharmaceutical compositions including as an active ingredient, a saponin-like compound of the present invention. More particularly, a compound of the present invention having the EST structure as shown in FIG. 2 and, even more particularly, a compound of formula I (I, IA and IB) and MV8612 analogs VIIA and VIIB or their salt derivatives (by addition for example of a mineral or organic base or acid) together with a pharmaceutically acceptable carrier, as well known in the art. Non-limiting examples of such pharmaceutically acceptable carriers include inert excipients, non toxic covenants for pharmaceutical use and/or an agents attaching an aromatic agent, a delitement agent, edulcorant agent, lubricant agent as well as a liquid and semi-liquid vehicle adapted for different modes of administration such as for example sterile epirogenic water for intravenous administration (see for example Remington Pharmaceutical Sciences (1980)).

Non-limiting examples of pharmaceutical compositions according to the invention include, in particular, those adapted for oral, parental, ocular, per or transcutan, nasal, rectal, perlingual administrations such as ocular or nasal drops, pills, sublingus pills, capsules, tablets, suppositories, cremes, pomades, gels, and the like (see for example Remington Pharmaceutical Sciences (1980)).

The compositions of the present invention are generally presented in a dose form and can contain dependent on the patient treated, age and sex of the patient, from 0.1 to 500 mg of the active principle.

It can, depending on the route of administration be delivered at a dose of 0.1 to 500 mg of one or several times a day.

The terminology "pharmaceutical" is used herein in a broad sense to cover veterinary uses. The compositions will be readily adapted by the skilled artisan for the treatment of particular warm blooded animals to which the instant invention pertains.

From the specification and appended claims, the term therapeutic agent should be taken in a broad sense so as to also include a combination of at least two such therapeutic agents. Further, compounds according to the present invention can be introduced into warm blooded animals including human patients in a number of ways, as well known in the art. Erythropoietic cells can be isolated from the afflicted individual, transformed with a DNA construct according to the invention and reintroduced to the afflicted individual in a number of ways, including intravenous injection. Alternatively, the DNA construct can be administered directly to the afflicted individual, for example, by injection in the bone marrow. The DNA construct can also be delivered through a vehicle such as a liposome, which can be designed to be targeted to a specific cell type, and engineered to be administered through different routes.

For administration to humans, the prescribing medical professional will ultimately determine the appropriate form and dosage for a given patient, and this can be expected to vary according to the chosen therapeutic regimen (i.e. DNA construct, protein, cells), the response and condition of the patient as well as the severity of the disease.

Composition within the scope of the present invention should contain at least one of the active agents in an amount effective to achieve the desired therapeutic effect while avoiding adverse side effects. Typically, the compounds in accordance with the present invention (i.e. MV8608 or MV8612) can be administered to warm blooded animals (i.e. humans) in doses ranging from 0.005 to 1 mg per kg of body weight per day of the warm blooded animal which is treated. Pharmaceutically acceptable preparations and salts of the active agent are within the scope of the present invention and are well known in the art (Remington's Pharmaceutical Science, 16th Ed., Mack Ed.). The dosage will be adapted by the clinician in accordance with conventional factors such as the extent of the disease and different parameters from the patient. Typically, 0.001 to 50 mg/kg/day will be administered to the warm blooded animal.

The present invention is illustrated in further detail by the following non-limiting examples.

EXAMPLE 1

Procedure for Isolation and Purification of Compound MV8612 (FIG. 2)

The rhizomes of *Mandevilla velutina* were grounded into small pieces and extracted repeatedly with ethyl acetate. The extract was filtered and evaporated to yield a brown powder that accounts for 9% of the rhizomes. The extract was fractioned by silica gel column chromatography with a methylene chloride system containing increasing amounts of ethyl acetate.

Fractions were collected and monitored by thin layer chromatography (TLC; Silica Gel G), eluted with toluene-EtoAc-MeOH (55:45:5) and visualized with short and long wavelength u.v. light or with an arylaldehyde-AcOH—MeOH—$H_2SO_4$ (0:5:10:85:5) spray.

Fractions rich in velutinol glycoside MV8612 were rechromatographed in the same manner several times. Further purification by TLC yields the pure compound VIIB (FIG. 2) crystallized in ethanol.

Compound VI (0.0001% of dry weight) mp 148–150° C., white needles from ethanol responded positively to the Lieberman Burchard (Abisch et al., 1960, Helv. Chim. Acta 43:1844), Xanthydrol (Barton et al., 1952, Nature 170:249) and Keller-Kiliane (Nagata et al., 1957, Helv. Chim. Acta 40:41) indicating a stereoidal glycoside of a 2-deoxysugar.

The molecular formula was obtained through elementar analysis [((60.26%), H (7.94%), 0 (31.10%)] [Calc: ((60.80%) H(8.01%), O(31.10%) and fast atom bombardment (FAB) mass spectrum (MS) that afforded a molecular peak at m/z 1205 (M+$Na^+$); 1221 (M+$K^+$) and 1200 (M+$NH_4^+$) suggesting to be $C_{60}H_{94}O_{23}$. The IR spectrum showed peaks (KBr) at $cm^{-1}$: 3450 (—OH), 1745 (—$COCH_3$), 2920, 1440 ($OCH_3$), 1230, 1160, 1100, 1080, 1050 (O—C—O). Its methanolic solution is transparent in the UV visible region. In the mass spectrum the loss of fragment 45 from the aglicone, following by the loss of a fragment of 244, were indicative of a one terminal sugar with two acetyl and one methoxyl groups and suggesting a straight chain of sugars. The positive ionization fast atom bombardment mass spectra (FAB-MS) confirmed the result with peaks at m/z (%) 1137 [M—Co—OH]$^+$ (66) 893 [1137—$C_{11}H_{17}O_6$]$^+$ (10) 749[893—$C_7H_{12}O_3$)]$^+$ (21), 605 [749—$C_7H_{12}O_3^+$ (25); 462 [605-($H_7O_{11}$]$_3$ (10), 318[462—$C_7H_{12}O_3$]+ (15) and suggested that there are four dideoxy sugars in the molecule.

EXAMPLE 2

NMR Experiments

The results of the NMR experiments are shown in FIGS. 3–6.

1) $^1$HNMR Spectrum

The analysis of the 600 Mhz $^1$H NMR spectrum can be divided into three distinct regions. The first region [5.78 ppm–4.28 ppm] with the best resolved signals, corresponds to the five anomeric protons and protons at C2 and C4 of the sugar ring 5, besides protons 16, 6, 15 (H), 15(OH), 10 and 21b of the genin part (velutinol).

For the second region [3.93 ppm–3.15 ppm], a very crowded region, the integration is proportional to 31 protons and were assigned as protons 3 and 21 a of the genin part, five methoxy and fourteen methine protons of the sugar rings.

The integration of the last region (2.53–1.08 ppm] showed the presence of fifty protons; five secondary methyl, eight methylenic, two methyl from acetyl groups and twenty-one protons from the genin part.

2) 1 D Selective TOCSY

The 1 D selective TOCSY was used to define each one of the five spin systems for the sugar rings attached to the genin part. Selective irradiation of an isolated spin multiplet yields a subspectrum of all hydrogens directly or indirectly scalar, coupled to the irradiated resonance, if the mixing time is long enough to allow complet transfer of magnetization. A description of the results is given in Table 1.

TABLE 1

1D selective TOCSY

| Irradiated proton | Observed signals (δ, ppm) | | | | | |
|---|---|---|---|---|---|---|
| | H1 | H2 | H3 | H4 | H5 | H6 |
| H1, R1 δ = 4.45 ppm | X | Ax:1.58 Eq:2.08 | 3.81 | 3.22 | 3.85 | 1.22 |
| H1, R2 δ = 4.76 ppm | X | Ax:1.64 Eq:2.11 | 3.78 | 3.19 | 3.34 | 1.21 |
| H2, R3 (ax) δ = 1.57 ppm | 4.45 | Ax:1.57 Eq:2.29 | 3.40 | 3.15 | 3.28 | 1.29 |
| H1, R4 δ = 4.96 ppm | X | Ax:1.55 Eq:2.16 | 3.77 | 3.19 | 3.92 | 1.21 |
| H2, R5 δ = 5.12 ppm | 4.43 | 5.12 | 3.33 | 5.33 | 3.70 | 1.21 |

The four anomeric protons of 2,6-dideoxyhexopyranose appeared as a doublet of doublets at 4.96; 4.85; 4.76 and 4.45, with J=10 and 2 Hz. A fifth anomeric proton appeared as a doublet (J=10 Hz), 4.43 and was assigned to the normal hexapyranose unit. The large value of the coupling constant of these anomeric protons were typical of the axial configuration of the hexopyranoses in the C-1 (D) conformation indicating that these sugars were joined through (1→4)-glycosidic linkages.

The spectrum also contained five methoxy groups which appear as singlets and were observed at 3.37(3H), 3.44(3H), 3.39(3H), and 3.34(6H); five secondary methyl groups appear as doublets and were observed at 1.21(9H), 1.22(3H) and 1.29(3H), (J=6.0 Hz); two tertiary methyl groups singlets were observed at 1.08 and 1.11 and two methyl from acetyl groups were observed at 2.07 and 2.18.

The eight C-2 methylene protons of four 2-deoxy sugar units appeared as two sets of four protons multiplets in the regions 2.29–2.08 and 1.64–1.55 for the equatorial and axial protons respectively (Abe et al., 1988, Chem. Pharm. Bull. 36 (2):612; Abe et al., 1987, Chem. Pharm. Bull. 36 (10): 3382–3389). There is also a doublet of doublets at 5.12 (J=10 and 8 Hz) attributed to the C-2 proton of the acetylated sugar, it couples with both the signals at 4.43 (anomeric proton) and 3.33 credited to a C-3 proton. The C-3 signal, part of a multiplet, is coupled with a doublet of doublets at 5.33 (J=3.0 and 2.0 Hz) attributed to the C-4 proton of a diacetyl sugar, which in turn is coupled with a doublet of doublets at 3.70 (J=6.0 and 2.0 Hz) attributed to the C-5 proton. This is in turn coupled to a doublet (J=6.0 Hz) at 1.21, attributed to the secondary methyl. The chemical shift for C-2 and C-4 is in accordance with an acetyl sugar derivatives.

3c) COSY Spectrum

The J coupling relationship described above was also determined from the COSY spectrum. The complete $^1$H NMR assignment of all the protons in the five sugar rings is given below:

| a) | H1, 4.43 | H2, 5.12 | H3, 3.33 | H4, 5.33 | H5, 3.70 | CH3, 1.21. |
|---|---|---|---|---|---|---|
| b) | H1, 4.96 CH3, 1.21. | H2, 1.55 and 2.16 | H3, 3.77 | H4, 3.19, | H5, 3.92 | |
| c) | H1, 4.45 CH3, 1.29 | H2, 1.57 and 2.29 | H3, 3.40 | H4, 3.15 | H5, 3.28 | |
| d) | H1, 4.76 CH3, 1.21. | H2, 1.64 and 2.11 | H3, 3.78 | H4, 3.19 | H5, 3.34 | |
| e) | H1, 4.85 CH3, 1.22. | H2, 1.58 and 2.08 | H3, 3.81 | H4, 3.22 | H5, 3.85 | |

4) $^{13}$C Spectrum, DEPTs and CH Correlations

The carbon 13 nuclear magnetic resonance spectra ($^{13}$C NMR) indicated the presence of six quaternary carbons, fourteen methyl, eleven methylene, twenty nine methine and two carbonyl groups (Breitmaier et al., 1987, Third Edition VCH Veriagsgprollachaft mbH weinheim RFG, Germany). The carbon signal were assigned on the $^1$H-$^{13}$C COSY (correlated spectroscopy) one-bond spectrum except for the quaternary ones. The long-range correlations data was used to assign these and the multiplicity of the protonated one was determined from the DEPT (distortion enhancement by polarization transfer) spectral data. The $^{13}$C assignments of the sugars are indicated in Table 2.

TABLE 2

$^{13}$C assignments (sugars) ($\delta$, ppm)

| | C1 | C2 | C3 | C4 | C5 | —CH3 | —Omc |
|---|---|---|---|---|---|---|---|
| R1 | 96.11 | 35.63 | 68.38 | 82.59 | 70.87 | 18.25* | 56.74 |
| R2 | 99.73 | 36.15 | 77.10 | 83.91 | 71.19 | 18.27* | 58.33 |
| R3 | 101.45 | 36.35 | 78.75 | 82.15 | 71.54 | 18.41 | 56.39 |
| R4 | 98.47 | 35.37 | 76.39 | 83.81 | 69.29 | 18.06 | 58.03 |
| R5 | 102.55 | 70.72 | 80.34 | 68.45 | 71.02 | 16.58 | 57.81 |

*These assignments can be interchangeable

| CH3—CO | | |
|---|---|---|
| CH3 | | CO |
| 20.87** | C2-R5 | 170.6 | C4-R5 |
| 20.97** | C4-R5 | 172.4 | C4-R5 |

(**) These assignments can be interchangeable

In agreement with the previous determination (ref. of velutinol) of the genin part (Velutinol A), the proton nuclear magnetic resonance spectra ($^1$H NMR) showed a characteristic signal due to the C-6 olefinic proton (5.38, m), as well as those due to C-19 and C-18 (1.08 and 1.11, s) methyl protons, C-3 methine proton (3.53, t,t), C-9, C-8, C-17, C-20, C-15 and C-16 methine protons (1.36, m; 2.01, td; 2.53, d,d; 4.44, d; 5.01, d; and 5.78,d, respectively) and C-21 methylene protons (, 3.81 and 4.28, d) (Abe et al., 1988, Chem. Pharm. Bull. 35 (10):4081–4087; Chen et al., 1987, Phytochem. 26 (8):2351) (Tables 3 and 4).

5) CH Long Range Correlations

The analysis of the $^1$H-$^{13}$C long-range data gave the following correlations which provide evidence for an attachment of the genin and the sugar residue, as well as for the following sequence of the sugar rings: (Table 5)

a) H3(3.35, V) C1(96.11, R1) and H1(4.85, R1) C3(77.64, V) define the linkage point between the genin and the sugar residue;

b) H4(3.22, R1) C1(99.73, R2) and H1(4.76, R2) C4(82.59, R1) define the connection between the first and second sugar rings;

c) H4(3.19, R2) C1(101.45, R3) and H1(4.45, R3) C4(83.91, R2) define the connection between sugar rings 2 and 3;

d) H4(3.15, R3) C1 (98.47, R4) and H1(4.96, R4) C4(82.15, R3) define the attachment of sugar ring 3 to sugar ring 4;

e) H4(3.19, R4) C1(102.55, R5) and H1(4.43, R5) C4(83.81, R4) define the linkage point between the last two sugar rings 4 and 5.

TABLE 3

$^{13}$C assignments for the genin part (velutinol) in compound-12 ($\delta$, ppm)

| Position | Velutinol* | Compound-12 |
|---|---|---|
| 1 | 37.4 | 37.57 |
| 2 | 31.4 | 29.67 |
| 3 | 71.3 | 77.64 |
| 4 | 42.0 | 38.89 |
| 5 | 139.3 | 140.49 |
| 6 | 121.4 | 121.56 |
| 7 | 25.9 | 26.07 |
| 8 | 33.5 | 33.69 |
| 9 | 45.8 | 45.94 |
| 10 | 37.6 | 37.96 |
| 11 | 18.6 | 18.68 |
| 12 | 26.6 | 26.80 |
| 13 | 43.5 | 43.70 |
| 14 | 87.1 | 87.40 |
| 15 | 92.5 | 92.67 |
| 16 | 108.7 | 108.84 |
| 17 | 52.3 | 52.47 |
| 18 | 21.6 | 21.74 |
| 19 | 19.1 | 19.17 |
| 20 | 73.8 | 73.96 |
| 21 | 78.0 | 78.19 |

*Breitmaier, E. et al., 1987, Carbon 13 NMR Spectroscopy-High Resolution Methods and Applications in Organic Chemistry and Biochemistry, Third Edition VCH Veriagsgprollachaft mbH weinheim RFG, Germany.

TABLE 4

$^1$H NMR assignments of Velutinol and of the aglycone of 8612 compound ppm
$\delta$.-$^1$H

| Position | Velutinol | Compound 12 |
|---|---|---|
| 1 | 1.12(a): 1.82(b) | 1.14(a)qd: 1.82(b)dt.J = 13.5:3.5 |
| 2 | 1.85(a): 1.50(b) | 1.95(a): 1.56(b) |
| 3 | 3.53(H.a): 1.80(OH) | 3.53(tt.J = 11.5:4.5) |
| 4 | 2.30(a): 2.23(b) | 2.34(a): 2.23(b) |
| 5 | — | — |
| 6 | 5.38 | 5.38(m) |
| 7 | 2.16(a): 1.89(b) | 2.16(a): 1.90(qd.J = 18.0:5.0:2.5) |
| 8 | 2.01 | 2.01(td.J = 11.5:5.5) |
| 9 | 1.36 | 1.36(dd) |
| 10 | — | — |
| 11 | 1.64(a.b) | 1.64(a.b)m |

TABLE 4-continued

¹H NMR assignments of Velutinol and of the aglycone of 8612 compound

| | ppm δ.-¹H | |
|---|---|---|
| Position | Velutinol | Compound 12 |
| 12 | 2.35(a): 1.65(b) | 2.35(a): 1.65(b) |
| 13 | — | — |
| 14 | — | — |
| 15 | 5.01(H): 4.75(OH) | 5.01(H)d.j = 12.0: 4.75(OH)d.J = 12 |
| 16 | 5.78 | 5.78(d.J = 4.5) |
| 17 | 2.53 | 2.53(dd.J = 6.0:4.5) |
| 18 | 1.11 | 1.11(s) |
| 19 | 1.09 | 1.08(s) |
| 20 | 4.45 | 4.44(dd.J = 6.0:3.5) |
| 21 | 3.81(A) | 3.81(A)dd.J = 10.0:3.5 |
| | 4.28(B) | 4.28(B)d.J = 10.0 |

TABLE 5

¹³C—¹H correlation long range

| C-1 (δ, ppm) | | H (δ, ppm) | |
|---|---|---|---|
| R-1 | 96.11 | 3.53 | H3(Vel.) |
| R-2 | 99.73 | 3.22 | H4-R1 |
| R-3 | 101.45 | 3.19 | H4-R2 |
| R-4 | 98.47 | 3.15 | H4-R3 |
| R-5 | 102.55 | 3.19 | H4-R4 |

| C (δ, ppm) | | H-1 (δ, ppm) | |
|---|---|---|---|
| C-3 (velutinol) | 77.64 | 4.85 | R-1 |
| C4-R1 | 82.59 | 4.76 | R-2 |
| C4-R2 | 83.91 | 4.45 | R-3 |
| C4-R3 | 82.15 | 4.96 | R-4 |
| C4-R4 | 83.81 | 4.43 | R-5 |

6) NOESY Spectra

The analysis of the cross peaks in the NOESY (2D n.O.e) spectra also provides evidence for the above mentioned connections between the sugar rings and the genin. The most important interactions are the following:

| | | | |
|---|---|---|---|
| H1(4.43, R5) | H4(3.19, R4); | H1(4.96, R4) | H4(3.15, R3); |
| H1(4.45, R3) | H4(3.19, R2); | H1(4.76, R2) | H4(3.22, R1); |
| H1(4.85, R1) | H3(3.53, V); | H1(4.85, R1) | H4(2.34, V). |

The analysis of the NOESY spectra also showed that in each of the sugar rings, proton at C-3 couple with proton in the C1, and this is in turn spatially coupled to proton at C-5 position. Such proximities can occur if these protons are all axial. This thus provides evidence that the methoxy and the secondary methyl groups are located at equatorial positions.

The values for the coupling constants (J) for protons 2 (10 and 8 Hz) and 4 (3.0 and 2.0 Hz) of the last sugar ring (5.12 and 5.33, respectively) indicate their position as axial configuration at C-2 and an equatorial configuration at C4. The acetoxy groups are at equatorial and axial positions, respectively. In addition, the long range CH correlation spectra showed coupling between the two carbonyl at 170.6 ppm (acetyl at C-2) and 172.4 ppm (acetyl at C4), with the methyl signals at 2.08 ppm and 2.17 ppm, respectively.

The analysis of NMR spectra, specially long range CH correlations and cross peaks in the NOESY spectra, provides information for the connection between the sugar rings and the genin. The data from NMR confirm the sequence of sugars indicated by FAB-MS with the 6-deoxy-2,4-acetoxy-3-O-methyl hexopyranose as the terminal of the sugar chain.

EXAMPLE 3

Structure of the Compounds

In the formula EST for analog VIIB (FIG. 2) the structure of the T part of the molecule is a 5-pregnane-3-ol-20-one, cholesterol, cholic acid, ergosterol, stigmasterol, androstenon, digitoxygenin, -sitosterol, uvaol, ursolic acid, sarsasapogenin, 18, -glycylrhetinic acid, betulin, betulinic acid, oleanoic acid, padocarpic acid, and preferably 5-pregnane-3-ol oxytricyclo 15-ol as shown in FIG. 1 (I, IA, IB, II, III, IV).

S for analog B is preferably (1–4) (2-deoxy, 3-methoxy, 5-methyl)-L-lyxotetrose, (1–4) (2-deoxy, 3-methoxy) L-xylotetrose, (1–4) (2-deoxy, 3-methoxy)-L-arabinotetrose, (1–4)(2-deoxy, 3-methoxy)-1-xylotetrose, (1–4)(2-deoxy, 3-methoxy-L-ribopyranotetrose, (1–4) (2-deoxy, 3 methoxy-L-sorbotetrose, (1–4)-L-lyxotetrose, (1–4)-L-xylote-trose, (1–4)-L-arabinotetrose, (1–4)-L-xylotetrose, (1–4)-3,4 methoxy-L-lyxotetrose, (1–4)-3,4 methoxy-L-xylotetrose, (1–4)-3,4 methoxy-L-arabinotetrose, (1–4)-3,4 methoxy-L-xylotetrose, (1–4)-3,4 methoxy-L-ribopyranotetrose, (1–4)-3,4 methoxy-L-sorbopyranotetrose, (1–4)-L-lyxotetrose, (1–4)-L-xylotetrose, (1–4)-L-arabinotetrose, (1–4)-L-sorbotetrose.

E for analog VIIB is preferably diacetylfucose but also 4-acetoxy-3 methoxy-L-lyxose, 4-acetoxy-3-methoxyl-L-xylose, 4-acetoxy-3-methoxylL-arabinose, 4-acetoxy-3-methoxy-L-xylose, 4-acetoxy-3-methoxy-L-ribopyranose, 4-acetoxy-3-methoxy-L-sorbose-acetoxy.

MV8608—Has only one sugar bonded to the genin part T (FIG. 2).

MV-8609—Has in the part S of FIG. 2 only one sugar.

MV-8210—Has on the part S of FIG. 2 two sugars.

MV-8611—Has in the part S of FIG. 2 three sugars.

All of these compounds were demonstrated to be active against bradykinin-induced pharmacological effects (Calixto, Yunes, et al., 1987, supra; Calixto et al., 1988, Br. J. Pharmacol., 94:1133–1142).

EXAMPLE 4

Compounds from *Mandevilla illustris*

MI-07 (Illustrol)

The structure of illustrol (FIG. 1 compound VI) was determined by the same authors to be a derivative of 14:15-seco-15-norpregnane (Yunes et al. 1993, supra).

MI-15, MI-18 and MI-21

Demonstrated to be active against bradykinin-induced pharmacological effects (Calixto et al., 1991, General Pharmacol. 22:99–101; 1991, Memórias do Instituto Oswaldo Cruz, 86:195–202) are of similar structure to that indicated in FIG. 2, where the Genin (part T) correspond to the illustrol. The S part has one, two three or more sugars and the terminal sugar E is, as was indicated preferably, 6-deoxy-2,4-acetoxy-3-O-methyl hexopyranose.

EXAMPLE 5

Experimental Procedures

The freshly collected rhizomes of the *Mandevilla* species were cut into small pieces and repeatedly extracted with ethyl acetate at room temperature. The extract was filtered and evaporated under reduced pressure and the crude extract was fractioned by column chromatography on silica gel using methylene chloride with increasing amounts of ethyl acetate as eluent.

After repeated column chromatography of the fractions using hexane-acetone as eluents, it is possible to isolate several compounds that exhibit indirect bradykinin blocking action.

Figure 1A:
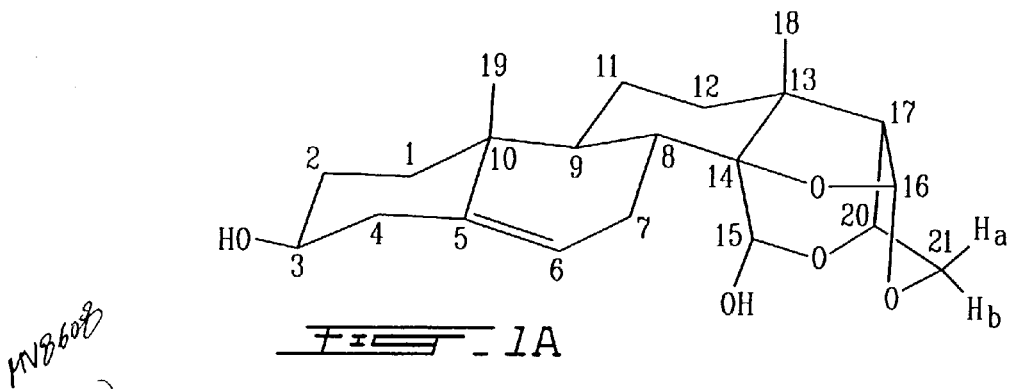
FIG. 1 shows the structure of compound of MV8608 and its isomers; as well as the structure of 5-pregnane-3β-ol-20 (compound V)
Figure 1B:
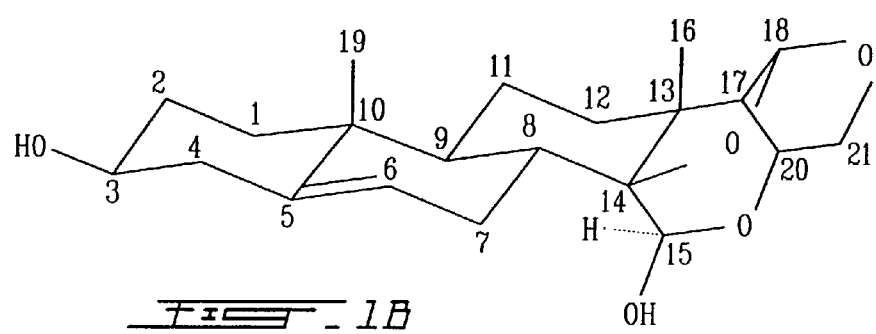
Figure 1C:
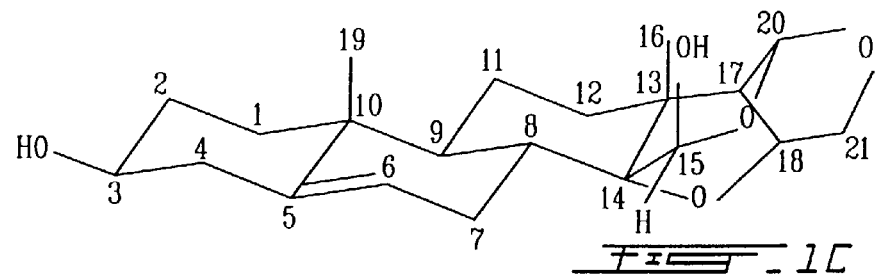
Figure 1D:
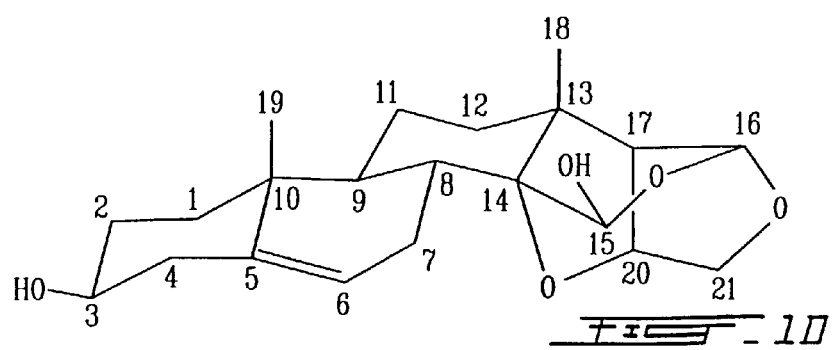
Figure 1E:
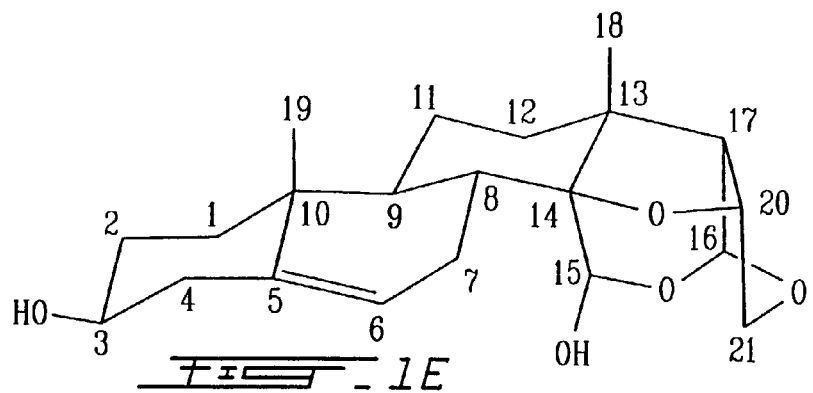
Figure 1F:
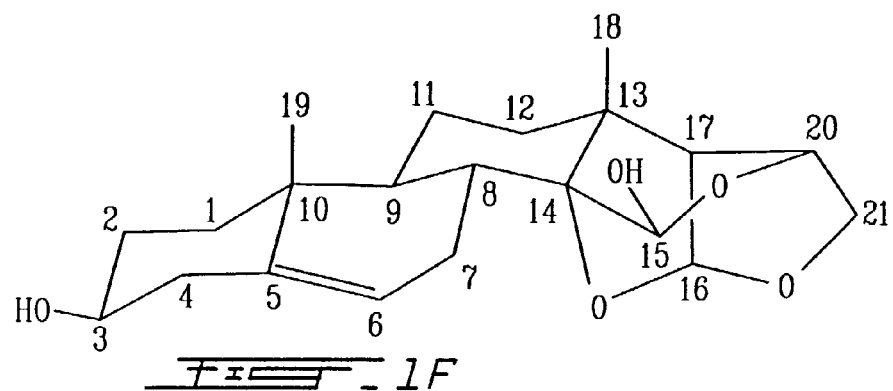
Figure 1G:
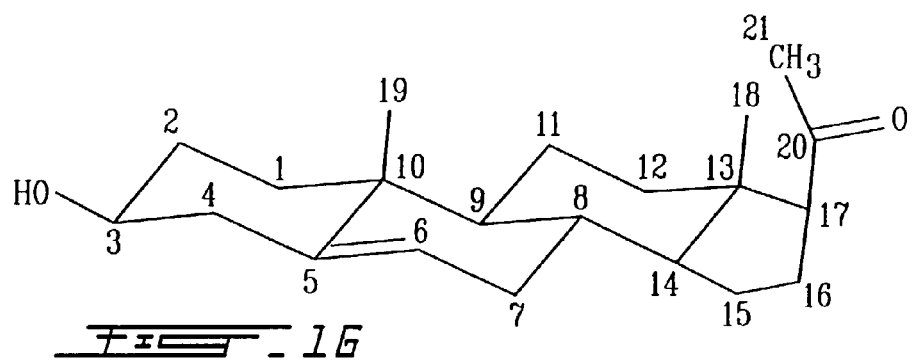
Figure 1H:
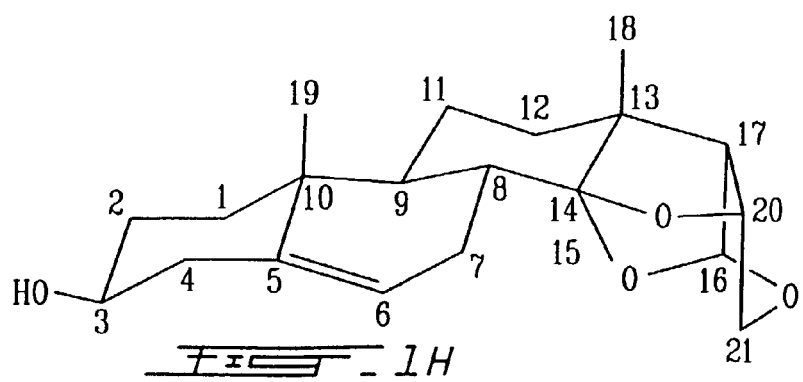
Figure 7:
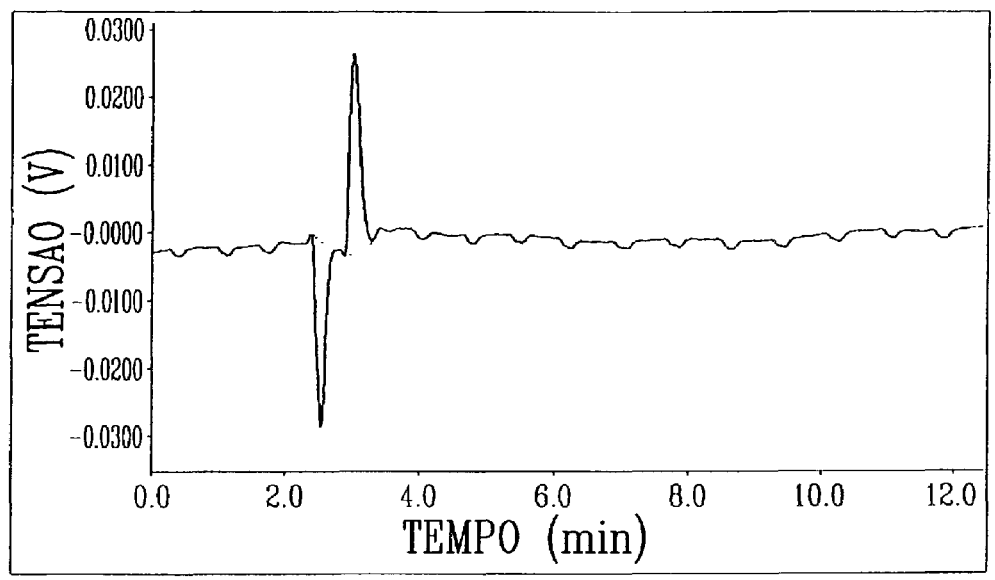
FIG. 7 shows HPLC chromatogram of compound MV8608 isolated from *M. Velutina*.
Figure 8:
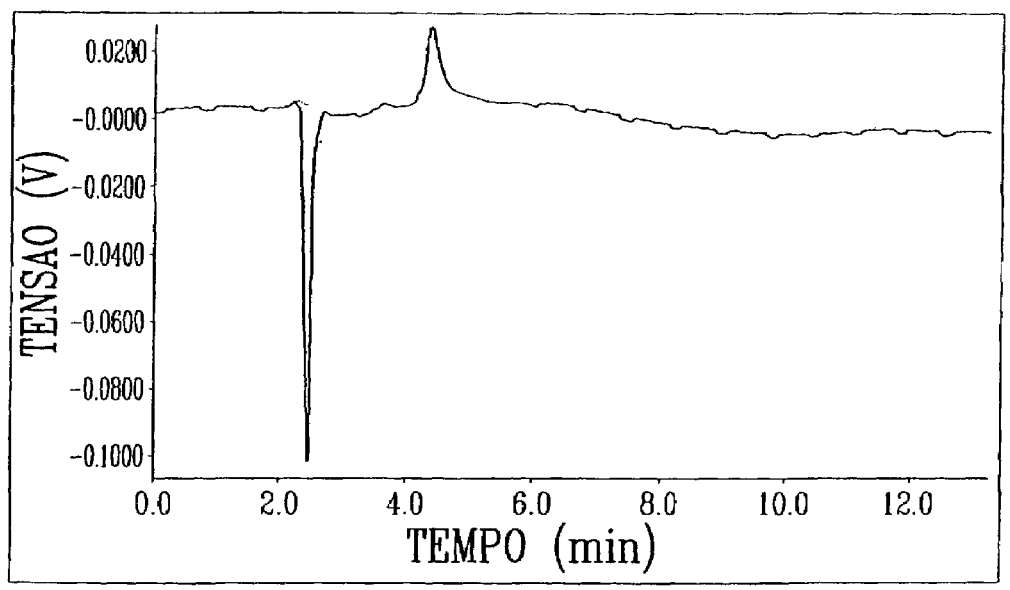
FIG. 8 shows HPLC chromatogram of compound MV8612 isolated from *M. Velutina*.
Figure 9:
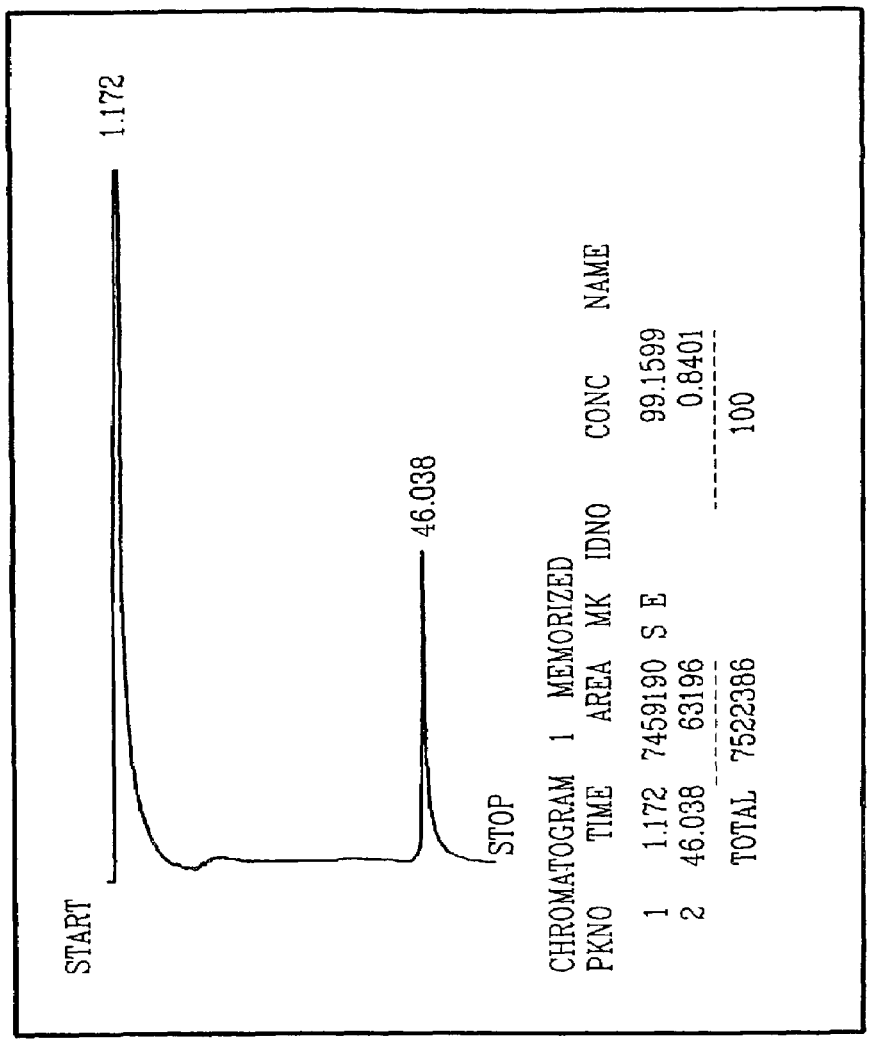
FIG. 9 shows GC chromatogram of compound MV8608 isolated from *M. Velutina*.
Figure 10:
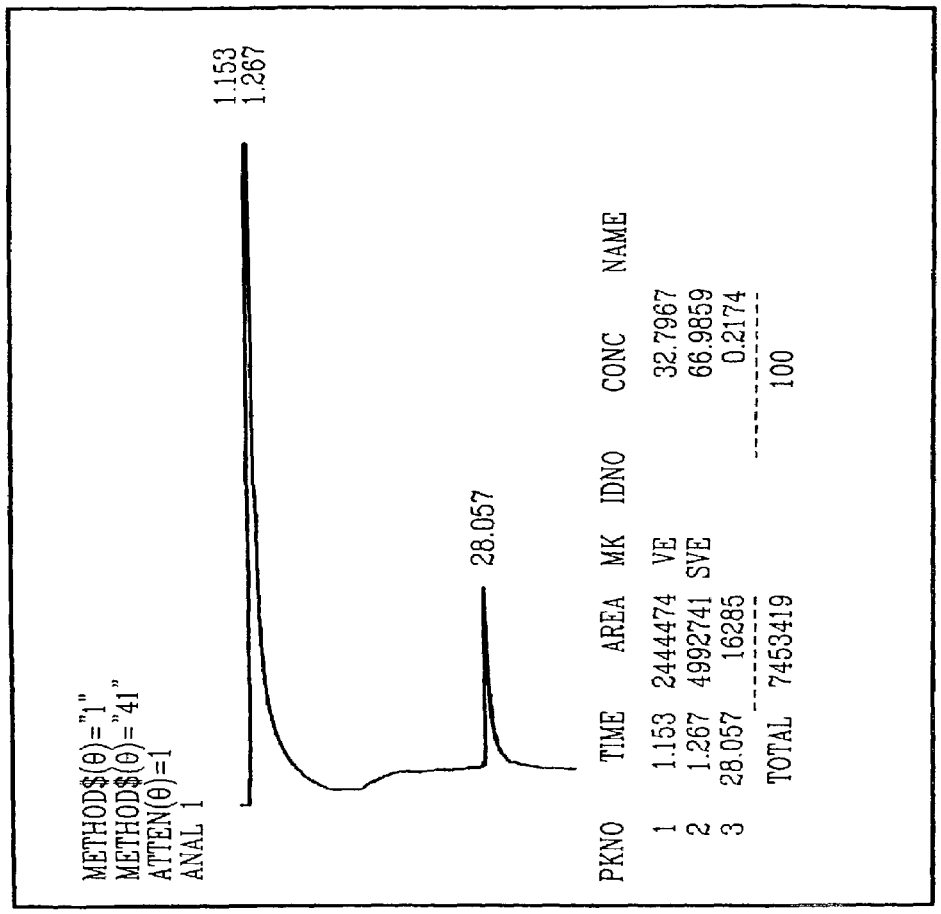
FIG. 10 shows GC chromatogram of compound illustrol isolated from *M. Illustris*.

HPLC chromatogram of MV8608 and MV8612 are observed in FIGS. 7 and 8 and a CG chromatogram of MV8608 in FIG. 9. The CG chromatogram of Illustrol is shown in FIG. 10.

M.ps. (melting point) were determined using a Kofler-stage microscope and are not corrected. Optical rotation were recorded at 18–28° C. using a 1 dm cell. IR spectrum was obtained from KBr discs and in $CHCl_3$ solution. Electron-impact mass spectra were taken on an MS Finnigam model 1020. The FAB-MS were taken on a Fison.

The NMR experiments were made in $CDCl_3$ solution with TMS as internal standard, using AM 250 and Amx 600 instruments, and a JEOL alpha 500 instrument. One-dimensional $^1H$ spectram were acquired as 64 K data points with a spectral width of 8.5 ppm (0–8.5). One-dimensional $^{13}C$ spectrum were recorded as 64 K data points with a spectral width of 200 ppm (0–200). The $^{13}C$ DEPT (distortionless enhancement by polorization transfer) experiments (90 and 135) were both recorded on the Bruker AM 250 spectrometer at 62.89 MHz. The 1D selective TOCSY were recorded on the JEOL alpha 500 MHz spectrometer. The phase sensitive DQF-COSY and NOESY (nucleus overhouser effect spectroscopy) were acquired using standard Bruker programs. The hereronuclear ($^1H$-$^{13}C$) correlation experiments, both one-bond and long-range correlation, were performed in reverse $^1H$ detected mode.

TLC was performed on silica gel (Merck Kilselgel 60 F254 0.25 mm layers). Column Chromatography was carried out on silica gel 200–300 mesh).

The plant material of *M. velutina* was collected from Minas Gerais State, Brazil, and was identified by Prof. Ademir Reis and Valério F. Ferreira of the Department of Botany of the Federal University of Santa Catarina. A voucher specimen is deposited in the Herbarium "Flor" of the Department of Botany, Federal University of Santa Catarina, under acession number 17.888-17.892.

EXAMPLE 6

Pharmacological Study of the Compounds of the Present Invention:

Principle of In Vitro Studies

Single cells from heart, VSM and VEC of human and animals in culture constitute a model of choice for looking at the effect of drugs on different types of ionic channels using whole-cell and single channel patch clamp techniques in normal and stimulated conditions (Bkaily et al., 1988, supra; 1991, supra; 1992, supra; 1992a, supra; 1993a, supra; 1996a–e, supra; Bkaily G. 1994a,b, supra). Indeed, it is recognized as a model system in analyzing drug ionic channel interactions.

Heart cells as well as VSMC possess fast $Na^+$ current, T, L and R-type $Ca^{2+}$ channels as well as different types of $K^+$ channels (Bkaily G., 1991, supra; 1995, supra). However, vascular endothelial cells (VECs) only possess R-type $Ca^{2+}$ channels and different types of $K^+$ channels. Thus, the later type of VECs constitute a model of choice for studying the effect of drugs on $Ca^{2+}$ influx due to opening of the R-type $Ca^{2+}$ channels (Bkaily G., 1994, supra; 1996, supra; 1997a–d, supra). Of note, the R-type $Ca^{2+}$ channel has been reported to be responsible for the sustained increase of intracellular calcium and nuclear and cytosolic $Ca^{2+}$ overload that are a result of sustained depolarization of the cell membrane or continual presence of several cardioactive and vasoactive hormones such as ET-1, PAF, bradykinin and insulin (Bkaily G., 1994, supra; 1992, supra; 1993, supra; 1995, supra; 1996, supra; 1997a, supra; 1997b, supra; 1997c, supra; 1997d, supra; 1998, supra).

A sustained increase of cytosolic, nuclear and mitochondrial $Ca^{2+}$, considered as pathological, is a visible and measurable aggression in all types of excitable and non excitable cells such as heart cells, VSMC, VEC, osteoblast cells and immune cells (Bkaily et al., 1996, supra).

Herein the effect of the compounds of the present invention were tested on the above-mentioned cell types at whole-cell and cell attached patch clamp configurations, as well as at $[Ca]_i$, $[Ca]_c$ and $[Ca]_n$ levels using a standard techniques (Bkaily, 1994a,b, supra; 1992, supra; 1993, supra; 1995, supra; 1996, supra; 1997a,b,c,d, supra; 1998, supra).

Methodology

Single cells of different types in culture were prepared from biopsies of human, chick and rabbit. Known and accepted methods for the isolation of fast $Na^+$ current, T, L and R-type $Ca^{2+}$ channels as well as delayed outward $K^+$ current were used (Bkaily 1994, supra).

The compounds to be tested are added to the appropriate extracellular solution after recording a stable ionic current or normal steady-state level of $[Ca]_n$ and $[Ca]_n$. The effect of different concentrations of compounds are tested on the different type of current and $[Ca]_i$ of the different cell types. The effect of each concentration of the compounds in function of the time of exposure are then determined. Once the steady-state effect is reached, the second concentration is added, etc.

Also, for the R-type $Ca^{2+}$ channel current, the effect of the compounds are tested on the R-type $Ca^{2+}$ channel amplitude, voltage dependency and probability of opening, by using the cell-attached patch clamp technique (Bkaily 1994, supra; 1996, supra) and intra and extra patch pipette application of the drug. In all experiment using single channel recording, nifedipine ($10^{-6}M$) was present in the control and experimental solutions.

Recent results have recently demonstrated that some cardiogenic and vasoconstrictor hormones such as PAF, ET-1 and bradykinin induced a sustained increase of cytosolic as well as nuclear calcium (data not shown). This sustained increase of $Ca^{2+}$ induced by depolarization of the cell membrane or hormones such as PAF, ET-1 and bradykinin is due to the increase of $Ca^{2+}$ influx through the R-type $Ca^{2+}$ channels at the sarcolemmal membrane and/or the nuclear membrane (Bkaily G., 1994, supra; 1996, supra; 1997a–d, supra). Using $Ca^{2+}$ fluorescence probes Fura-2 or Fluo-3 and 2 and three-dimension $Ca^{2+}$ imaging techniques (Bkaily G., 1994, supra; 1996, supra; 1997a–d, supra), the effect of hormones and drugs could be easily tested. These two methods are used with single cells of different types as described above.

The effects of the compounds of the present invention on cytosolic and nuclear $Ca^{2+}$ in different conditions ($K^+$ depolarization, PAF, ET-1, etc.) that increase the probability of opening of the R-type $Ca^{2+}$ channels and induce cytosolic and/or nuclear $Ca^{2+}$ overload (in presence of L-type $Ca^{2+}$ blocker, nifedipine) were tested.

Using Fura-2 or Fluo-3 cytosolic and nuclear $Ca^{2+}$ measurement techniques, the inventors also tested the effect of the compounds of the invention on the spontaneous increase of cytosolic and nuclear $Ca^{2+}$ during spontaneous contraction of ventricular single cells. Single cells from human fetal ventricular cells and chick embryonic cells were bathed in normal Tyrode's solution and spontaneous intracellular $Ca^{2+}$ transient recorded in the absence and the presence of the compounds of the invention.

EXAMPLE 7

Effects of MV8608 on TTX-Sensitive Fast $Na^+$ Current

Figure 11:
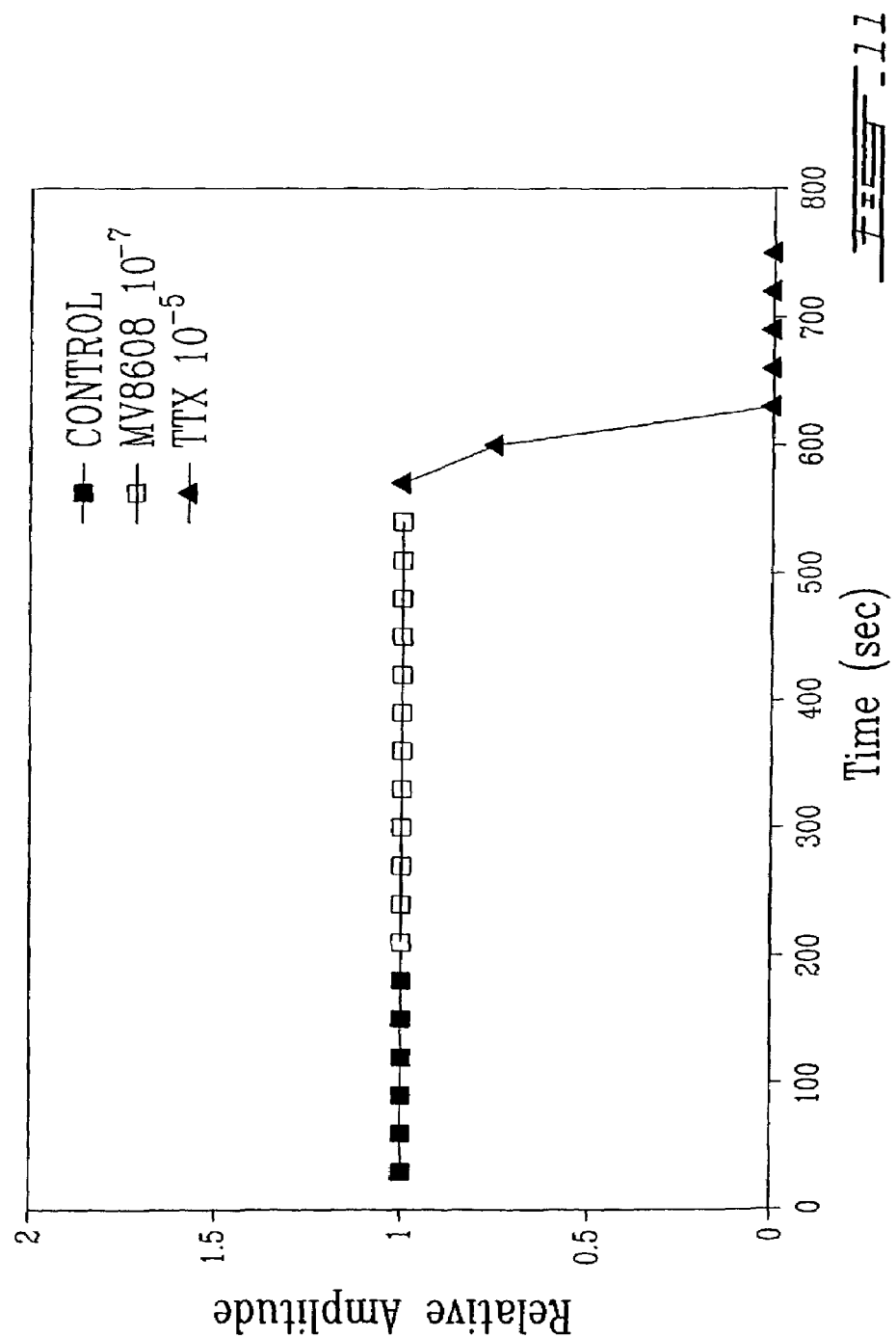
FIG. 11 shows the absence of the effect of ($10^{-7}$M) of MV8608 on the TTX-sensitive fast $Na^+$ current in single heart cell.

In one series of experiments (n=5), the effect of different concentrations of MV8608 ($10^{-11}$M to $10^{-7}$M) on the TTX-sensitive fast $Na^+$ current were tested using the whole-cell voltage clamp technique and experimental conditions reported elsewhere (Bkaily et al., 1988, supra; 1993, supra). MV8608 was found to have no effect on the TTX-sensitive fast $Na^+$ current at all concentrations used and FIG. 11 shows an example using a concentration of $10^{-7}$M.

Thus, MV8608 had no effect on the fast $Na^+$ current and cannot be used as a depressor or blocker of this channel where its reduction has a therapeutic action such as the case of several local anesthetics and antiarrythmic drugs such as Lidocaine.

EXAMPLE 8

Effect of MV8608 on T-Type $Ca^{2+}$ Current

Figure 12:
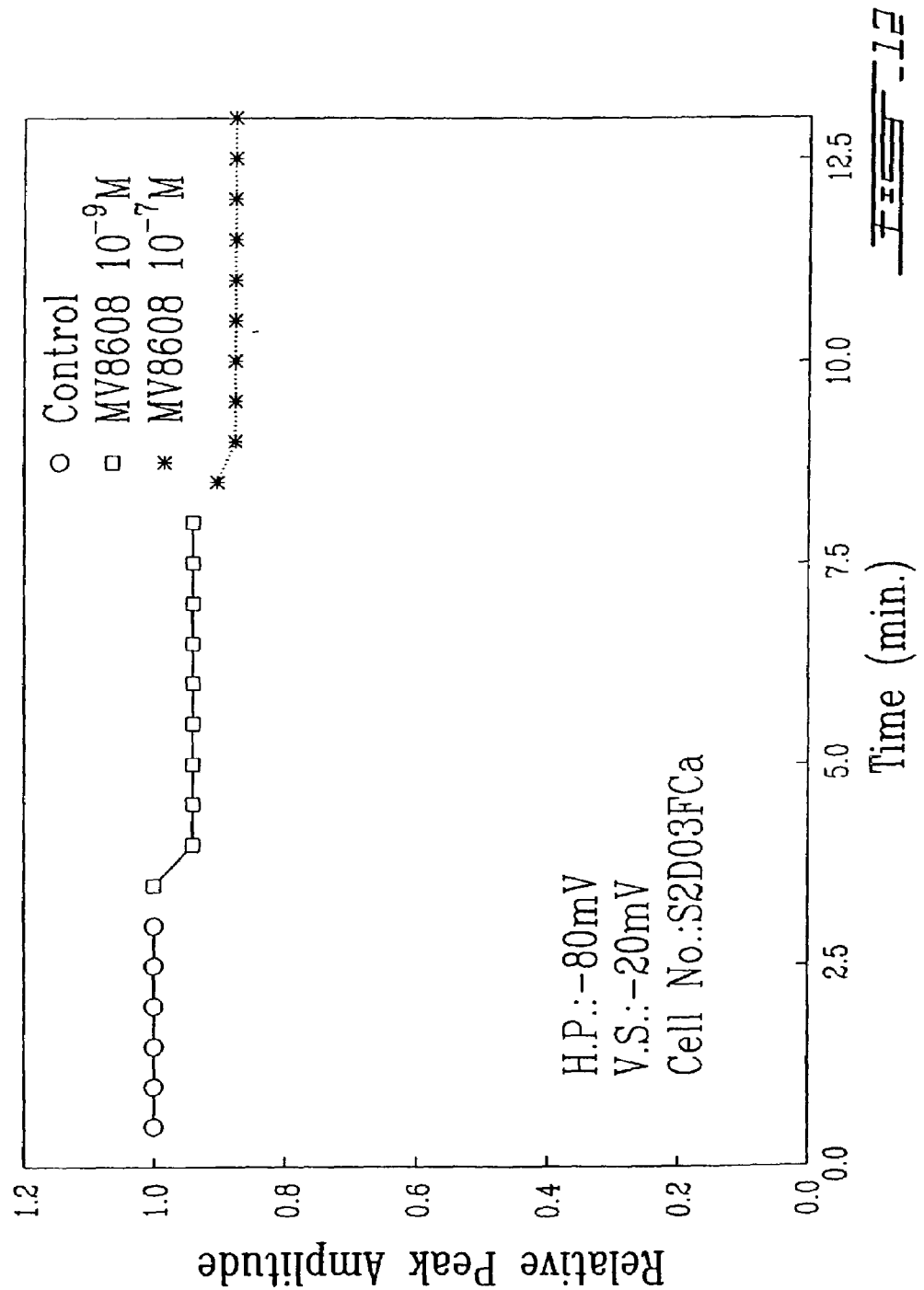
FIG. 12 shows the relative weak depressing effect of ($10^{-9}$M) and ($10^{-7}$M) of MV8608 on the T-type $Ca^{2+}$ current in heart cells.

In another series of experiments (n=7), the effect of different concentrations of MV8608 were tested on the T-type $Ca^{2+}$ current ($I_{Ca}$) using the whole-cell voltage clamp technique and classical experimental conditions described elsewhere by the inventors (Bkaily G. et al., 1991, supra; 1992, supra; 1993, supra). MV8608 had no effect on the T-type $I_{Ca}$ amplitude at a concentration of $10^{-9}$M to $10^{-7}$M and FIG. 12 shows an example. As it can be seen in that figure, the inset effect of MV8608 in T-type $I_{Ca}$ is immediate. Thus, the MV8608 was found to be a very weak depressor of the T-type $I_{Ca}$.

These results suggest that MV8608 cannot be used as a potent blocker of the T-type $Ca^{2+}$ channel and in a therapeutic action, wherein its blockade is involved. However, the depressing effect of MV8608 on the T-type $I_{Ca}$ could be useful for example, in combination with other drugs to suppress ventricular tachycardia and fibrillation.

EXAMPLE 9

Effect of MV8608 on L-Type $Ca^{2+}$ Channel

Figure 13:
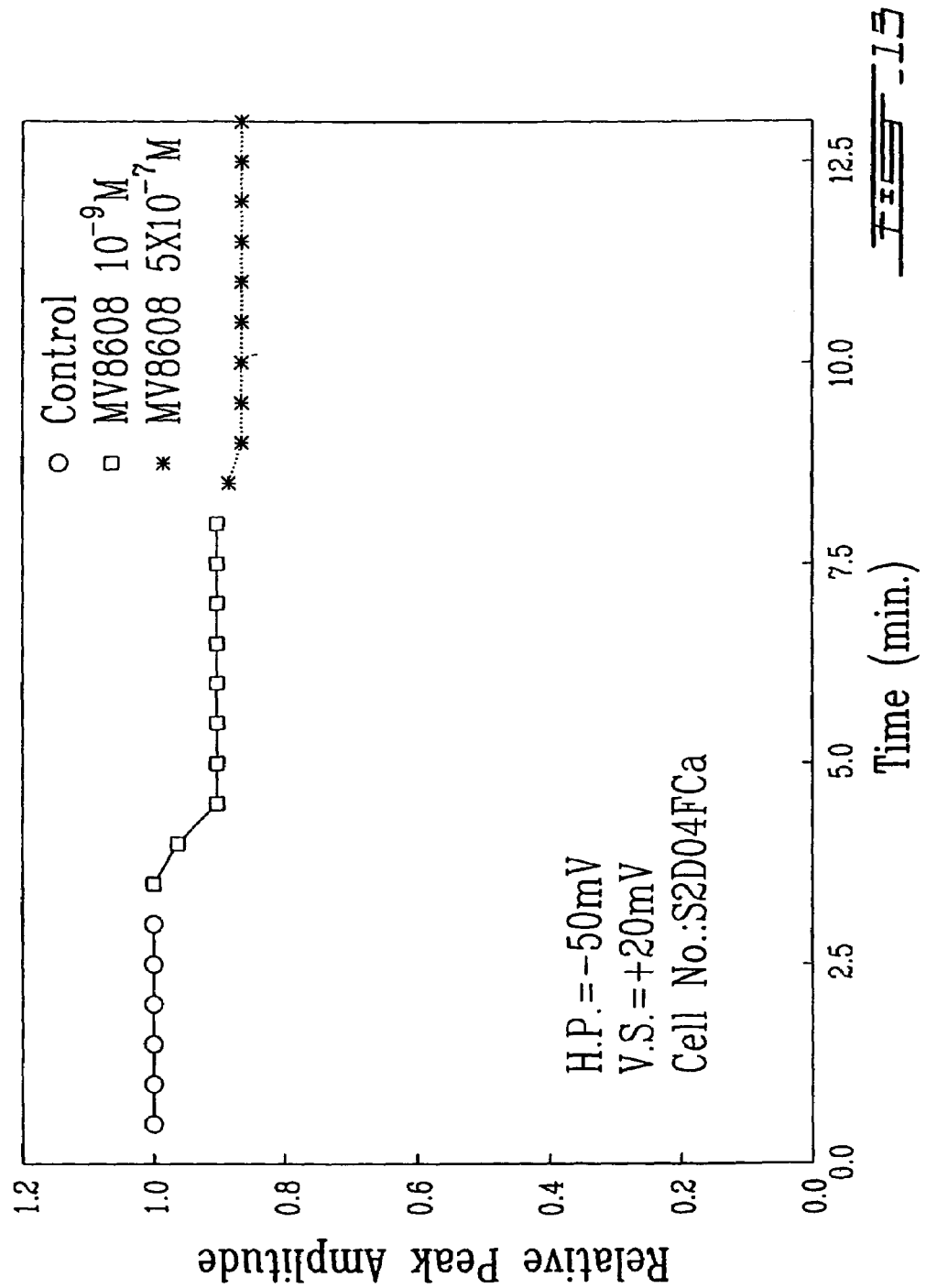
FIG. 13 shows the relative weak depressing effect of ($10^{-9}$M) and $5\times(10^{-7}$M) of MV8608 on the L-type $Ca^{2+}$ current in heart cells.

In another series of experiments (n=5), the effect of different concentrations of MV8608 ($10^{-11}$ to $10^{-6}$M) were tested on the L-type $I_{Ca}$ of heart cells of chick embryos using the whole-cell and experimental conditions and protocols described elsewhere by the inventors (Bkaily G. et al., 1993, supra). As for the T-type $I_{Ca}$, the L-type $I_{Ca}$ was not affected by $10^{-11}$ to $10^{-10}$M MV8608. However, increasing the concentration of the compound up to $10^{-9}$M decreased the $I_{Ca}$ amplitude by 10% and a further slight increase was found at a concentration of $5\times10^{-7}$M of MV8608. FIG. 13 shows a typical experiment of the time course effect of the $10^{-9}$ and $5\times10^{-7}$M concentrations of MV8608.

These results show that MV8608 is a very weak depressor of the L-type $Ca^{2+}$ channel. Thus MV8608 cannot be considered as a high potent antagonist of the L-type $Ca^{2+}$ channel but its depressor effect could be useful when used in combination with known L-type $Ca^{2+}$ antagonist drugs. The weak depressor effect of MV8608 on the T-type $Ca^{2+}$ channel along with the L-type $Ca^{2+}$ channel would be highly beneficial for the treatment of ventricular tachycardia, fibrillation and pathology, where the L-type $Ca^{2+}$ blockers are known and clinicaly used.

EXAMPLE 10

Effect of MV8608 on R-Type $Ca^{2+}$ Channel

Figure 14:
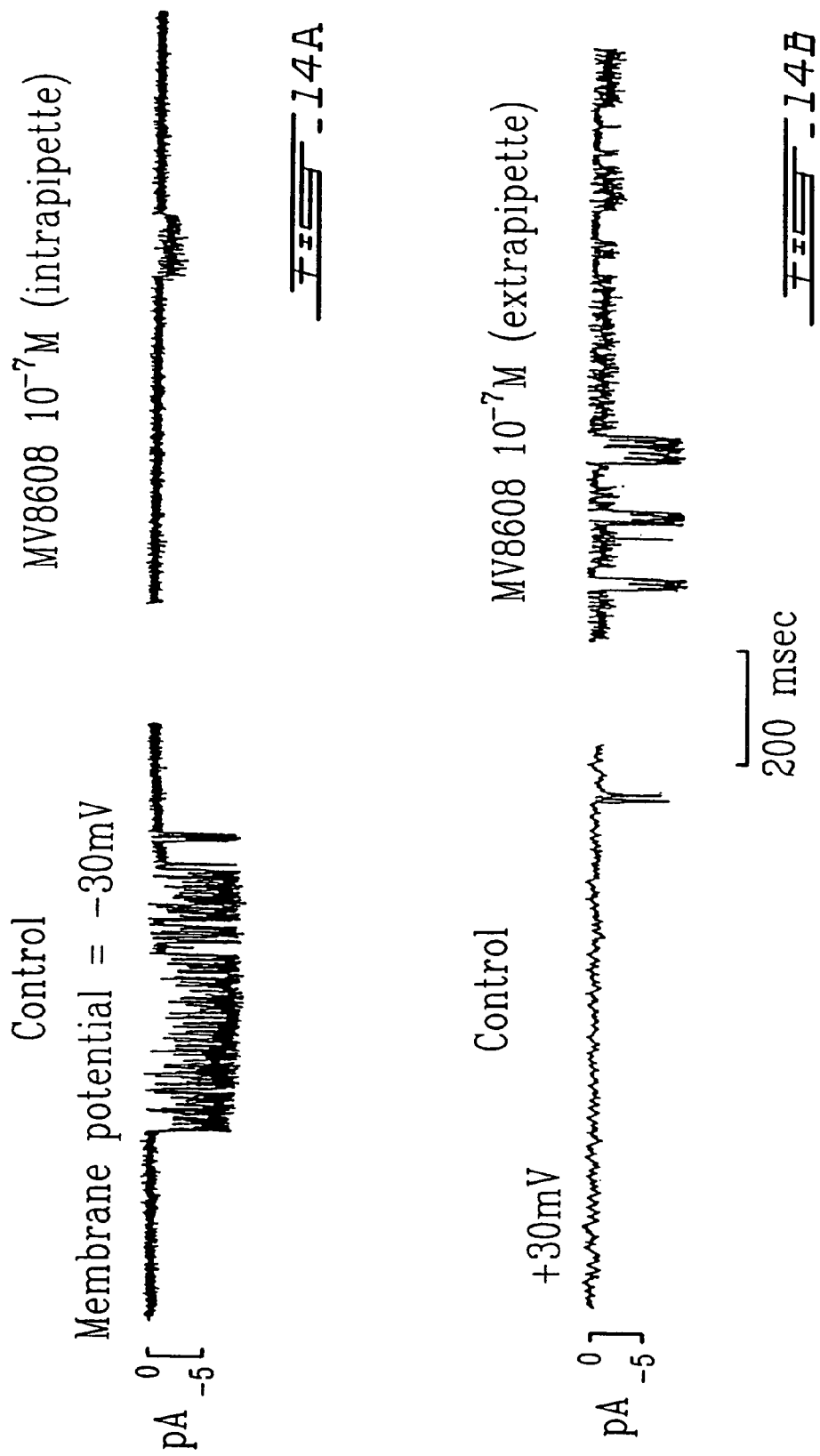
FIG. 14 shows that intra patch pipette application of ($10^{-7}$M) of MV8608 decreased the R-type $Ca^{2+}$ channel amplitude and probability of opening and that extra patch pipette application of MV8608 ($10^{-7}$M) increased the time of opening duration followed by transient decrease of the amplitude of the R-type $Ca^{2+}$ channel.

In another series of experiments (n=7), using the cell attached patch clamp technique (Bkaily G. 1994, supra; Bkaily G. et al., 1996, supra), the effect of $10^{-7}$M of MV8608 on the R-type $Ca^{2+}$ channel in human aortic vascular smooth muscle cell line was tested. In one series of experiments (n=4), in the presence of $10^{-6}$M of nifedipine ($10^{-6}$M) in the patch pipette solution containing 110 mM $Ca^{2+}$, $10^{-7}$M of MV8608 was applied to the pipette. MV8608 applied in the patch pipette solution decreased the single channel amplitude and probability of opening of the single R-type $Ca^{2+}$ channel under the patch pipette without affecting its single channel conductance. In a second series of experiments (n=3), the patch pipette solution was free of MV8608 and after recording the single channel activities at different voltages, MV8608 (final concentration of $10^{-7}$M) was applied to the extra-patch pipette solution containing 140 mM KCl (where the rest of the cell is bathing). This experiment was designed to verify whether MV8608 crossed the cell membrane and if so, whether its effect from the internal side of the channel under the patch is the same as that when applied at the outer side thereof. The results showed that MV8608 did indeed cross the cell membrane. However, instead of decreasing permanently the amplitude and probability of opening of the single R-type channel as did the intra-patch pipette application, the action of MV8608 on the inner side of the membrane increased the probability and duration of opening of the R-type channel. This was accompanied by a spontaneous decrease and release of the blockade of the single channel current. FIG. 14 shows a typical single R-type $Ca^{2+}$ channel current in absence and presence of extra-patch pipette $10^{-7}$M of MV8608. Such a pattern of increase of probability of opening and the open duration accompanied with the sporadic decrease of the single channel current amplitude has never been observed when MV8608 was applied at the outer side of the single channel under the patch pipette.

These results highly suggest that the blocking action of MV8608 on R-type $Ca^{2+}$ channel is located mainly at the outer side of the channel. Furthermore, it strongly suggests that its capability of crossing the cell membrane enables the compound to increase fleckering and duration of opening of the channel which in turn makes the external inhibitory site of the channel accessible to the external molecules of MV8608. Taken together, these results highly suggest that the inhibitory action of MV8608 requires the R-type $Ca^{2+}$ channel to be in the open state (overstimulated) and also depends on the frequency of opening of the R-type $Ca^{2+}$ channel. This may explain, at least in part, the preventive as well as therapeutic action of MV8608, on the overstimulation of the R-type $Ca^{2+}$ channel as will be shown below using Fura-2 and Fluo-3 $Ca^{2+}$ measurement techniques.

These results demonstrate that MV8608 does block efficiently the R-type $Ca^{2+}$ at the open state of the channel (i.e. in state of overstimulation). The blockade of the R-type $Ca^{2+}$ by MV8608 should reduce the sustained $Ca^{2+}$ overload that occurred during many abnormal cell function such as for example sustained vasoconstriction and hormone secretion, self-perpetuating hormone secretion of spontaneously active proliferating cells in atherosclerosis, cancer cells proliferation, acute immuno-reaction, arthritis inflammation, pain, ischemia-reperfusion, asthma, acute bronchoconstruction, arrythmia, fibrillation, septic shock and epiptosis.

EXAMPLE 11

Effect of MV8608 on R-Type $Ca^{2+}$ Channel Under Sustained Activation Thereof.

Figure 16:
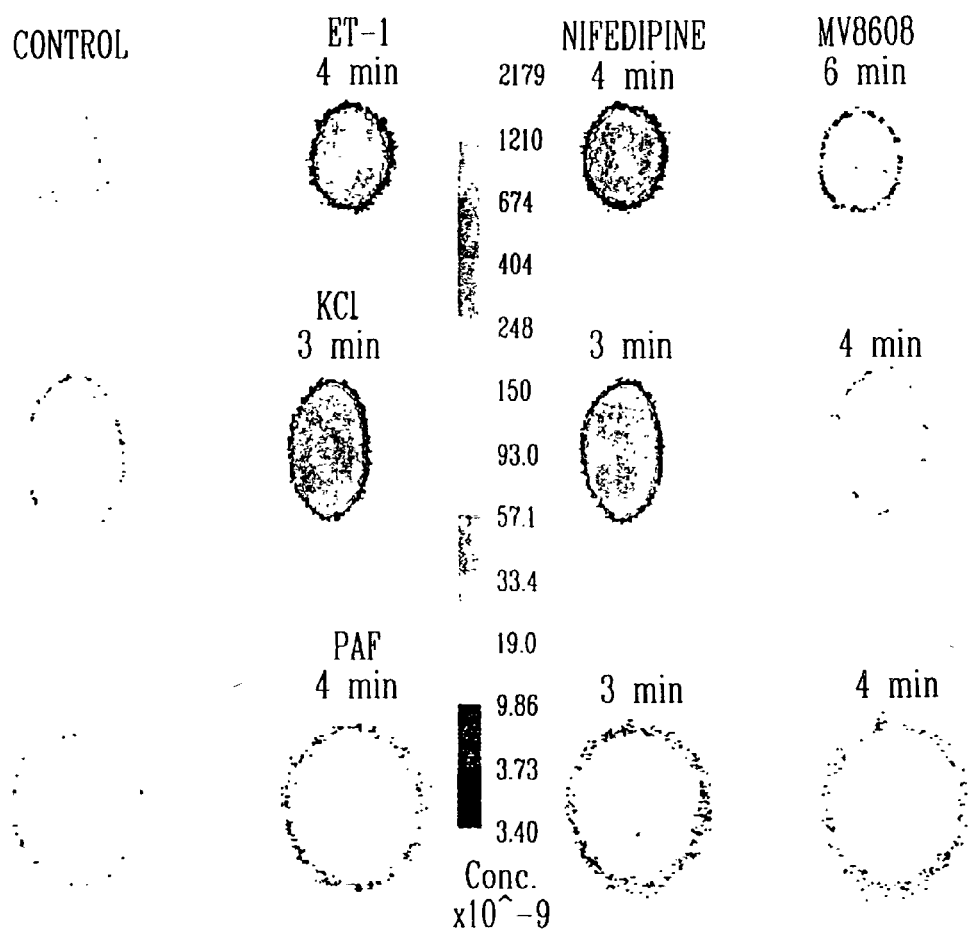
FIG. 16 shows the absence of the effect of nifedipine ($10^{-6}$M) on ET-1 ($10^{-9}$M), sustained depolarization (KCl, 30 mM) and PAF ($10^{-9}$M) induced sustained increase of [Ca] via the activation of the R-type $Ca^{2+}$ channel and the blockade of this sustained increase by MV8608 ($10^{-9}$M) in heart cells.
Figure 17:
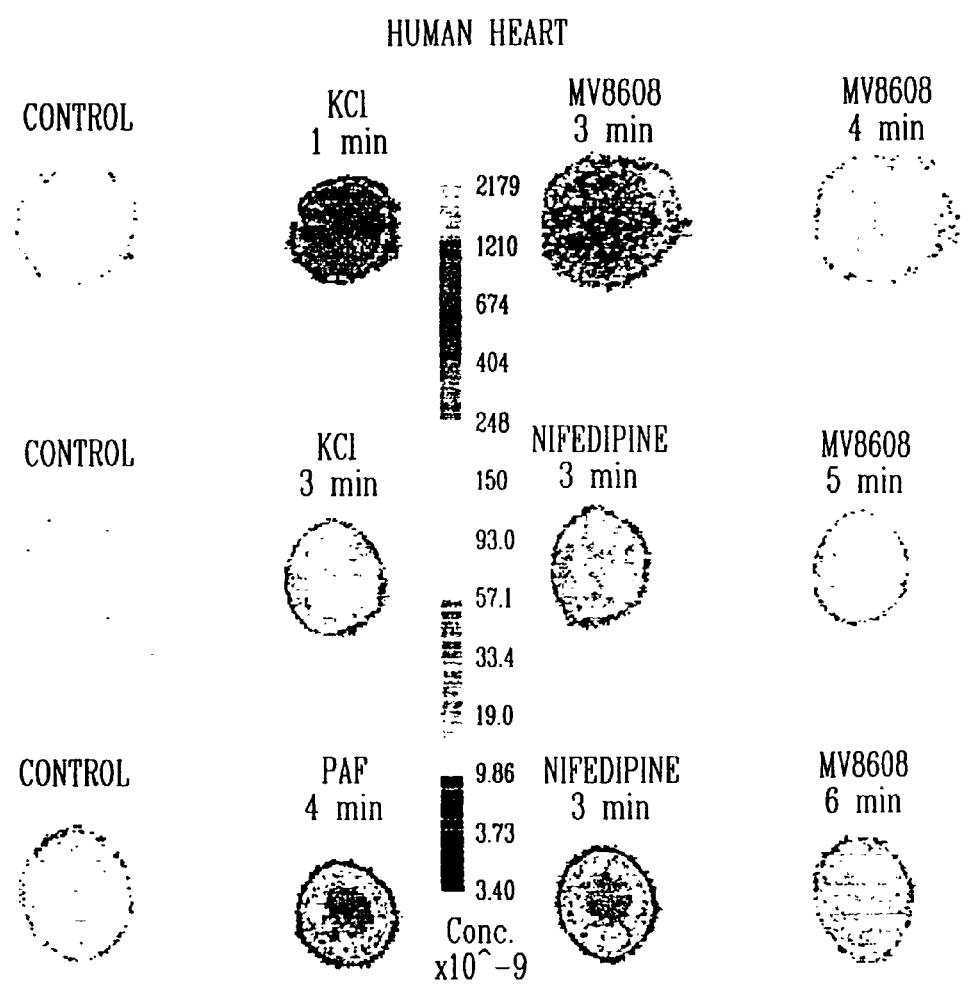
FIG. 17 shows the blockade by MV8608 ($10^{-9}$M) and the absence of the effect of nifedipine ($10^{-6}$M) on the sustained depolarization (30 mM), and PAF ($10^{-9}$M) induced sustained increase of $[Ca]_i$ via activation of the R-type $Ca^{2+}$ channel in human heart cells.
Figure 21:
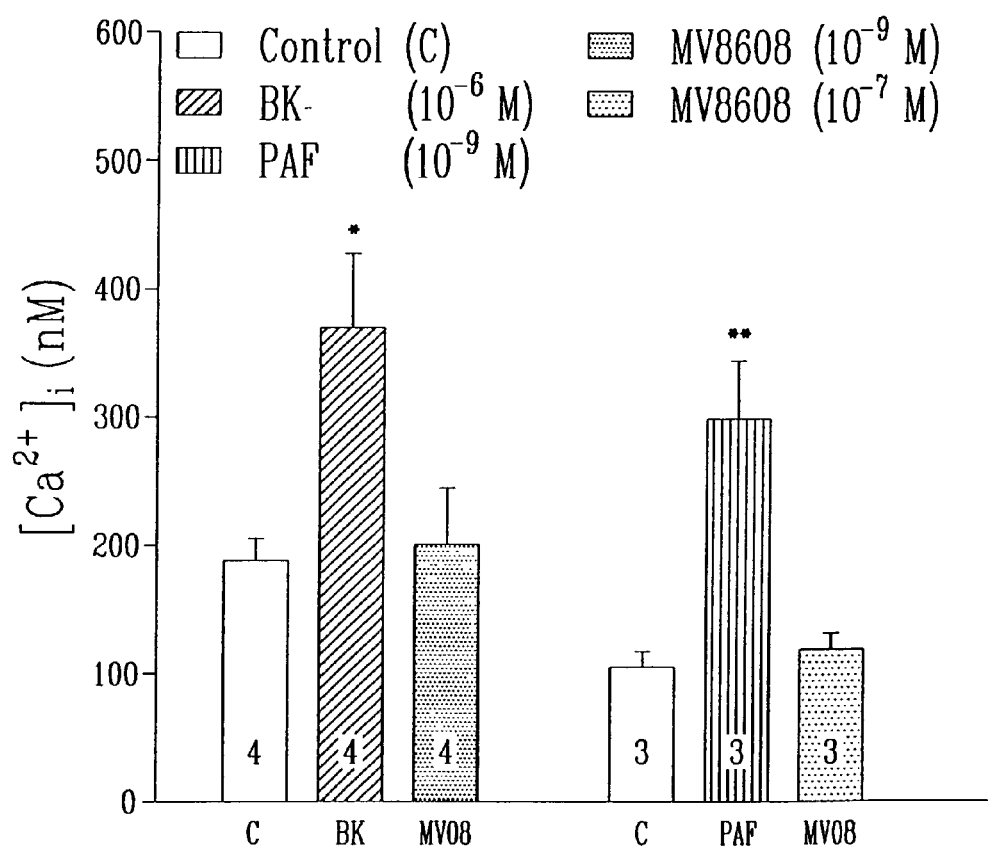
FIG. 21 represents histograms showing the MV8608 ($10^{-9}$M) blockade of bradykinin (BK $10^{-6}$M) and PAF ($10^{-9}$M) induced sustained increase of $[Ca]_i$ via activation of the R-type $Ca^{2+}$ channels in rabbit aortic vascular smooth muscle cells.
Figure 22:
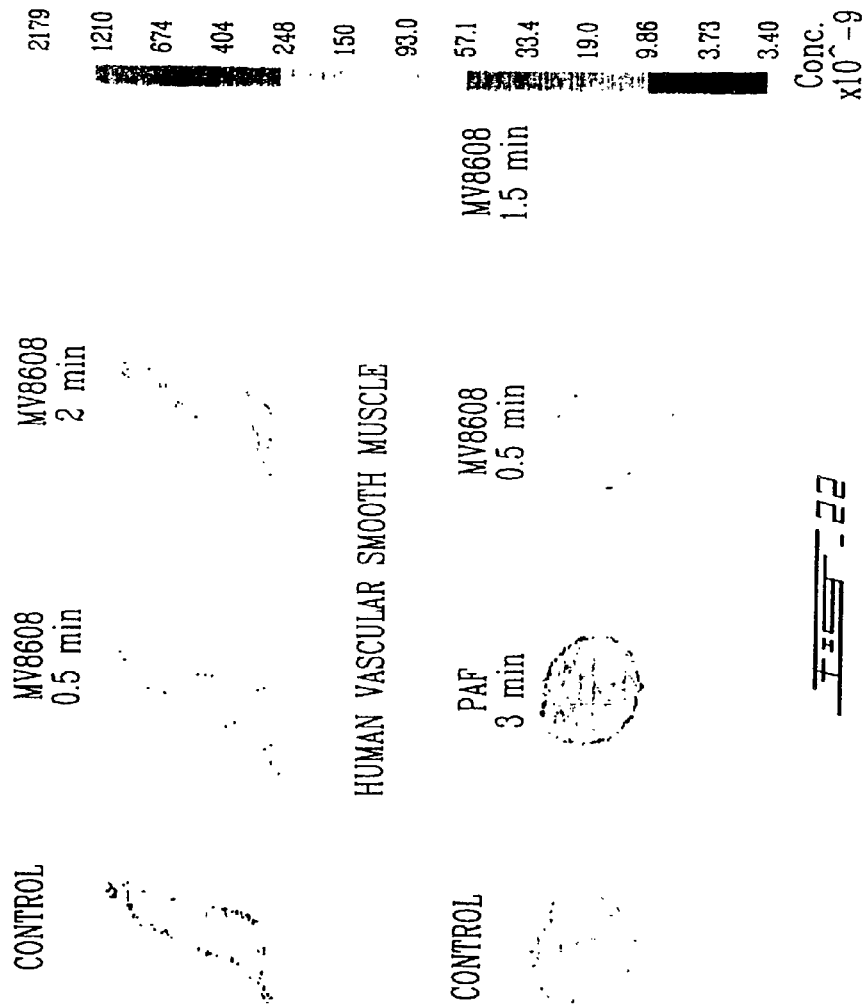
FIG. 22 shows a typical example of the decrease of basal sustained increase of $[Ca]_i$ by MV8608 ($10^{-9}$M) in freshly isolated human aortic endothelial cells and the blockade by MV8608 ($10^{-9}$M) of PAF ($10^{-9}$M) induced sustained increase of $[Ca]_i$ via activation of the R-type $Ca^{2+}$ channels in freshly isolated human aortic vascular smooth muscle cells.

In another series of experiments we tested the effect of MV8608 ($10^{-9}$M) on R-type $Ca^{2+}$ channels stimulation-induced sustained increase of total intracellular $Ca^{2+}$ by sustained depolarization (FIGS. 15 to 19), by PAF ($10^{-9}$M) (FIGS. 16 to 19 and 21 to 22), by ET-1 ($10^{-9}$M) (FIGS. 16 and 19) and bradykinin (BK, $10^{-6}$M) (FIGS. 20 and 21), in embryonic chick heart cells (FIGS. 15, 16, 19 and 20), 19-week-old human fetal heart cells (FIGS. 15, 17, 18 and 20), rabbit aortic vascular smooth muscle (VSM) cells (FIGS. 20 and 21), human aortic VSM cell-line (FIG. 23) and freshly isolated (FIG. 22) as well as in freshly isolated aortic endothelial cells (FIG. 22).

Figure 18:
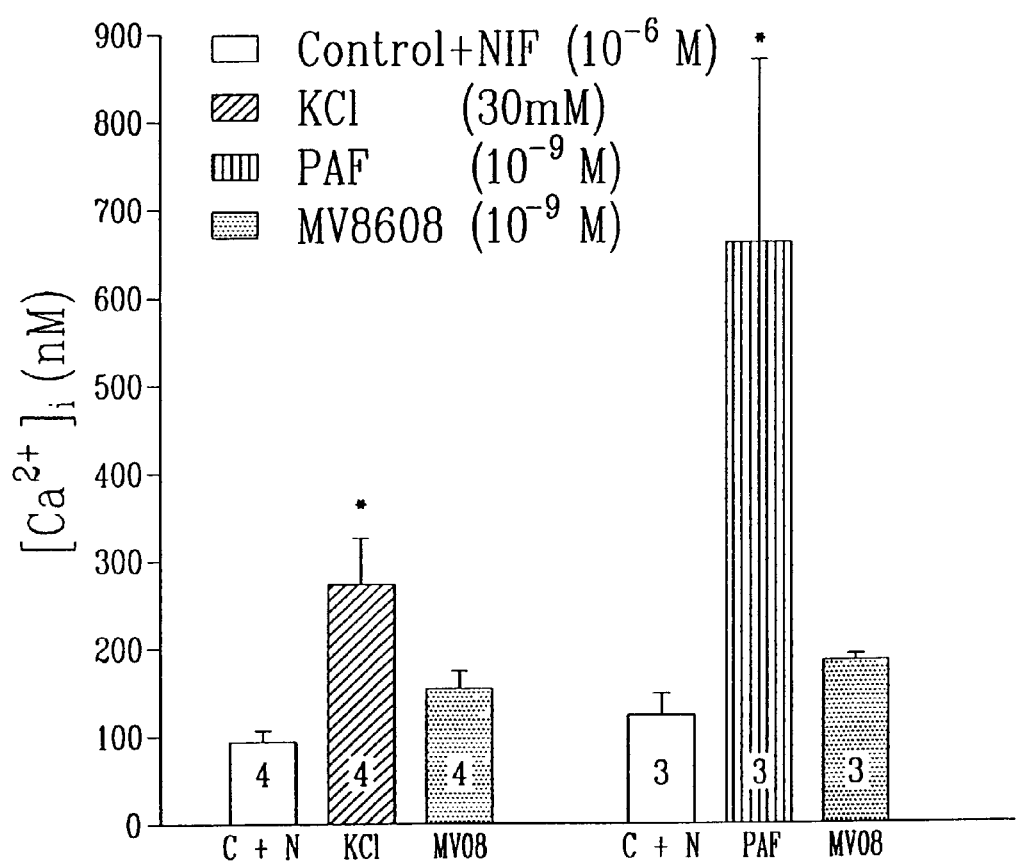
FIG. 18 represents histograms showing MV8608 ($10^{-9}$M) blockade of sustained increase of $[Ca]_i$ (in presence of nifedipine (C+N) induced by sustained depolarization (KCl, 30 mM) and PAF ($10^{-9}$M) stimulation of the R-type $Ca^{2+}$ channel in human heart cells.
Figure 19:
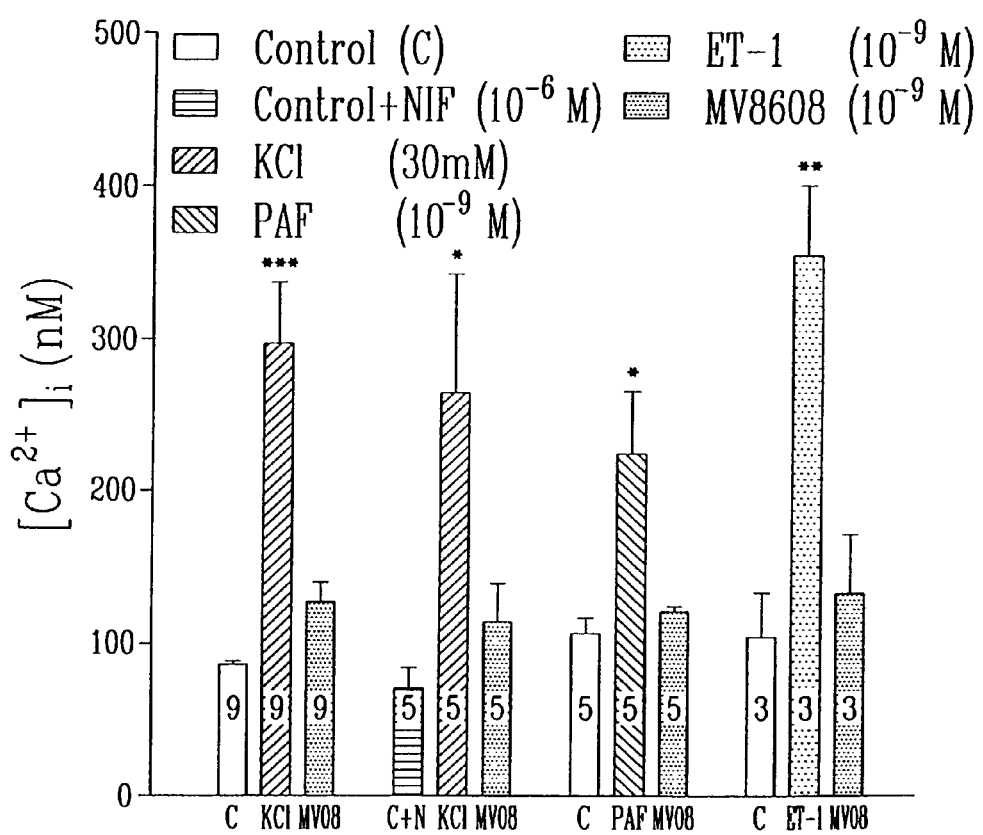
FIG. 19 represents histograms illustrating MV8608 ($10^{-9}$M) blockade of the sustained increase of [Ca], induced by sustained depolarization (in presence or absence of nifedipine), PAF and ET-1 stimulation of R-type $Ca^{2+}$ channel in chick heart cells.
Figure 20:
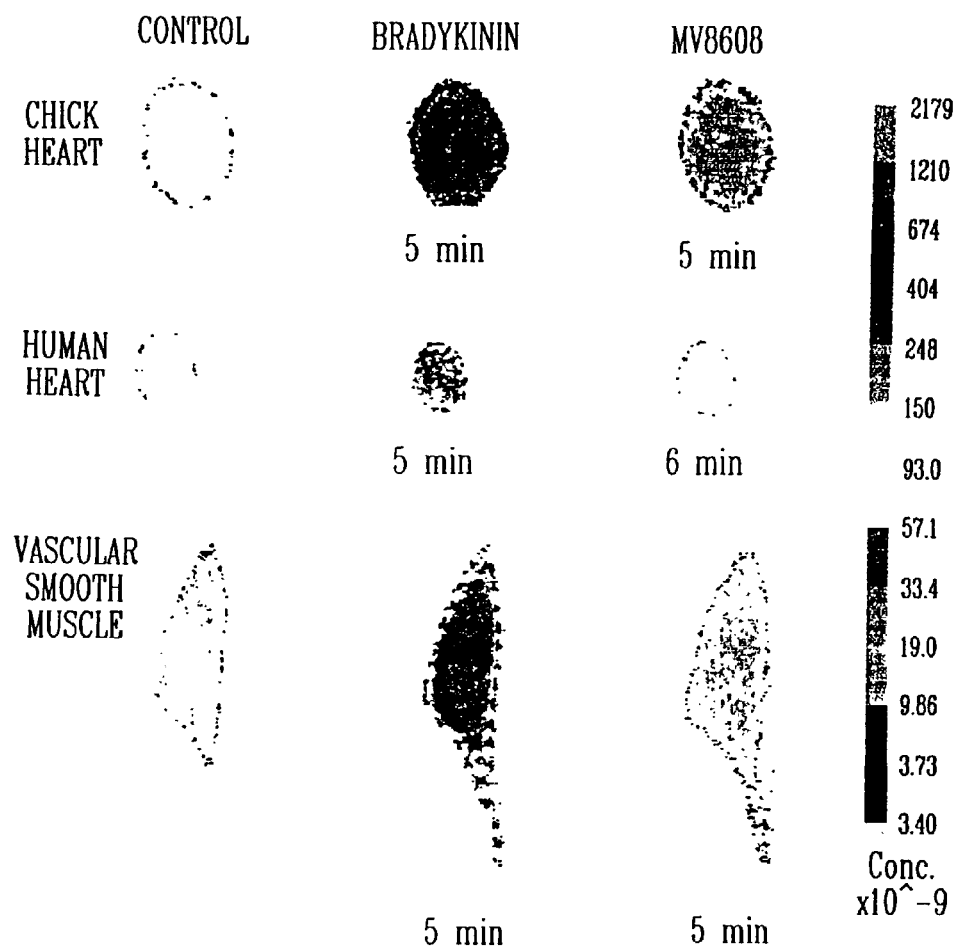
FIG. 20 shows the blockade by MV8608 ($10^{-9}$M) of bradykinin ($10^{-6}$M) induced sustained increase of [Ca], (in presence of ($10^{-6}$M) nifedipine) via activation of the R-type $Ca^{2+}$ channels in chick heart cells, human heart cells and rabbit aortic vascular smooth muscle cells.

As can be seen in these results, sustained activation of the R-type $Ca^{2+}$ channel induced by a sustained increase of $[Ca]_i$ induced by a sustained depolarization or sustained superfusion with a relatively low concentration of a hormone such as ET-1 ($10^{-9}$M), PAF ($10^{-9}$M) and high concentration BK ($10^{-6}$M), was completely blocked by $10^{-9}$M of MV8608 and this effect occurred within 4 to 5 min in the presence of the R-type $Ca^{2+}$ blocker. In addition, these results showed that the pure L-type blocker, nifedipine ($10^{-7}$M to $10^{-5}$M) had no effect on the R-type $Ca^{2+}$ channel or on the sustained increase of $[Ca]_i$-induced stimulation of the R-type $Ca^{2+}$ channel (FIGS. 16 to 23). Furthermore, the pure L-type $Ca^{2+}$ channel blocker did not prevent MV8608 from blocking the stimulation of R-type $Ca^{2+}$ channel induced sustained increase of $[Ca]_i$ (FIGS. 18 and 19). In some experiments, the stimulation of the R-type $Ca^{2+}$ channel was elevated by increasing the concentration of PAF from $10^{-9}$M up to $10^{-7}$. Under such conditions, 10 $M^9$ of MV8608 failed to significantly decrease the sustained increase of $[Ca]_i$ induced by $10^{-7}$M PAF. Only a concentration of $10^{-6}$M of MV8608 was able to block the high PAF effect on the sustained increase of $[Ca]_i$ (FIG. 23).

Figure 28:
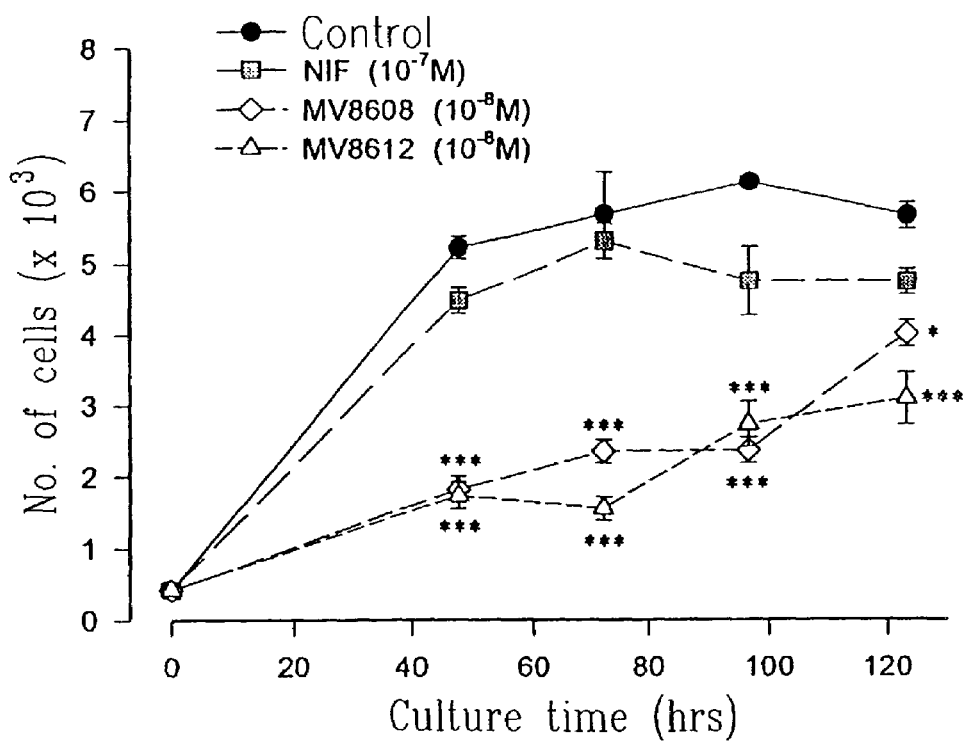
FIG. 28 represents graphs showing that both MV8608 ($10^{-8}$M) and MV8612 ($10^{-8}$M) but not nifedipine ($10^{-7}$M) significantly decreased the spontaneous proliferation of human aortic vascular smooth muscle cell line.

Taken together, these results demonstrate that MV8608 blocked the R-type $Ca^{2+}$ channel in all cell types used including the human osteoblast cancer cell lines (MG63 and FAOS-2), human VSM cells isolated from atherosclerotic patients, arterial and venous endothelial cells, endocardic endothelial cells, T-lymphocytes and platelets (not shown) and spontaneously proliferative human aortic vascular smooth muscle cells, AOSMC-9 (FIG. 28).

Figure 29A:
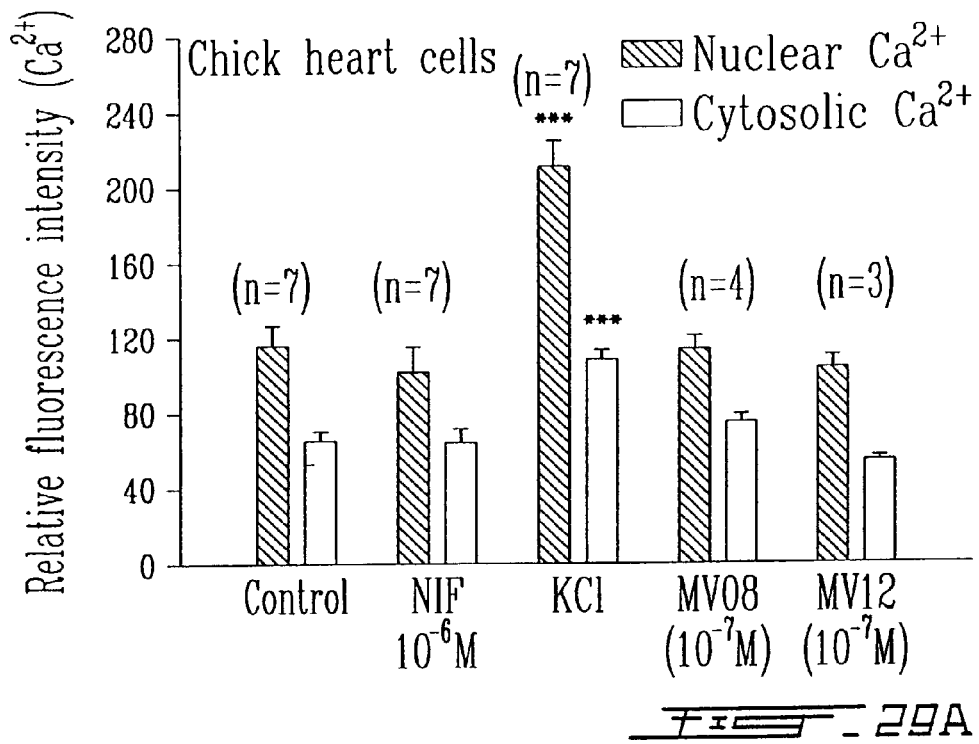
FIG. 29 represents histograms showing that the L-type $Ca^{2+}$ blocker, nifedipine did not affect basal cytosolic ([ ]$_c$) and nuclear ([ ]$_n$) free $Ca^{2+}$ as well as the sustained depolarization and high PAF induced sustained increase of $[Ca]_c$ and $[Ca]_n$. However, MV8608 and MV8612 blocked completely the sustained depolarization induced sustained increase of $[Ca]_c$ and $[Ca]_n$ (panel A) in heart cells. Panel B shows that high concentration of PAF ($10^{-7}$M) induced sustained increase of $[Ca]_c$ and $[Ca]_n$ is blocked by high concentration of MV8608 ($10^{-6}$M) but normal concentration of MV8612 ($10^{-8}$M)
Figure 29B:
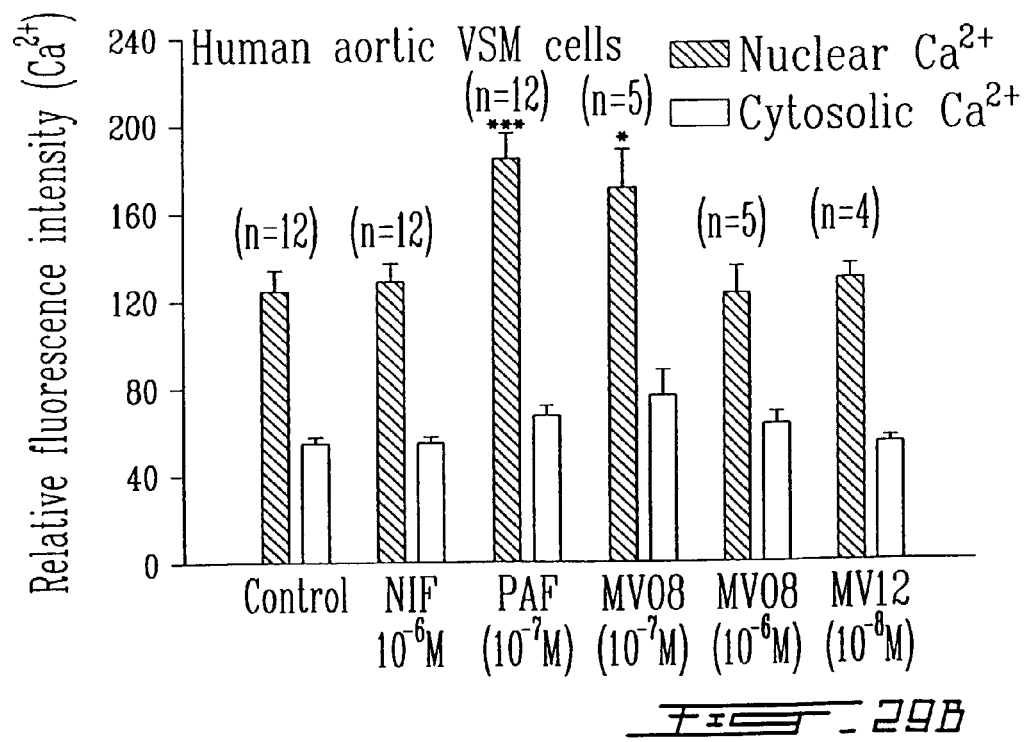
Figure 30:
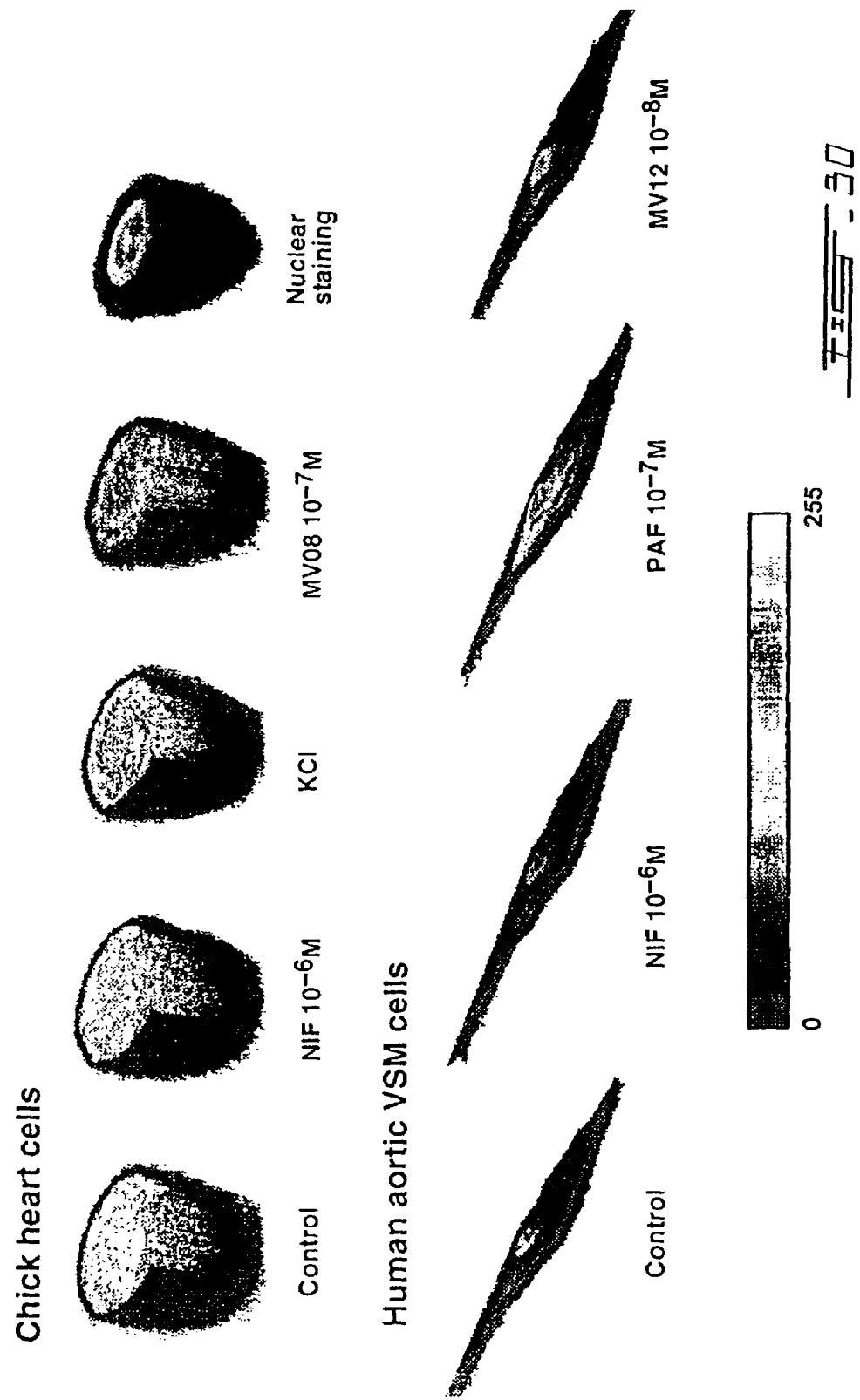
FIG. 30 is a 3-dimensional reconstitution showing the absence of effect of nifedipine and the blockade of the sustained increase of $[Ca]_c$ and $[Ca]_n$ induced by sustained depolarization and high PAF ($10^{-7}$M) in chick heart (A) and human aortic vascular smooth muscle cell line (B)

In another series of experiments confocal microscopy was used with Fluo-3,3-dimension $Ca^{2+}$ measurement techniques in order to verify if the blockade of the R-type $Ca^{2+}$ channel by MV8608 could block both the sustained increase of cytosolic ($[\ ]_c$) and (nuclear ($[\ ]_n$) free $Ca^{2+}$ induced by the stimulation of the R-type $Ca^{2+}$ channels induced by a sustained increase of $[Ca]_i$. As can be seen in FIGS. 29 and 30, and as previously reported (Bkaily et al., 1996a, supra), in presence of nifedipine, sustained depolarization with 30 mM KCl and PAF induced a sustained increase of both $[Ca]_c$ and $[Ca]_n$ (largely nuclear). The MV8608 blocked both the cytosolic and nuclear $Ca^{2+}$ sustained overload with a concentration of $10^{-7}$M. As was shown using the Fura-2 total $[Ca]_i$ measurement technique, only at $10^{-6}$M did the compound significantly decrease the sustained increase of $[Ca]_c$ and $[Ca]_n$ induced with high concentration of PAF ($10^{-7}$M) back to the control level (FIG. 29B). In addition to its blocking of the depolarization induced sustained increase of $[Ca]_i$ MV8608, at a concentration of $10^{-8}$ M and $10^{-7}$ M, prevented the stimulation of the R-type $Ca^{2+}$ channel by the sustained depolarization in a dose-dependent fashion, thus decreasing back the $[Ca]_c$ and $[Ca]_n$ to the control level (FIG. 29A). Extracellular applications of the $Ca^{2+}$ chelator EGTA further decreased the $[Ca]_i$ mainly at the nucleus level.

These results demonstrate that blockade of the R-type $Ca^{2+}$ by MV8608 blocked both $[Ca]_c$ and $[Ca]_n$ sustained overload. In contradistinction to what was shown for high PAF ($10^{-7}$ M) induced sustained increase of $[Ca]_i$, $[Ca]_c$ and $[Ca]_n$, MV8608 succeeded in preventing the high PAF action at a concentration of $10^{-9}$M. Thus, this compound seems to be equally effective in acute sustained $Ca^{2+}$ overload, however, it is more effective as a preventive blocker of the R-type $Ca^{2+}$ channel in chronic overstimulation of the channel.

Taken together, these results showed that MV8608 is a more effective R-type $Ca^{2+}$ channel blocker in acute rather than in chronic situations. However, it seems to be more effective in preventing rather than treating a chronic stimulation of $Ca^{2+}$ influx through the R-type $Ca^{2+}$ channel. Non-limiting examples of acute situations include septic shock, acute asthma attacks and bronchospasm. Non-limiting examples of chronic situations include cystic fibrosis, rheumatoid arthritis, pulmonary oedema and hypertension caused by arteriosclerosis.

Figure 24A:
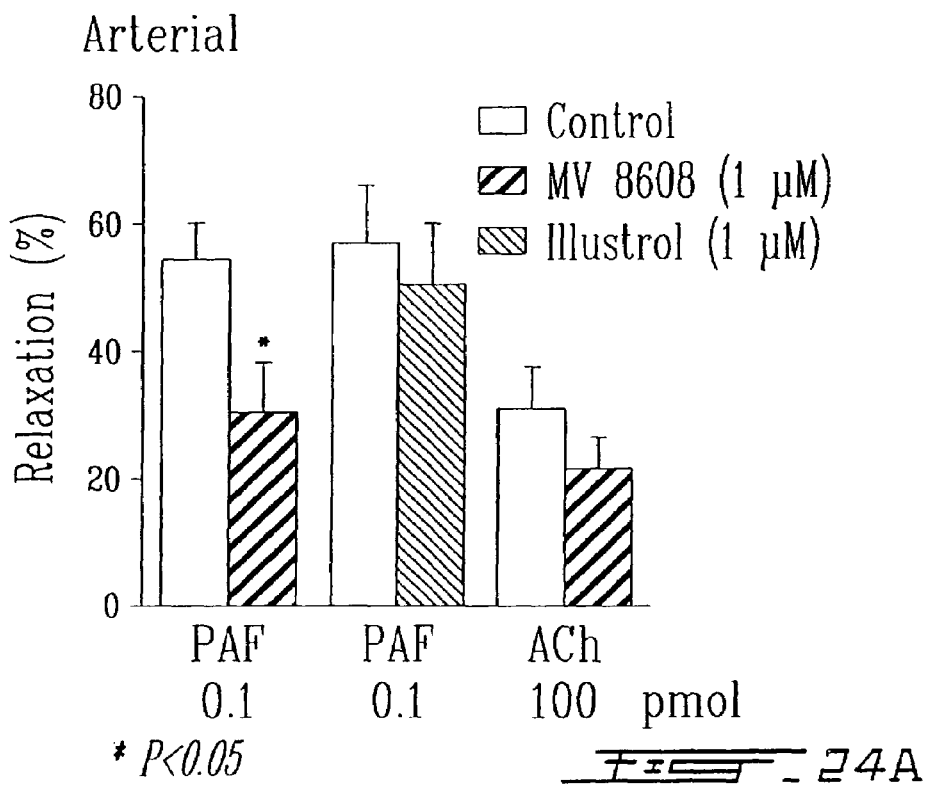
FIG. 24 represents histograms showing that in double-perfused mesenteric bed of the rat, MV8608 (1 µM) but not Illusteol (1 µM) blocked PAF but not ACh and AngII induced arterial vasodilatation and venconstriction.
Figure 24B:
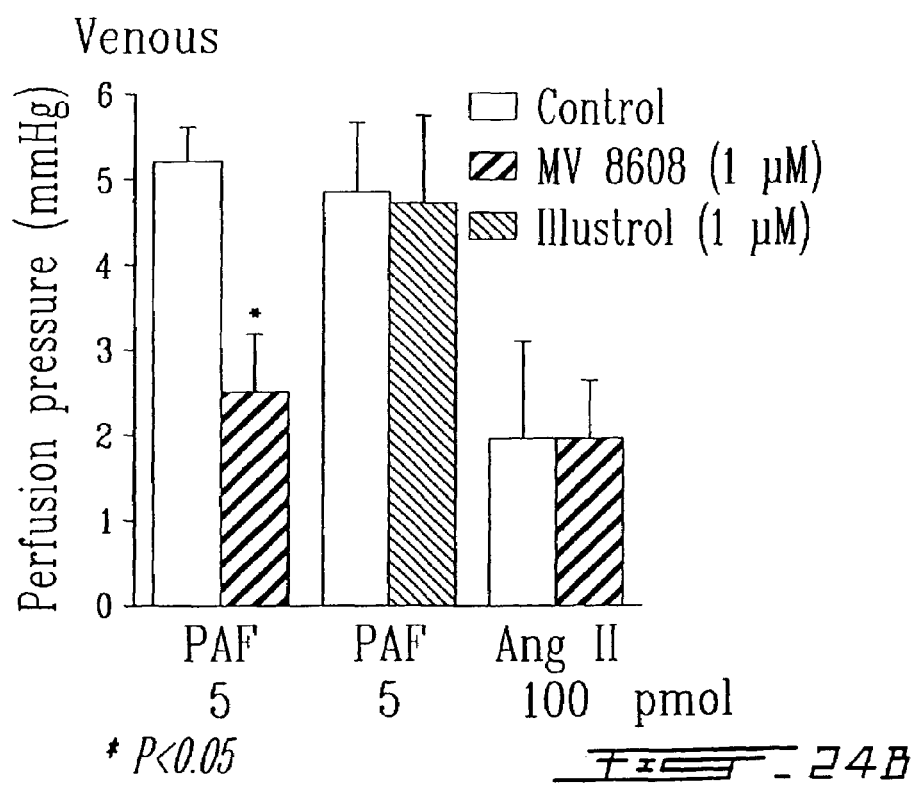
Figure 25:
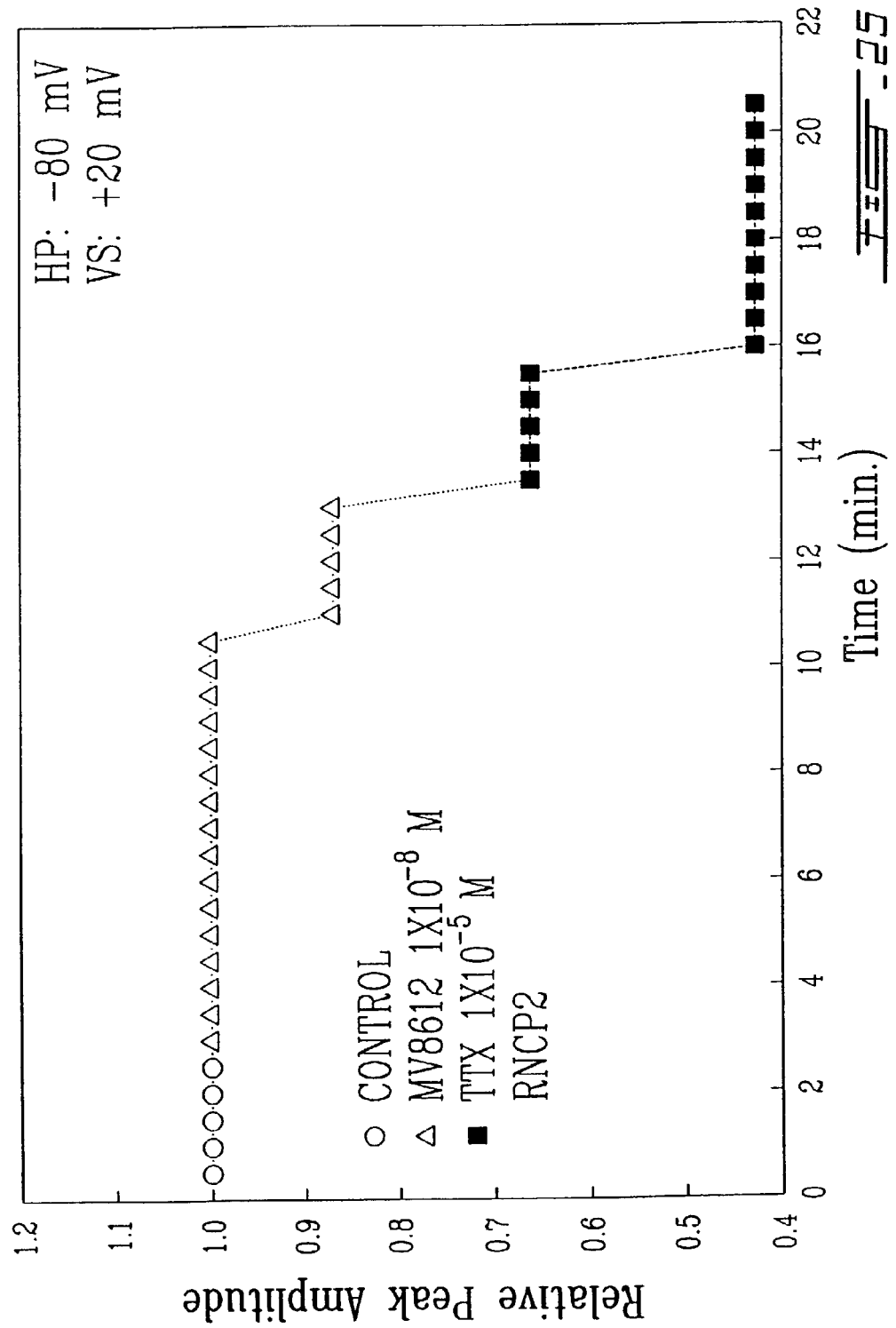
FIG. 25 shows the time course decreases of the TTX-sensitive fast $Na^+$ current in chick heart cells by ($10^{-8}$M) of MV8612.

In another series of experiments using the double-perfused bed of the rat (Claing A. et al., 1994, supra), MV8608 was found to induce a concentration-dependent inhibition of the PAF-induced responses (FIG. 24). The inhibitory properties of MV8608 are specific for PAF as the response to ACh (arterial) and AngII (venous) are unaffected by the pregnane-containing moiety.

In summary, the potency of blockade of the R-type $Ca^{2+}$ channel by MV8608 depends on the degree of the sustained $Ca^{2+}$ overload at the cytosolic and nuclear $Ca^{2+}$, thus it depends on the degree of overstimulation of the R-type $Ca^{2+}$ channel. Consequently, a blockade of the R-type $Ca^{2+}$ channel by MV8608 will be beneficial in pathological situation where sustained cytosolic and nuclear $Ca^{2+}$ take place (such as those described above).

EXAMPLE 12

Effect of MV8612 on TTX-Sensitive Fast $Na^{2+}$ Current

In a series of experiments (n=5), we tested the effect of another MV compound MV8612 on the TTX-sensitive fast $Na^+$ current ($I_{Na}$) of embryonic chick heart cells using the whole-cell voltage clamp technique described above. Superfusion with $10^{-9}$M of MV8612 had no effect on the fast $Na^+$ current. However, increasing the concentration up to $10^{-8}$M decreased the $I_{Na}$ amplitude by 15% and no further decrease was found at $10^{-7}$M. FIG. 26 shows a typical example of the time course effect of $10^{-8}$M MV8612 on the peak amplitude of the fast $I_{Na}$.

These results show that unlike MV8608, MV8612 depresses the fast Na+ current in heart cells. This compound could be used in situations where depressing of the fast Na+ channels is beneficial. Non-limiting examples of such situations include arrythmia, local anaesthetic, and pain. The compound can also br used in combination with drugs acting on fast sodium channel such as lidocaine.

EXAMPLE 13

Effect of MV8612 on L-Type $Ca^{2+}$ Current

In another series of experiments (n=4), we tested the effect of MV8612 on the L-type $Ca^{2+}$ current ($I_{Ca}$) in chick embryonic heart cells using the whole-cell voltage clamp technique referred to above. Superfusion with $10^{-9}$M of MV8612 decreased $I_{Ca}$ amplitude by 10% and increasing the concentration of the compound up to $10^{-8}$M further decreased the current amplitude by 25%. Higher concentration of MV8612 ($10^{-7}$M) decreased the $I_{Ca}$ amplitude by 62%. These results showed that MV8612 possesses a more potent L-type $Ca^{2+}$ channel antagonist properties than that of MV8608.

The relatively high depressing effect of the L-type $Ca^{2+}$ channel by MV8612 would be beneficial where L-type $Ca^{2+}$ blockade are usually used such as, for example, ventricular tachycardia and hypertension.

EXAMPLE 14

Effect of MV8612 on R-Type $Ca^{2+}$ Channel

In another series of experiments (n=7), the effect of $10^{-7}$M of MV8612 was tested on the R-type $Ca^{2+}$ in human aortic VSM cells, using the single channel cell attached recording technique and intra and extra patch pipette application of drugs. As for MV8608, the R-type $Ca^{2+}$ channel was recorded in the presence of $10^{-6}$M of the L-type $Ca^{2+}$ channel blocker nifedipine (in the patch pipette) and using extra-patch pipette solution (containing 140 mM KCl) that mimics the intracellular ionic concentration (to zero the extra-pipette cell membrane potential).

Figure 27A:
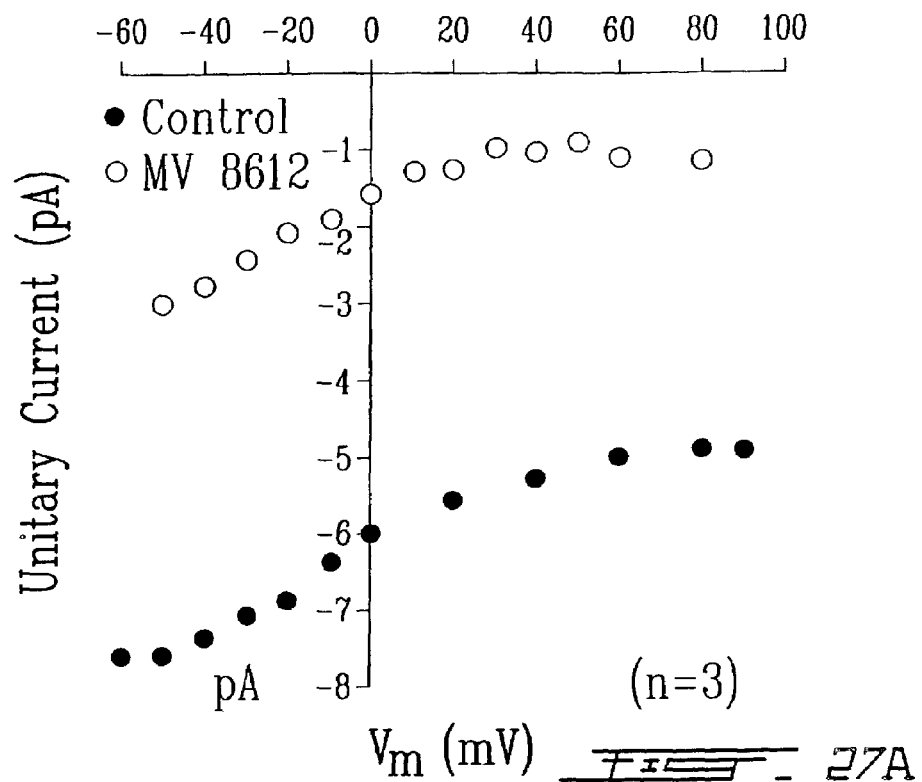
FIG. 27 shows graphs and cell attached single R-type $Ca^{2+}$ channel recording (in presence of ($10^{-6}$M) nifedipine) showing the decrease of the single channel current amplitude (panel A, current voltage relationship, n=3), probability of opening (panel B, open probability-voltage relationship, n=3) by $10^{-7}$M MV8612 application in the patch pipette and panel C, example of single channel current traces. Panels D–E show that application of MV8612 ($10^{-9}$M) to extrapipette solution only induced a slight decrease of the R-type $Ca^{2+}$ channel amplitude and largely increased the probability of opening of the channel. This demonstrates that MV8612 does penetrate to the cytosol and its effect at the cytosolic side of the channel is different from that at the outer side.
Figure 27B:
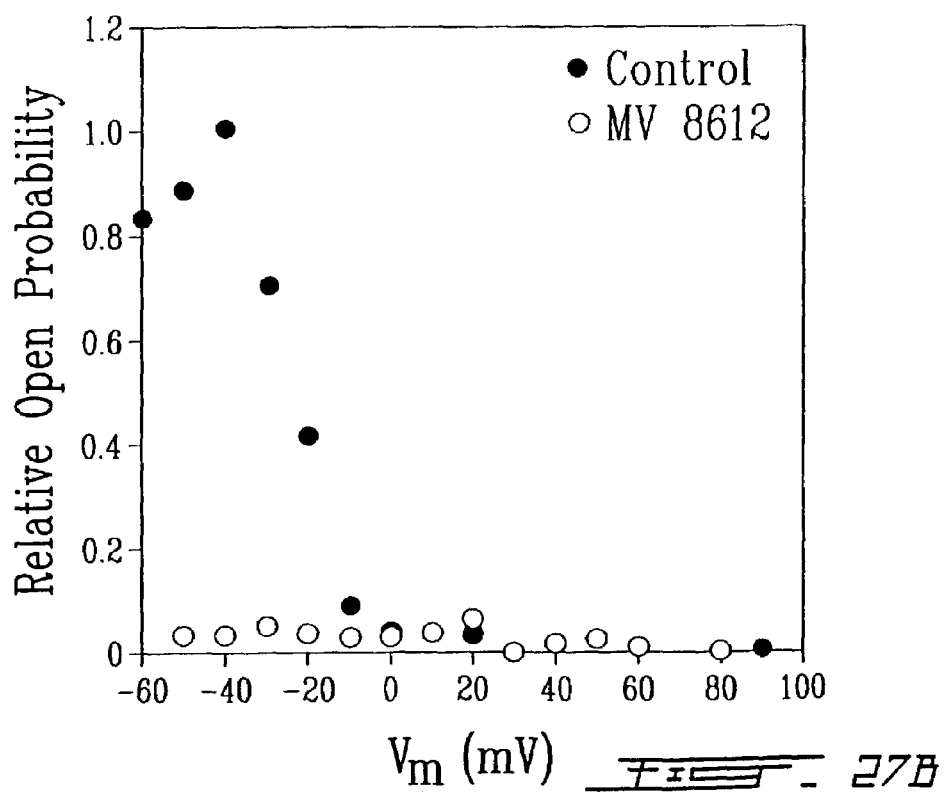

In one series of experiments (n=3), MV8612 (total concentration, $10^{-7}$M) was only applied to the patch pipette. As shown in FIGS. 27A–C, application of $10^{-7}$M MV8612, via the patch pipette, significantly decreased the R-type single $Ca^{2+}$ channel current amplitude (by about 75% of the control value panel A) and the probability and the opening time of the R-type $Ca^{2+}$ channel (Panel B and C). As for MV8608, in one series of experiments (n=4), MV8612 ($10^{-7}$M) was only applied to the extra-patch pipette, in order to verify if the compound penetrates into the cytosol and if so, how it affects the R-type $Ca^{2+}$ channel activity. As shown in FIGS. 27D and E, extra-patch pipette application of MV8612 rapidly increased the R-type $Ca^{2+}$ opening frequence and was accompanied by a small decrease in the single channel current at all sustained membrane potential (HP) levels used (FIG. 27 shows example at HP of −30 where control channel opening is high and a +10 mV where control channel opening is low).

These results demonstrate that as for MV8608, intra-patch pipette application of MV8612, equivalent to extracellular application in normal working single cells or muscle, decreased both R-type $Ca^{2+}$ channel amplitude as well as the probability and duration of opening thereof. However, the extend of blocking of the R-type $Ca^{2+}$ channel amplitude and probability of opening by MV8612 was superior to that of MV8608. Also, these results demonstrate that as MV8608, MV8612 did penetrate the cytosol and did increase the frequency of opening (but not the opening-time) of the channel. However, unlike MV8608, intracellular MV8612 permanently depressed the amplitude of the R-type $Ca^{2+}$ channel. The increase of frequency of opening of the R-type channel by intracellular MV8612 would allow extracellular MV8612 to block the channel activity at the opening state. The large decrease of the R-type $Ca^{2+}$ channel amplitude and activities by intra-patch pipette application of MV8612 when compared to the effect with MV8608 could be due to the permanent decrease of the R-type $Ca^{2+}$ channel by intracellular MV8612 but not by MV8608.

In summary, MV8612 seems to be a more effective blocker of the R-type $Ca^{2+}$ channel than that of MV8608 and this difference is mainly due to the permanent depressing effect of the R-type $Ca^{2+}$ channel by intracellular MV8612. Experiments using $[Ca]_i$, $[Ca]_c$ and $[Ca]_n$ as well as in vivo work (see below) confirm these results and show a more potent effect of MV8612 on the R-type $Ca^{2+}$ channel when compared to that of MV8608.

Thus, the high potency blockade of the R-type $Ca^{2+}$ channel by MV8612 will be more effective than MV8608 in reducing $Ca^{2+}$ overload that occurred during many abnormal cell function such as those described for MV8608 in example 10. Also, since MV8612 (but not MV8608) depressed the fast Na+ channel and the L-type $Ca^{2+}$ channel, this compound will be highly effective not only in acute but also in chronic diseases such as those described in examples 10 to 13.

EXAMPLE 15

Effect of MV8612 on $[Ca]_i$, $[Ca]_c$, $[Ca]_n$ in the Presence of Extracellular L-Type $Ca^{2+}$ Blocker In another series of experiments, as for MV8608, the effect of MV8612 was tested on $[Ca]_i$, $[Ca]_c$, $[Ca]_n$ (in the presence of extracellular L-type $Ca^{2+}$ blocker, nifedipine, $10^{-6}$M) of embryonic chick heart (FIGS. 29 to 31 and 34) and human aortic VSM cells (FIGS. 29 to 33) as well as in vivo anaesthetized guinea pig (FIG. 36).

Figure 31A:
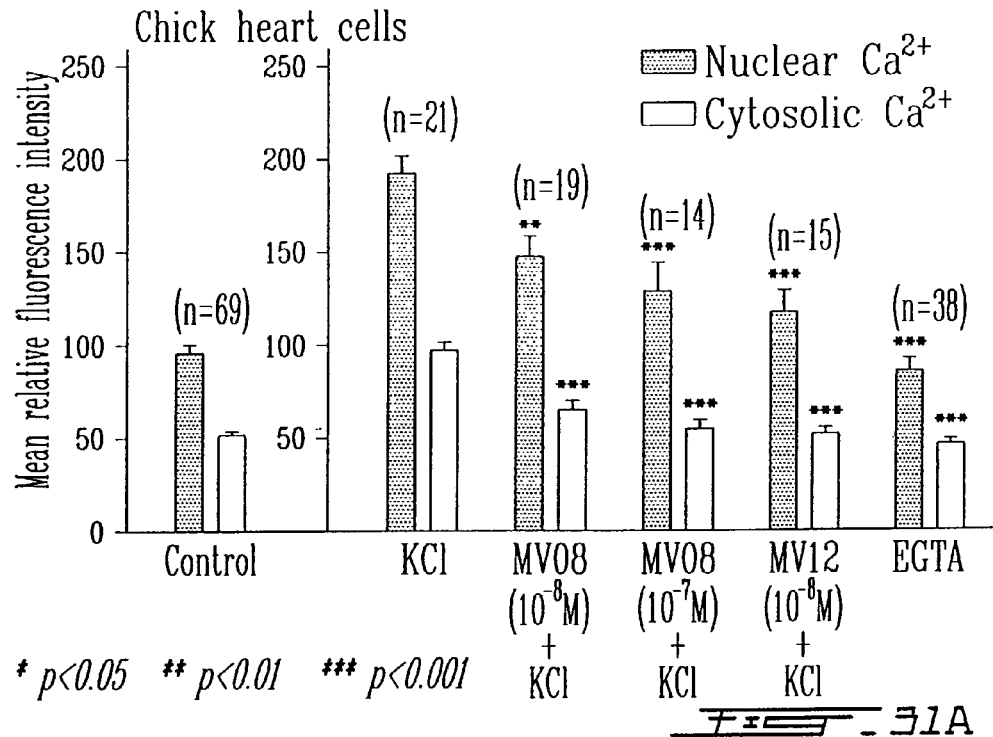
FIG. 31 represents histograms showing the preventive effect by MV8608 and MV8612 of sustained depolarization and high PAF ($10^{-7}$M) induced sustained increase of $[Ca]_c$ and $[Ca]_n$ via stimulation of the R-type $Ca^{2+}$ channel in chick heart cells and human aortic vascular smooth muscle cell line.
Figure 31B:
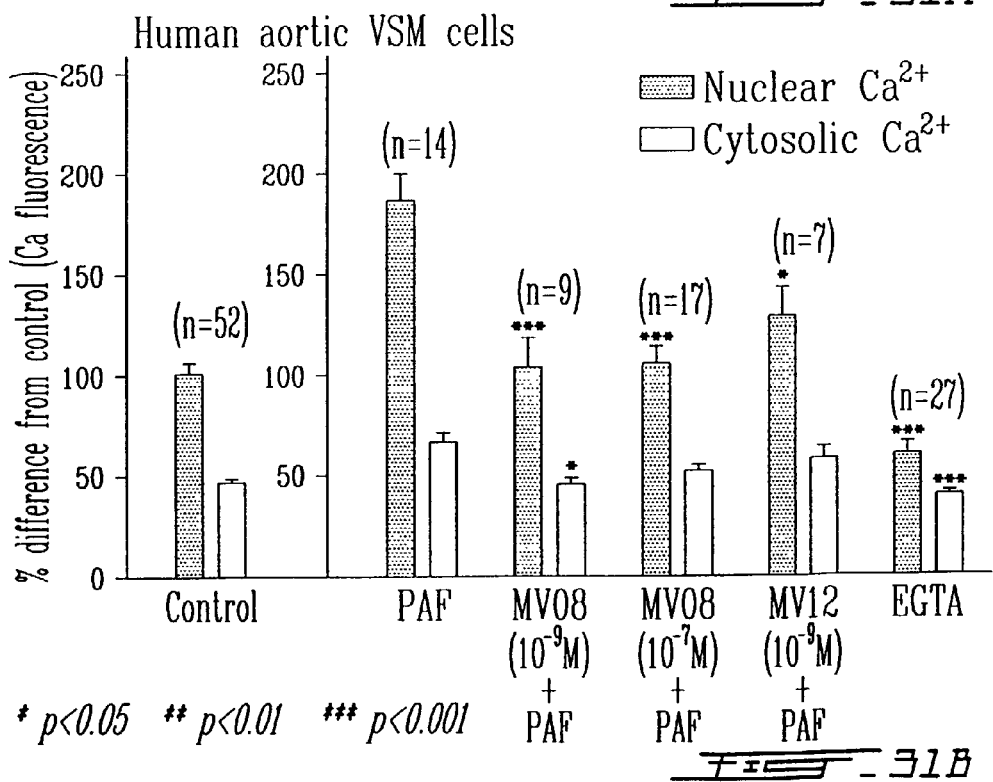
Figure 32:
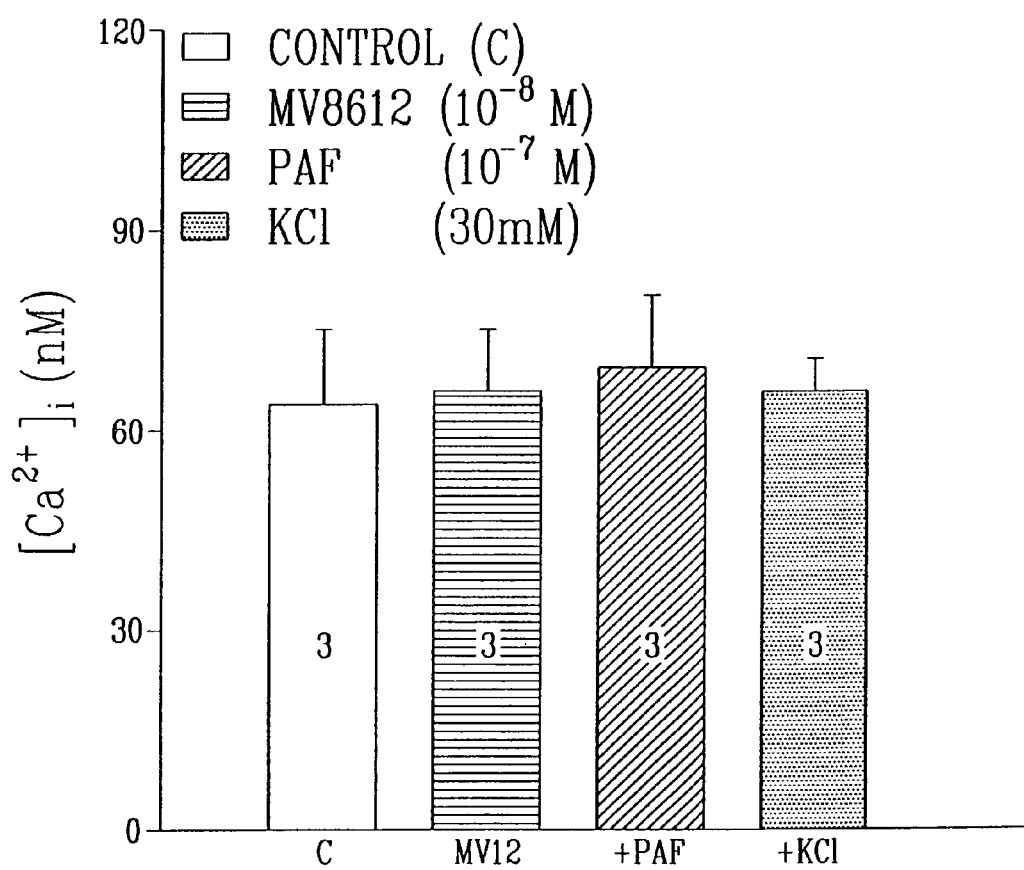
FIG. 32 represents histograms showing the preventive effect by MV8612 ($10^{-8}$M) of sustained depolarization (KCl 30 mM) and high PAF ($10^{-7}$M) induced sustained increase of $[Ca]_i$ via activation of the R-type $Ca^{2+}$ channel in human aortic vascular smooth muscle cell line.
Figure 33:
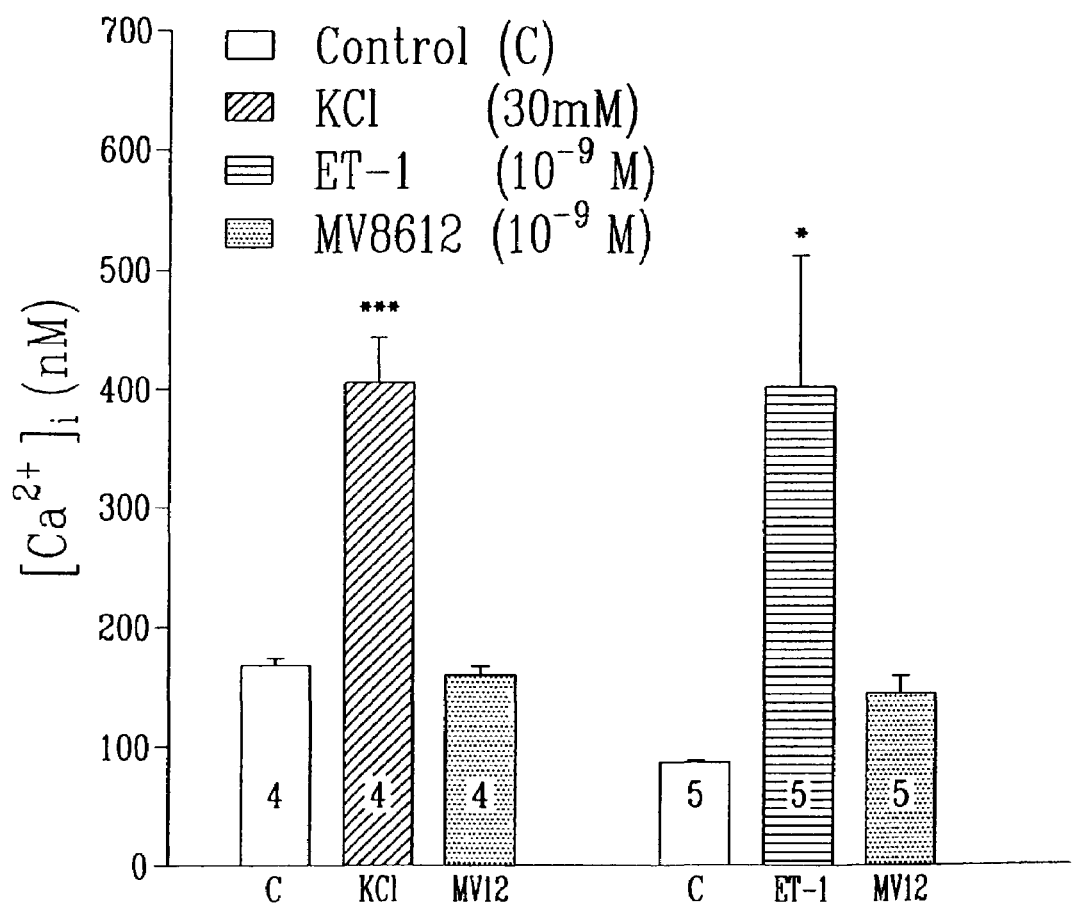
FIG. 33 represents histograms showing the blockade by MV8612 ($10^{-9}$M) of sustained depolarization and ET-1 ($10^{-9}$M) induced sustained increase of $[Ca]_i$ via activation of the R-type $Ca^{2+}$ channels in rabbit aortic vascular smooth muscle.
Figure 34:
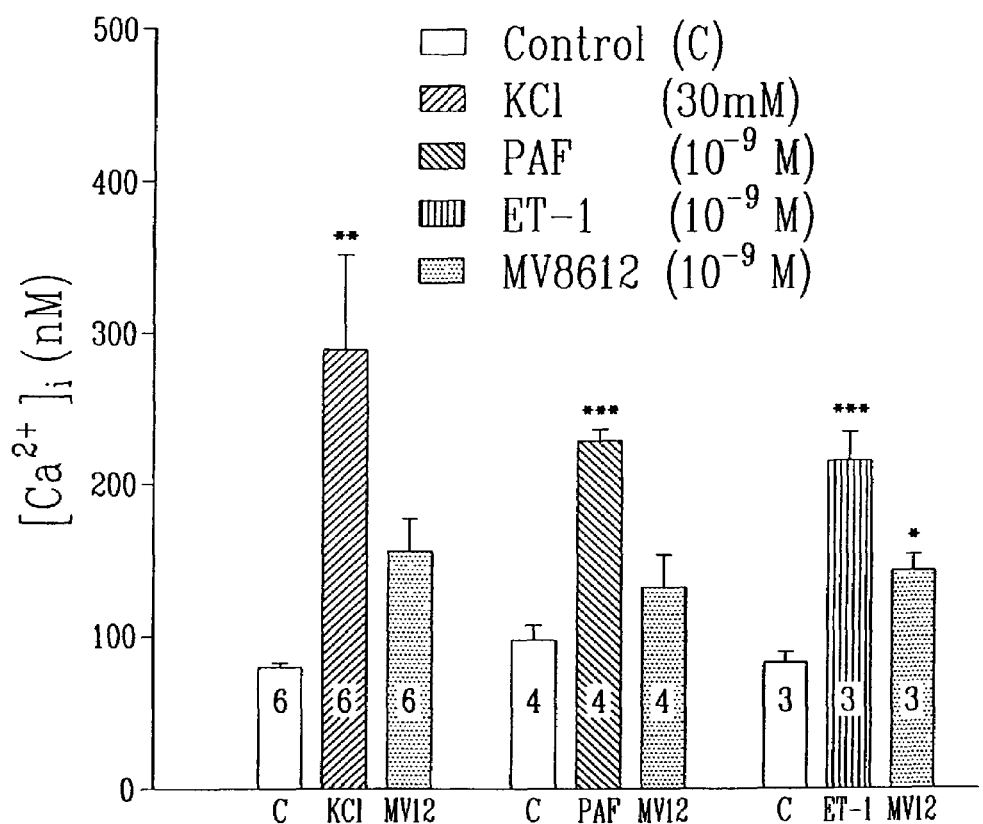
FIG. 34 represents histograms showing the blockade by $10^{-9}$M MV8612 of the sustained depolarization, low PAF ($10^{-9}$M) and ET-1 ($10^{-9}$M) induced sustained increase of $[Ca]_i$ via the activation of the R-type $Ca^{2+}$ channels in chick heart cells.

Using Fura-2 $[Ca]_i$ measurement technique, in one series of experiments we tested the effect of MV8612 ($10^{-9}$M) on the stimulation of R-type $Ca^{2+}$-induced sustained increase of $[Ca]_i$ by sustained depolarization (FIGS. 26 and 27), PAF ($10^{-9}$M, FIG. 34) and ET-1 (FIGS. 33 and 34). These experiments showed that $10^{-9}$M of MV8612 significantly decreased sustained increase of $[Ca]_i$ induced by sustained depolarization and hormones. Also, MV8612 ($10^{-8}$M) was found to prevent stimulation of the R-type $Ca^{2+}$ channel induced sustained increase of $[Ca]_i$ by sustained depolarization and chronic concentration of PAF ($10^{-7}$M) (FIG. 32). Using 3-dimension Fluo-3 Ca 2+ measurement of $[Ca]_c$ and $[Ca]_n$, MV8612 was found to be a more potent blocker than MV8608 in the overstimulation of R-type $Ca^{2+}$ channel induced sustained increase of $[Ca]_c$ and $[Ca]_n$ by sustained depolarization and high concentration of PAF ($10^{-7}$M) (FIGS. 29 and 30). MV8612 was also found to be equipotent in preventing the stimulation of the R-type $Ca^{2+}$ channel by sustained depolarization and high concentration of PAF ($10^{-7}$M) (FIG. 31).

On the other hand, in vivo administered PAF, induced a marked hypotension in the anaesthetized rat and guinea pig.

In addition, the pro-inflammatory mediator also induced an important bronchoconstriction in the guinea pig, where PAF induced its hypotensive effects through the release of EDRF, its bronchoconstrictive properties are solely mediated by the release of thromboxane $A_2$.

Figure 35A:
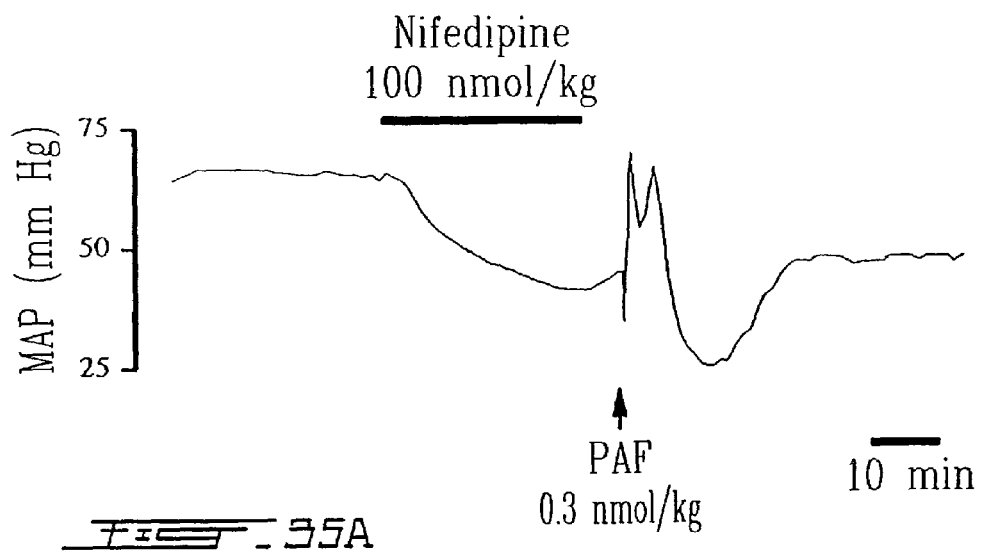
FIG. 35 shows the marked intrinsic hypotensive properties of the dual L- and R-type $Ca^{2+}$ channel blocker isradipine (panel B) when compared to the pure L-type $Ca^{2+}$ channel blocker, nifedipine (Panel A)
Figure 35B:
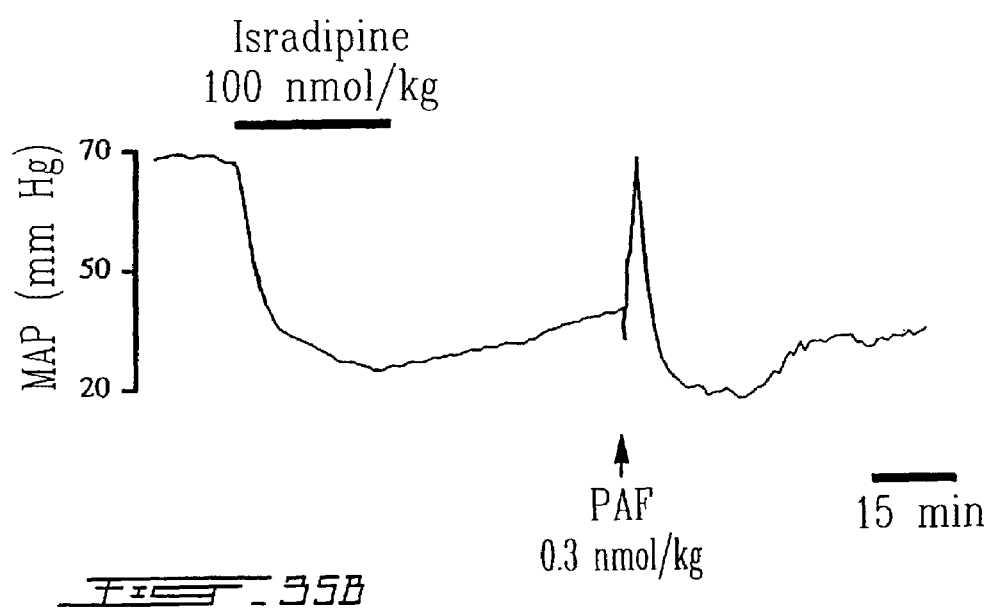

Characteristically, standard $Ca^{2+}$ blockers such as nifedipine and the dual L and R-type blocker isradipine have marked intrinsic hypotensive properties in the rat (results not shown) and in the guinea pig (FIG. 35).

Interestingly, the R-type blocker, MV8612, is devoid of marked intrinsic effect in the guinea pig. As shown in FIG. 36, pretreatment of the guinea pig with MV8612 abolished the bronchoconstrictive responses and very significantly reduced the hypotensive effects of PAF. Following withdrawal of the treatment with MV8612, the hypotensive effect of PAF is fully restored in the same animal (for methodology, please refer to Gratton et al., 1995a, Am. J. Hyper. 8:1121–1127). Identical inhibition of MV8612 has been observed on the hypotensive effect of PAF in the anaesthetized rat (for methodology, please refer to D'Orléans-Juste et al., 1996, Can. J. Physiol. Pharmacol. 74:811–817; Gratton et al., 1995a, supra; 1995b, Br. J. Pharmacol. 114:720–726).

These results again confirm the more potent effect of MV8612 (when compared to MV8608) on blocking the R-type $Ca^{2+}$ channel and related cytosolic and nuclear $Ca^{2+}$ overload. The high potency effect of MV8612 of the R-type $Ca^{2+}$ combined to its depressing effect of the fast $Na^+$ and the L-type $Ca^{2+}$ channels give this compound a higher spectrum of action than that of MV8608 and isradipine. The MV8612 as well as MV8608 are unique compounds that block both the cytosolic and nuclear $Ca^{2+}$ overload. This later effect of MV8608 and especially MV8612 gives these compounds a new target other than that of the cytosolic membrane channels but also a nuclear and a perinuclear ionic channel target blockers. The MV8612 will be beneficial in cell disorders that implicate abnormal $Ca^{2+}$ and $Na^+$ transport and preventing cytosolic $Ca^{2+}$ overload such as in diseases cited in examples 7 to 14.

In conclusion, the pharmacological results presented herein support the unique R-type $Ca^{2+}$ channel blocking properties of the MV8608 and MV8612 and their derivatives.

EXAMPLE 16

"In Vivo" Results with Compounds MV8608 and MV8612

In this experiment (N=5 to 6 animals per group), the anti-oedemagenic action of compounds MV 8608 and MV 8612 against bradykinin and several mediators which are reported to be involved in the inflammatory processes, was evaluated. The procedures used to perform these experiments have been reported elsewhere (Neves et al., 1993, Eur. J. Pharmacol. 243:213–219; Campos et al., 1995, Br. J. Pharmacol. 114:1005–1013; Campos et al., 1996, Br. J. Pharmacol. 117:793–798; Eur. J. Pharmacol. 316:227–286). As can be seen in FIG. 37A, MV 8608 (10 and 100 nmol/paw), when co-injected with des-$Arg^9$-bradykinin, caused a dose-related inhibition of paw oedema induced by this peptide. In contrast, at similar doses, MV 8608 had no significant effect against bradykinin-induced hindpaw oedema in animals treated with LPS (Campos et al., 1996, supra) (FIG. 37B). As reported previously, in rats treated 30 days prior to a systemic injection of LPS, both $B_1$ and $B_2$ kinin selective agonists caused marked oedema formation (FIGS. 37C and D (Campos et al., 1996, supra)). Under such experimental conditions, compound MV 8608 (100 nmol/paw) significantly inhibited both des-$Arg^9$-BK and bradykinin-induced rat paw oedema (FIGS. 37C and D). However, MV8608 was more effective against $B_1$ agonist-mediated oedema formation. In addition, at 100 nmol/paw, compound MV 8608 consistently inhibited the paw oedema induced by PAF (FIG. 38B), and partially inhibited the oedema induced by prostaglandin $E_2$ ($PGE_2$) (FIG. 38A), leaving oedema induced by substance P unaffected (FIG. 38C). Interestingly, MV 8608 (10 and 100 nmol/paw) also inhibited significantly oedema formation induced by subplantar injection of ovalbumin in animals that had been actively sensitised to this antigen (FIG. 38D).

Results of FIG. 39 (A and B) demonstrate that MV 8608 (10 and 100 nmol/paw) in a dose-dependant fashion prevented the potentiation of paw oedema caused by association of low dose of des-$Arg^9$-BK plus PAF (FIG. 39A) or with $PGE_2$ (FIG. 39B). MV 8608 (10 and 100 nmol/paw) when co-injected in association with carrageenan (FIG. 40A), dextran (FIG. 40B), histamine (FIG. 40C) or with serotonin (FIG. 40D), significantly prevented the oedemagenic response caused by these substances. However, MV 8608 was much more effective in inhibiting paw oedema induced by carrageenan, an effect which has been reported to be dependent on the release of several mediators, including kinins, histamine, serotonin and PAF (Hargreaves et al., 1988, Clin. Pharmacol. Ther., 44:613–621; Burch et al., 1990, Naunyn-Schimiedeberg's Arch. Pharmacol., 342:189–193; Damas et al., 1992, Eur. J. Pharmacol., 211: 81–86; Damas et al., 1996, Naunyn-Schmiedeberg's Arch. Pharmacol., 354:670–676; De Campos et al., 1996, Eur. J. Pharmacol. 316:227–286).

Figures 44A, 44B:
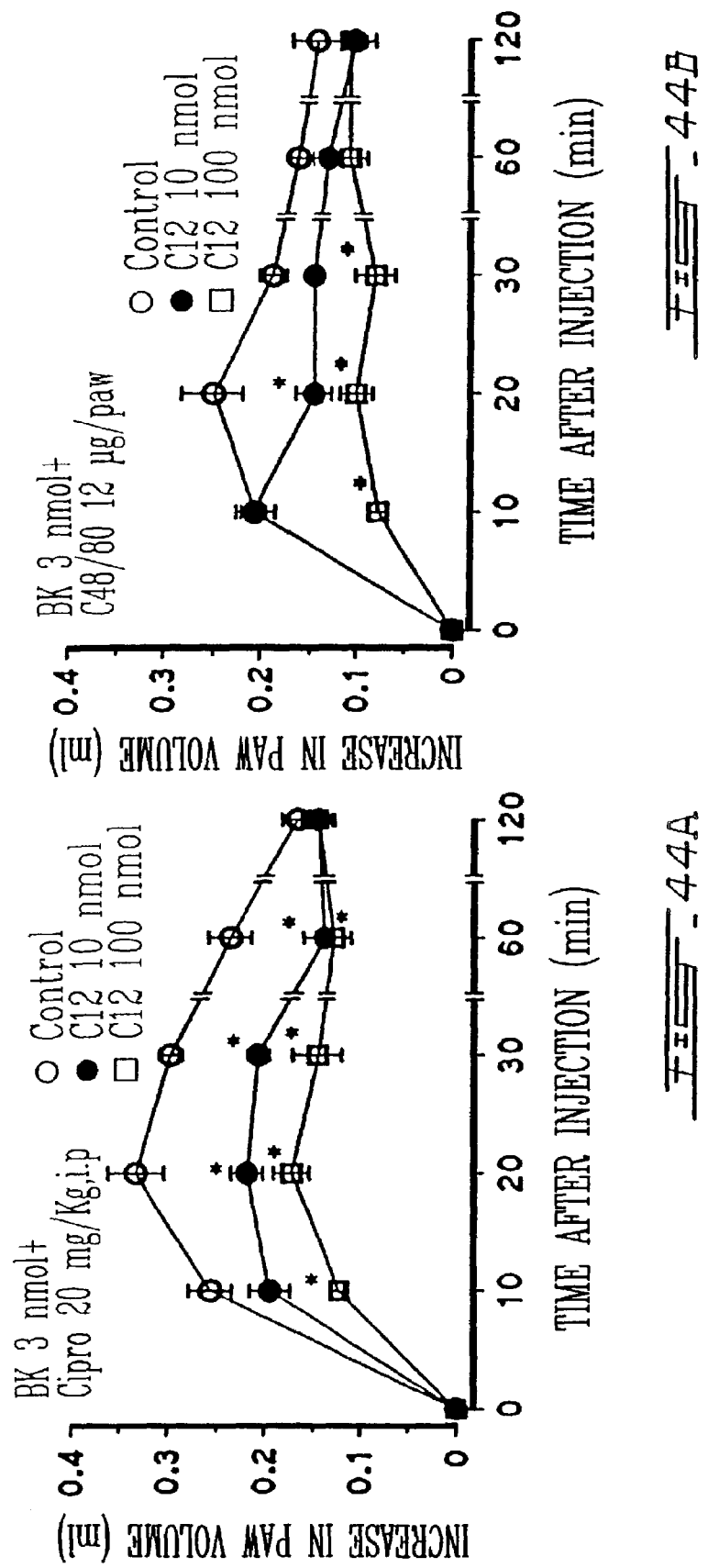
FIG. 44 shows the effect of an intraperitoneal injection of MV 8612 isolated from *Mandevilla velutina* on rat paw oedema caused by subplantar injection of bradykinin in animals treated with cyproheptadine (A) or compound 48/80

In marked contrast, and confirming previous "in vitro" and "in vivo" results (Calixto et al., 1986, Br. J. Pharmacol. 88:937–941; Calixto et al., 1985, Br. J. Pharmacol., 85:729–731; 1987, supra; 1988, supra; 1991a, Prostaglandins, 41:515–526; 1991b, In: Bradykinin Antagonists: Basic and Clinical Research. Ed. by Ronald M. Burch, Marcel Dekker Inc, New York, pp. 97–129), MV 8612 (10 and 100 nmol/paw) significantly inhibited bradykinin and the selective $B_2$ agonist $tyr^8$-bradykinin-induced paw oedema (FIGS. 41A and D), while having no significant effect against oedema-induced by des-$Arg^9$-BK in animals treated with LPS (FIG. 41B) (Campos et al., 1996, supra). The anti-oedematogenic effect caused by MV 8612 seems to be systemic, because the controlateral paw treated with saline also revealed an significant anti-oedemagenic action (FIG. 41C). On the other hand, MV 8612 (10 and 100 nmol/paw) dose-dependently inhibited $PGE_2$ and carrageenan-induced oedema formation (FIG. 42A, C), but caused only a minimal inhibition of PAF and substance P-mediated paw oedemas (FIGS. 42B and D). Compound MV 8612 (10 nmol/paw) significantly inhibited the oedema formation caused by association of low dose of bradykinin plus the calcitonin gene related peptide (FIG. 43A), $PGE_2$ (FIG. 43B) and prostacyclin (FIG. 43D), but did not interfere with oedema-induced by the association of bradykinin plus PAF (FIG. 43C). The anti-oedematogenic action of MV 8612 against bradykinin-induced oedema was independent on the release of histamine, since a dose-related inhibition was still observed in animals treated with cyprohetadine or with compound 48/80 (FIGS. 44A and B). The inhibition of MV 8612 against oedema caused by bradykinin installs rapidly (30 min) and lasted for at least 2 h (FIG. 45).

When tested in mice, MV 8612 (40 to 160 nmol/paw) inhibited bradykinin and carrageenan-induced paw oedema in mice in a dose-dependent manner (FIGS. 46A and B). At the same dose, MV 8612 failed to affect significantly PAF-acether or serotonin-induced oedema formation (FIGS. 46C and D). Confirming the effect observed with crude extract of *Mandevilla velutina*, when MV 8612 was injected systemically, MV 8612 (7.5 and 15 mol/kg, i.p.), given 30 min prior, produced a dose-dependent inhibition of bradykinin and cellulose sulphate-induced paw oedema (FIGS. 47A and 8). However, at the same range of dose, MV 8612 had no significant effect against paw oedema induced by serotonin and histamine (FIGS. 47C and D). In marked contrast, compound MV 8608 (7.5 and 15 mol/kg, i.p) caused a dose-related inhibition of histamine and serotonin-induced oedema formation, leaving paw oedema to bradykinin unaffected (FIG. 48A, B and C).

Taken together, these results indicate that both MV 8612 and MV 8608 compounds show potent topical and systemic anti-inflammatory properties through a distinct mechanism of action, albeit through an overstimulation of R-type $Ca^{2+}$ channels. While MV 8612 was more active against inflammatory response caused by bradykinin via stimulation of $B_2$ receptors, MV 8608 was effective in preventing oedemas elicited by histamine, PAF-acether and by the $B_1$ selective agonist des-$Arg^9$-BK.

EXAMPLE 17

Anti-Inflammatory Action of MV8612 and MV8608

Figure 52A:
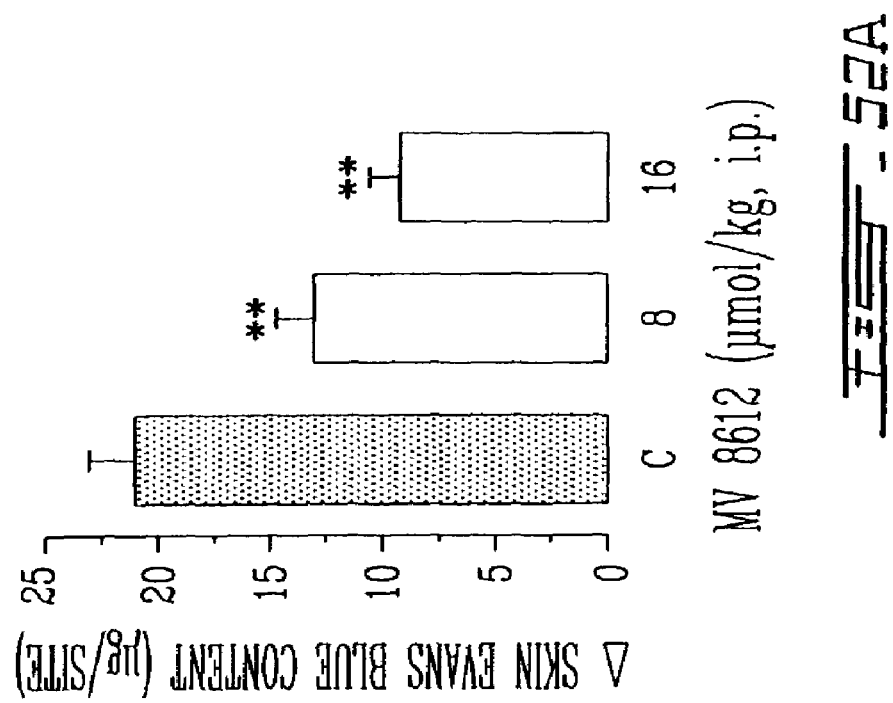

To assess further the anti-inflammatory action of MV 8612 and MV 8608, their effects against the inflammatory responses caused by several mediators of inflammation in a murine model of pleurisy were tested (Saleh et al., 1996, Br. J. Pharmacol. 118:811–819). In addition, both compounds were tested against the increase of vascular permeability caused by bradykinin in the rat skin (Neves et al., 1993b, Phytotherapy Research. 7:356–362). FIG. 49 shows that compound MV 8612 (30 and 60 mol/kg, i.p.) given 1 h prior, significantly inhibited plasma extravasation (A) as well as the total (B) and neutrophils cells (C) in response to intrapleural injection of carrageenan. Compound MV 8608 (30 mol/kg, i.p) also inhibited significantly the total and neutrophil cells migration caused by intrapleural injection of carrageenan (FIG. 50). Confirming the previous results, compound MV 8608 (30 mol/kg, i.p.) also antagonised significantly the plasma extravasation and the mononuclear cells influx caused by intrapleural injection of PAF (FIG. 51). In contrast, at the same range of dose, MV 8612 did not affect significantly the inflammatory response caused by PAF acether in a murine model of pleurisy (FIG. 51). However, both MV 8612 (8 and 16 mol/kg, i.p) and MV 8608 (27 and 54 mol/kg, i.p.) antagonised in a dose-related manner, the increase of vascular permeability caused by bradykinin in the rat skin (FIGS. 52A and B). Compound MV 8612 was more active than MV 8608.

This data extend our previous results (Calixto et al., 1991 a, supra; Zanini et al., 1992, Phytotherapy Research, 6:1–5; Neves et al., 1993b, supra) supportting the view that both MV 8612 and MV 8608 exhibit powerful anti-inflammatory properties.

EXAMPLE 18

Effect of MV8612 and MV8608 on Human Lymphocyte Proliferation In Vivo

In a separate series of experiments, compounds MV 8612 and MV 8608 were tested to analyze whether they interfered with human lymphocyte proliferation "in vitro". These experiments were carried out as reported previously (Moraes et al., 1996, Eur. J. Pharmacol. 312:333–339). The results of FIG. 53(A and B) show that compound MV 8612 (0.02 to 0.32 M) and, to a lesser extent, MV 8608 (14.5 to 116 M) caused graded inhibition of human lymphocyte proliferation, with MV 8612 being about 570 fold more potent. These results may be explained by their above-demonstrated anti-inflammatory properties.

EXAMPLE 19

Antinociceptive Actions of MV8612 and MV8608

Figures 57A, 57B:
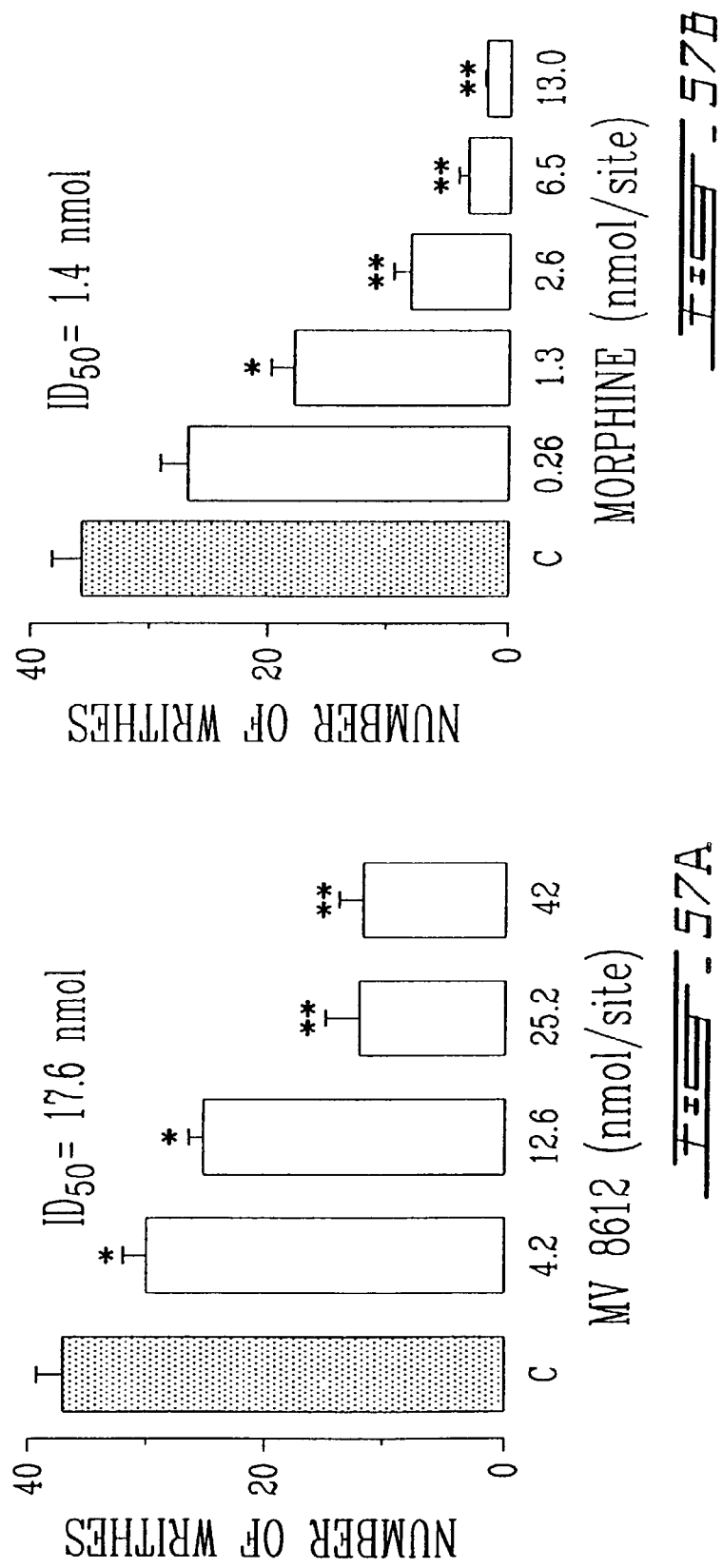

The antinociceptive actions of compound MV 8612 and MV 8608 were investigated in different models of nociception in mice as reported previously (Vaz et al., 1996, J. Pharmacol. Exp. Ther. 278:304–312). Compound MV 8612 (0.25 to 2.5 mol/kg, i.p.), given 30 min prior, caused dose-dependent inhibition of acetic acid (FIG. 54A) acetylcholine (FIG. 55A) and kaolin (FIG. 56A)-*induced* writhing response in mice. However, MV 8612 was about 2-fold more potent against kaolin-induced pain. In contrast, compound MV 8608 (2.7 to 27 mol/kg, i.p.) caused only partial or even no antinociceptive action when tested in the same model of pain. When compared with morphine and indomethacin (Table 6), MV 8612 was about 2-fold more potent when assessed in the kaolin-induced writhes. Given intracerebroventricularly (i.c.v) MV 8612 (4.2 to 42 nmol/site), like morphine (0.26 to 13 nmol/site), caused a dose-related antinociception when assessed against acetic acid-induced writhes (FIGS. 57A and B). MV 8612 was about 12-fold less potent than morphine.

These results indicate that MV 8612, exhibits potent antinociceptive actions, comparable to those of morphine and indomethacin. Its antinociceptive property is elicited by R-type $Ca^{2+}$ channel blocking properties and is associated with its anti-bradykinin action, but appears to be unrelated to activation of opioid, β-adrenergic, serotonin or to the interaction with the nitric oxide pathway (results not shown).

TABLE 6

Antinociceptive potencies of MV 8612, morphine and indomethacin in mice.

| | $ID_{50}$ μmol/kg, i.p | | | |
|---|---|---|---|---|
| DRUG | KAOLIN | ACETYL-CHOLINE | ACETIC ACID | TAIL-FLICK |
| MV 8612 | 0.4 (0.3–0.6) | 2.2 (2.0–2.3) | 2.4 (1.9–2.6) | no effect |
| MORPHINE | 1.4 (1.2–1.7) | 1.4 (1.0–1.8) | 1.3 (1.0–1.6) | 6.0(5.7–6.4) |
| INDO-METHACIN | 1.6 (1.4–1.8) | 0.8 (0.5–1.0) | 1.2 (0.9–1.4) | no effect | each group represents the mean of 6 to 8 animals

Although the present invention has been described hereinabove by way of preferred embodiments thereof, it can be modified, without departing from the spirit and nature of the subject invention as defined in the appended claims.

The present description refers to a number of documents, the content of which is herein incorporated by reference.

We claim:

1. A method for specifically inhibiting overstimulation of a R-type $Ca^{2+}$-channel in a warm blooded animal in need of an inhibition of said overstimulation, comprising an administration of an effective amount of a compound-having the formula:

EST, wherein:
a) E and S define a saponin oligosugar portion, with E defining the terminal sugar portion thereof; and
b) T is a pregnane-3β-ol steroid portion,
together with a pharmaceutically acceptable carrier.

2. A method of treating a disease or condition associated with an overstimulation of R-type Ca²⁺ channels without significantly affecting the basal activity thereof in a patient suffering from said disease or condition, comprising an administration of an effective amount of a compound having the formula:
EST, wherein:
a) E and S define a saponin oligosugar portion or monomeric sugar portion, with E defining the terminal sugar portion thereof; and
b) T is a pregnane-3β-ol steroid portion,
together with a pharmaceutically acceptable carrier.

3. A method of treating a disease or condition associated with a sustained elevation of $[Ca]_c$, $[Ca]_n$, R-type Ca²⁺ blocking, and/or cytosolic and nuclear Ca²⁺ accumulation in a patient suffering from said disease or condition, comprising an administration of a therapeutically effective amount of a compound having the formula:
EST, wherein:
a) E and S define a saponin oligosugar portion, with E defining the terminal sugar portion thereof; and
b) T is a pregnane-3β-ol steroid portion,
together with a pharmaceutically acceptable carrier.

4. A method for decreasing spontaneous cell proliferation comprising administering to said cell in vitro an effective amount of a compound having the formula:
EST, wherein:
a) E and S define a saponin oligosugar portion, with E defining the terminal sugar portion thereof; and
b) T is a pregnane-3β-ol steroid portion,
together with a pharmaceutically acceptable carrier.

5. The method of claim 1, wherein said compound has the formula:

6. The method of claim 2, wherein T is as set forth in

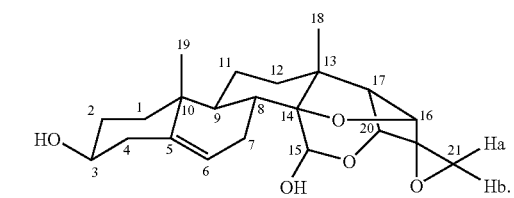

7. The method of claim 2, wherein S is L oleandrose, E is 3-O-methylether 2,4 diacetylfucose, and T is 5-pregnane-3β-ol oxytricyclo 15-ol.

8. The method of claim 2, comprising an administration of at least one compound of said formula EST, together with a pharmaceutically acceptable carrier.

9. A method of treating a disease or condition associated with an overstimulation of R-type Ca²⁺ channels without significantly affecting the basal activity thereof in a patient suffering from said disease or condition, comprising an administration thereto of an effective amount of a compound having the formula:

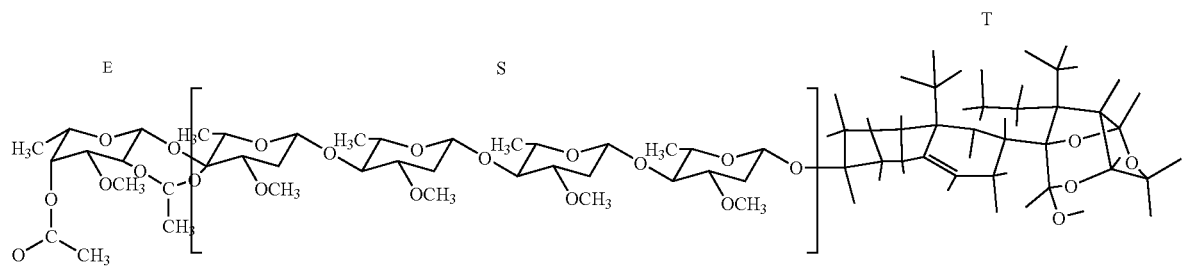

or a pharmaceutically acceptable salt thereof.

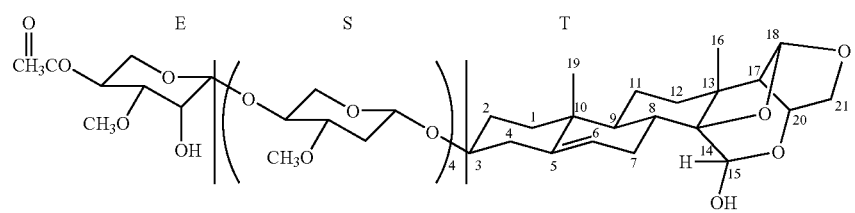

or a pharmaceutically acceptable salt thereof, together with a pharmaceutically acceptable carrier.

10. A method of treating a disease or condition associated with a sustained elevation of $[Ca]_c$, $[Ca]_n$, R-type $Ca^{2+}$ blocking, and/or cytosolic and nuclear $Ca^{2+}$ accumulation in a patient suffering from said disease or condition, comprising an administration thereto of a therapeutically effective amount of a compound having the formula:

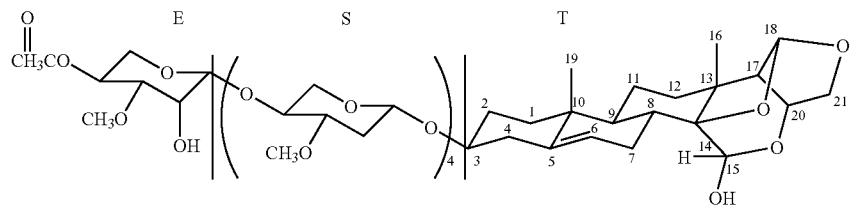

or a pharmaceutically acceptable salt thereof, together with a pharmaceutically acceptable carrier.

11. A method for decreasing spontaneous cell proliferation comprising administering to said cell in vitro an effective amount of a compound having the formula:

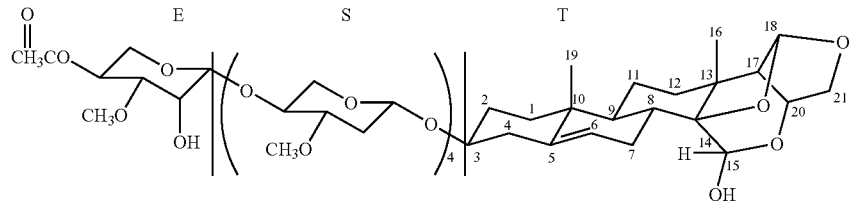

or a pharmaceutically acceptable salt thereof, together with a pharmaceutically acceptable carrier.

12. The method of claim 2, wherein said compound has the formula:

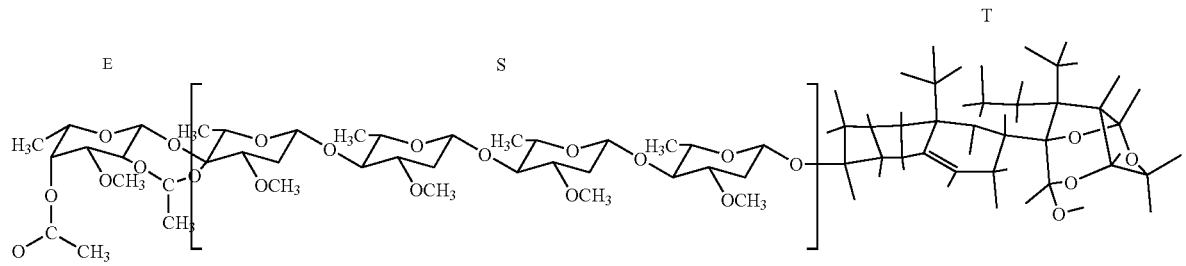

or a pharmaceutically acceptable salt thereof.

13. The method of claim 3, wherein said compound has the formula:

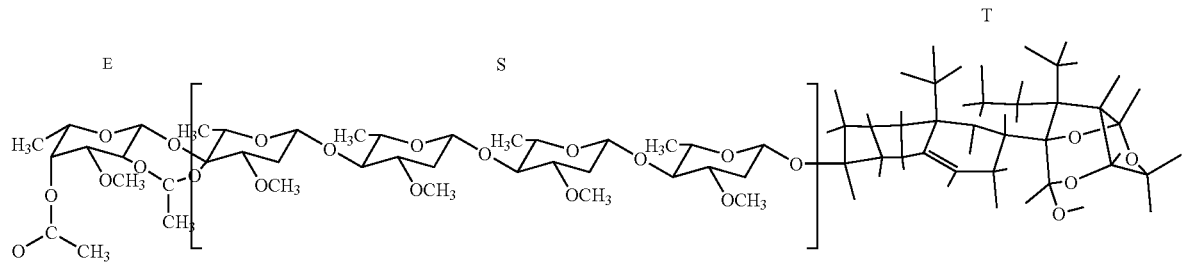

or a pharmaceutically acceptable salt thereof.

14. The method of claim 4, wherein said compound has the formula:

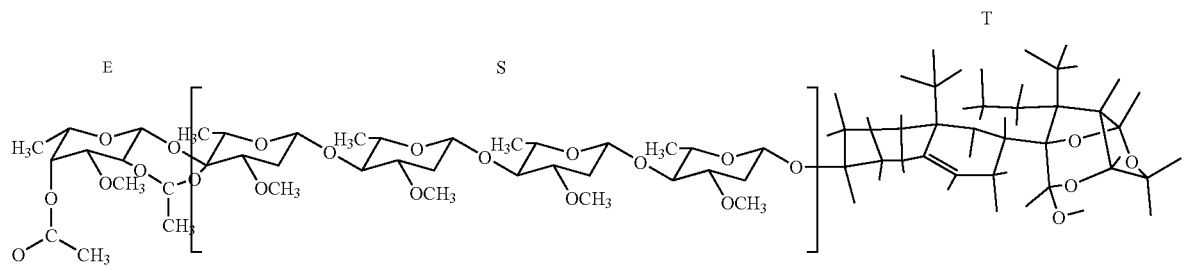

or a pharmaceutically acceptable salt thereof.

15. A method of treating a disease or condition associated with an overstimulation of R-type $Ca^{2+}$ channels without significantly affecting the basal activity thereof in a patient suffering from said disease or condition, comprising an administration thereto of an effective amount of a compound selected from the group consisting of:

a)
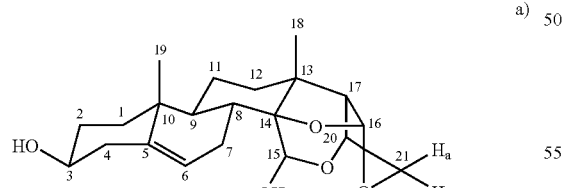

b)
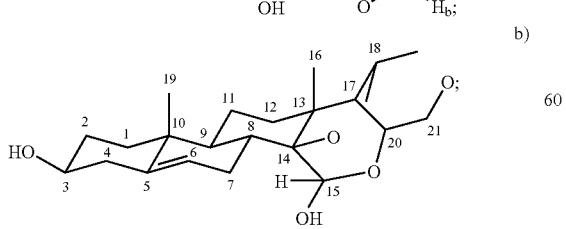

-continued c)
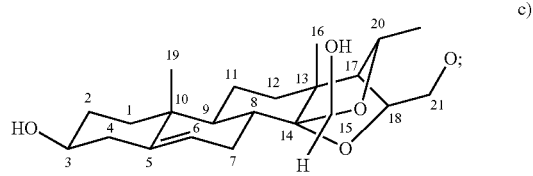

d)
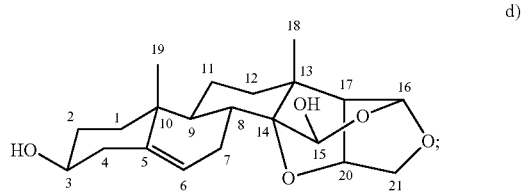

e)
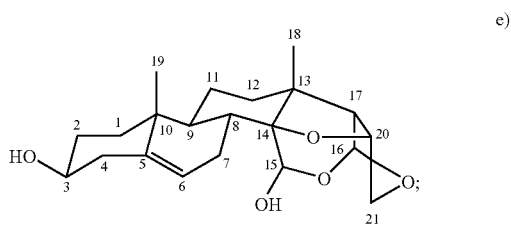

-continued f)
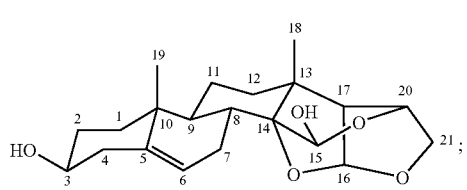

g)
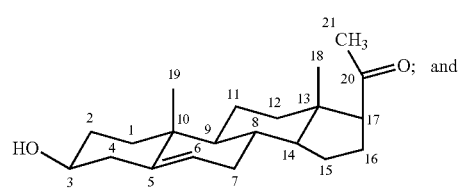

h)
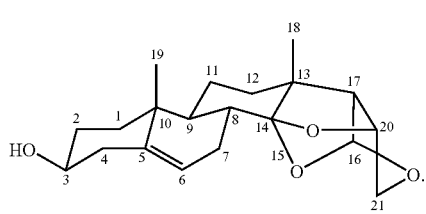

together with a pharmaceutically acceptable carrier.

16. The method of claim 4, wherein said cell is a cancer or tumor cell.

17. The method of claim 11, wherein said cell is a cancer or tumor cell.

18. The method of claim 2, wherein S is a tetra sugar.

19. The method of claim 2, wherein S is selected from the group consisting of α(1–4) (2-deoxy, 3-methoxy)-L-lyxotetrose, α(1–4) (2-deoxy, 3-methoxy) L-xylotetrose, α(1–4)(2-deoxy, 3-methoxy)-L-arabinotetrose, α(1–4) (2-deoxy, 3-methoxy)-L-xylotetrose, α(1–4)(2-deoxy, 3-methoxy-L-ribopyranotetrose, α(1–4) (2-deoxy, 3,4 methoxy-L-sorbotetrose, α(1–4)-L-lyxotetrose, (1–4)-L-xylotetrose, α(1–4)-L-arabinotetrose, α(1–4)-L-xylotetrose, α(1–4)-3,4 methoxy-L-lyxotetrose, α(1–4)-3,4 methoxy-L-xylotetrose, α(1–4)-3,4 methoxy-L-arabinotetrose, α(–4)-3,4 methoxy-L-xylotetrose, α(1–4)-3,4 methoxy-L-ribopyranotetrose, α(1–4)-3,4 methoxy-L-sorbopyranotetrose, α(1–4)-L-lyxotetrose, α(1–4)-L-xylotetrose, α(1–4)-L-arabinotetrose, α(1–4)-L-ribopyranotetrose, oleandrose, and α(1–4)-L-sorbotetrose.

20. The method of claim 2, wherein E is selected from the group consisting of 4-acetoxy-3 methoxy-L-α-lyxose, 4-acetoxy-3-methoxy-L-α-xylose, 4-acetoxy-3-methoxy-L-α-arabinose, 4-acetoxy-3-methoxy-L-α-ribopyranose, diacetylfucose, and 4-acetoxy-3-methoxy-L-α-sorbose-acetoxy.

21. The method of claim 2, wherein T is selected from the group consisting of 5-pregnane-3β-ol oxytricyclo-15-ol, illustrol, 5-pregnane-3-ol-20-one, cholesterol, cholic acid, ergosterol, stigmasterol, androstenon, digitoxygenin, β-sitosterol, uvaol, ursolic acid, sarsasapogenin, 18,β-glycyrrhetinic acid, betulin, betulinic acid, oleanoic acid, and padocarpic acid.

22. The method of claim 2, wherein T has a structure selected from the group consisting of:

a)
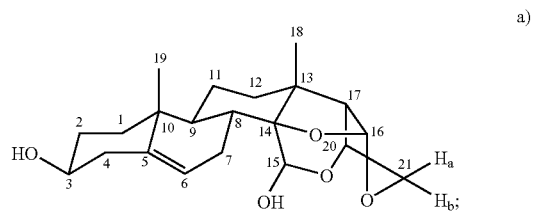

b)
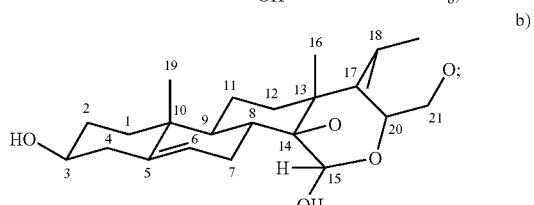

c)
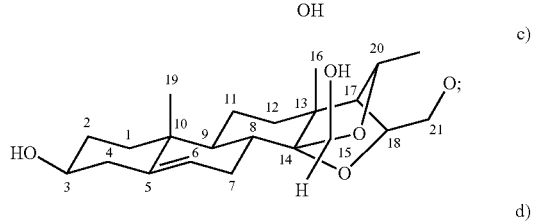

d)
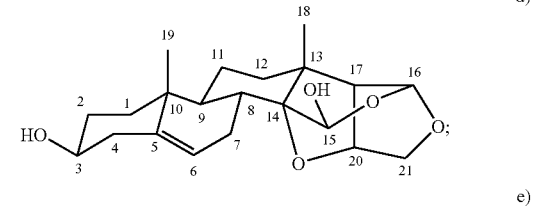

e)
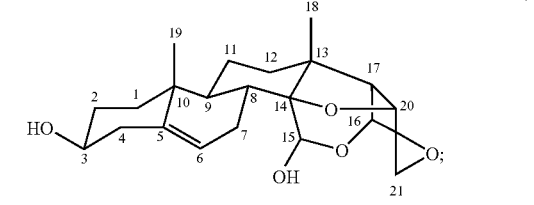

f)
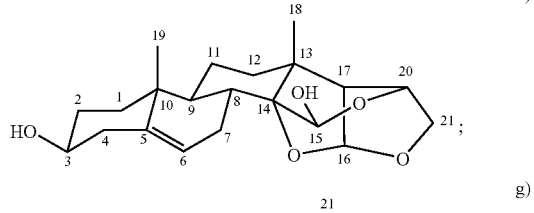

g)
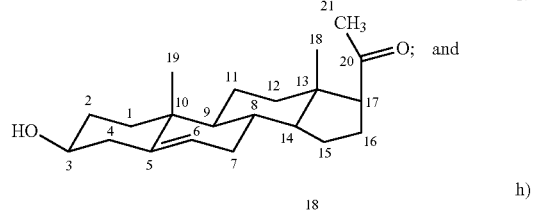

h)
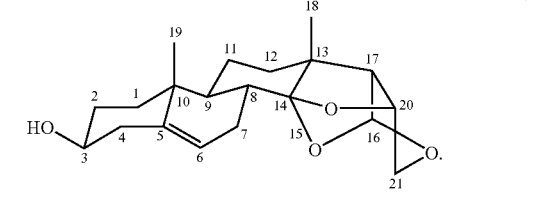

together with a pharmaceutically acceptable carrier.

23. A method for specifically inhibiting overstimulation of a R-type $Ca^{2+}$ channel in a warm blooded animal in need of an inhibition of said overstimulation, comprising an administration of an effective amount of a compound comprising a structure selected from the group consisting of:
a)
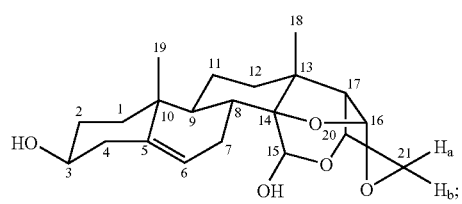
b)
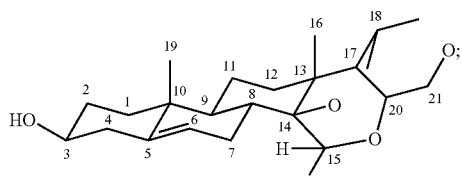
c)
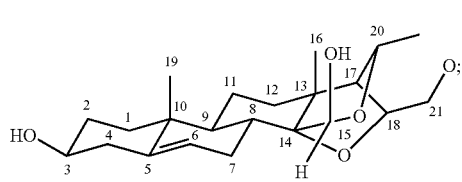
d)
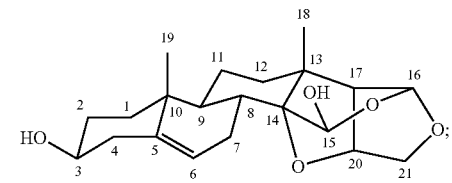
e)
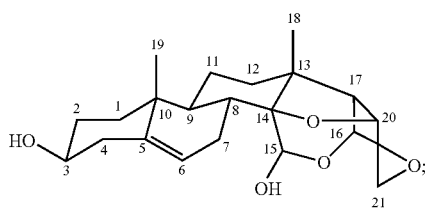
f)
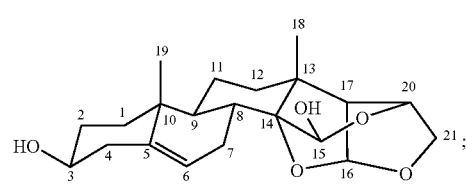
g)
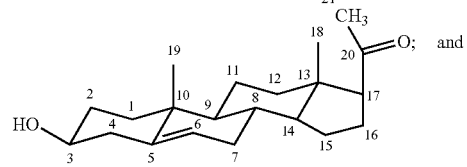
and
h)
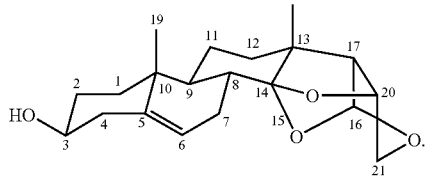
together with a pharmaceutically acceptable carrier.
* * * * *